United States Patent [19]
Berg et al.

[11] Patent Number: 5,506,118
[45] Date of Patent: Apr. 9, 1996

[54] METHOD OF USING EUKARYOTIC EXPRESSION VECTORS COMPRISING A POLY GT ELEMENT IN THE PRESENCE OF TRANS-ACTING GENE PRODUCTS

[75] Inventors: David T. Berg, Beech Grove; Brian W. Grinnell, Indianapolis, both of Ind.

[73] Assignee: Eli Lilly and Company, Indianapolis, Ind.

[21] Appl. No.: 110,475

[22] Filed: Aug. 23, 1993

Related U.S. Application Data

[63] Continuation of Ser. No. 914,651, Jul. 15, 1992, abandoned, which is a continuation of Ser. No. 255,203, Oct. 7, 1988, abandoned.

[51] Int. Cl.⁶ ............................. C12P 21/02; C12N 5/10; C12N 15/85
[52] U.S. Cl. .................. 435/69.1; 435/240.2; 435/320.1
[58] Field of Search ............................. 435/69.1, 172.3, 435/240.2, 320.1; 536/23.72, 24.1

[56] References Cited

U.S. PATENT DOCUMENTS

| | | | |
|---|---|---|---|
| 4,562,155 | 12/1985 | Ricciardi et al. | 435/172.3 |
| 4,740,461 | 4/1988 | Kaufman | 435/69.1 |

FOREIGN PATENT DOCUMENTS

| | | | |
|---|---|---|---|
| 0154566 | 9/1985 | European Pat. Off. | C12N 15/00 |
| 0191606 | 8/1986 | European Pat. Off. | C12N 15/00 |
| 0215548 | 3/1987 | European Pat. Off. | C12N 15/00 |
| 0245949 | 11/1987 | European Pat. Off. | C12N 15/00 |

OTHER PUBLICATIONS

Li (1984), J. Gen. Virol. 65, 1817–1825.
Lamins (1982), PNAS, USA 79, 6453–6457.
Hamada and Kakunaga, 1982, Nature, 298:396–398.
Hamada et al., 1982, Proc. Natl. Acad. Sci. USA, 79:6465–6469.
Hamada et al., 1984, Mol. Cell. Biol., 4:2610–2621.
Hamada et al., 1984, Mol. Cell. Biol., 4:2622–2630.
Yang and Wu, 1979, Science, 26:456–462.
Seif et al., 1979, Cell, 18:963–977.
Rosenthal et al., 1983, Science, 222:749–755.
Milanesi et al., 1984, Mol. Cell. Biol., 4(8):1551–1560.
Khoury and Gruss, 1983, Cell, 33:313–314.
Wingender, 1988, Nucl. Acids Res., 16:1879–1912.
Borelli, et al., 1984, Nature, 312:608–612.
Velcich and Ziff, 1985, Cell, 40:705–716.
Hen et al., 1985, Science, 230:1391–1394.
Wood et al., 1984, Nature, 112:330–337.
Zain et al., 1979, Cell, 16:851–861.
Solnick, 1981, Cell, 24:135–143.
Berkner and Sharp, 1985, Nuc. Acids Res., 13(3):841–857.
Kaufman, 1984, Proc. Natl. Acad. Sci. USA, 82:689–693.
Mansour et al., 1985, Proc. Natl. Acad. Sci. USA, 82:1359–1363.
Davis et al., 1985, Proc. Natl. Acad. Sci. USA, 82:7560–7564.
Wasylyk et al., 1983, Cell, 32:503–514.
Imperiale et al., 1983, Cell, 35:127–136.
Green et al., 1983, Cell, 35:137–148.
Gaynor et al., 1984, Proc. Natl. Acad. Sci. USA, 81:1193–1197.
Alwine, 1985, Mol. Cell. Biol., 5(5):1034–1042.
Lewis and Manley, 1985, Nature, 317:172–175.
Lebkowski et al., 1985, Nature 317:169–171.
Weeks and Jones, 1985, Nuc. Acids Res., 13(14):5339–5402.
Leff and Chambon, 1986, Mol. Cell. Biol., 6(1):201–208.
Grinnell et al., 1987, Bio/Technology, 5:1189.
Yan et al., 1987, Fed. Proc., 46:2243.
Grinnell et al., 1986, abstract from Tumor Virus Meeting.
Grinnell et al., 1986, Mol. Cell. Biol., 6(11):3596.
Grinnell et al., 1987, abstract from 17th Steenbock Symposium.
Berg et al., 1988, Nuc. Acids Res., 16:1635.
Grinnell et al., 1988, Mol. Cell. Biol., 8:3448.
Foster et al., 1987, Biochemistry, 26:7003.
Kumar et al., 1986, Proc. Nat. Acad. Sci. USA, 83:3199.
Spangler et al., 1987, Science, 237:1044.
Alonso–Caplen et al., 1987, abstract from Translational Control Meeting.
Hauschka et al., 1986, Haemostasis, 16:273.
Borrelli, et al., 1986, Proc. Natl. Acad. Sci. USA, 83:2846.
Jalinot and Kedinger, 1986, Nuc. Acids Res., 14:2641.
Jones, et al., 1988, Genes and Devel., 2:267.
Nevins, et al., 1988, Biochem. Cell. Biol., 66:578.
Grand, et al., 1987, Biochem. J., 241:25.
Truett et al., DNA, vol. 4, No. 5 pp. 333–349 (1985).

*Primary Examiner*—Mindy Fleisher
*Assistant Examiner*—James Ketter
*Attorney, Agent, or Firm*—Douglas K. Norman

[57] ABSTRACT

The present invention is a method of using a poly-GT element with a eukaryotic promoter in the presence of an immediate-early gene product of a large DNA virus to increase transcription of DNA that encodes a useful substance. The method of the present invention requires the presence of the E1A gene product for maximum expression of the useful substance. A novel enhancer system is described comprising a cis-acting poly-GT element and a trans-acting E1A gene product, whereby the poly-GT element does not itself possess enhancer activity with certain eukaryotic promoters but rather requires the E1A gene product for enhancer activity. The present invention further comprises a number of useful expression vectors that comprise a poly-GT element with a BK enhancer in tandem with the adenovirus 2 late promoter positioned to drive expression of a variety of proteins, such as protein C, chloramphenicol acetyltransferase, tissue plasminogen activator, a modified tissue plasminogen activator, or an interferon. The present invention also comprises a method for further increasing the expression of a useful substance involving a poly-GT element, the E1A gene product, and a BK enhancer which has been placed immediately upstream (within 0 to about 300 nucleotides) of the eukaryotic promoter used in tandem with a BK enhancer.

51 Claims, 42 Drawing Sheets

5,506,118

1

METHOD OF USING EUKARYOTIC EXPRESSION VECTORS COMPRISING A POLY GT ELEMENT IN THE PRESENCE OF TRANS-ACTING GENE PRODUCTS

This application is a continuation of application Ser. No. 07/914,651, filed on Jul. 15, 1992, now abandoned which is a continuation of application Ser. No. 07/255,203, filed on Oct 7, 1988, now abandoned.

BACKGROUND OF THE INVENTION

The present invention concerns a method of using a poly-GT element in the presence of an immediate-early gene product of a large DNA virus to increase transcription of a recombinant gene in eukaryotic host cells. The poly-GT element exemplified herein is chemically synthesized (the prototype poly-GT element is depicted in Example 1 below). When inserted into an expression vector, the prototype poly-GT element comprises 21 repeating GT units. However, a wide variety of poly-GT elements, comprising repeating units of varying lengths will be recognized by those skilled in the art as suitable for use in the present invention, including chemically synthesized sequences or human genomic sequences. An enhancer element may be used along with the poly-GT element in the present invention to further increase such transcription. In some constructs, the poly-GT sequence is associated with the BK enhancer. The BK enhancer is a defined segment of DNA that consists of repeated sequences (the prototype BK enhancer and a variant BK enhancer are depicted in Example 18, below). However, a wide variety of BK enhancer variants, not all consisting of varying repeated sequences, are known in the art and suitable for use in the invention along with the poly-GT element.

The alternating sequence, poly (dT-dG).poly (dC-dA), is a highly repeated sequence in the eukaryotic genome and is capable of forming left-handed or Z-DNA. Hamada and Kakunaga. 1982, *Nature* 298:396–398; Hamada et al., 1982, *Proc. Natl. Acad. Sci. U.S.A.* 79:6465–6469. For example, the human genome contains approximately 100,000 copies of 20 to 60 base pair (bp) tracts of poly (dT-dG) poly (dC-dA) randomly distributed. Hamada et al., 1984, *Mol. Cell. Biol.* 4:2610–2621. Hamada et al., 1984, *Mol. Cell. Biol.* 4:2622–2630, disclose that poly (dT-dG) poly (dC-dA) itself can act as an enhancer of the expression of chloramphenicol acetyltransferase (CAT) when the poly (dT-dG) poly (dC-dA) is linked to the SV40 early promoter and to the coding sequence for CAT. According to Hamada et al., supra, the enhancer-like activity of poly (dT-dG) poly (dC-dA) with the SV40 early promoter was much weaker than that of the SV40 enhancer with the SV40 early promoter, and, unlike many viral enhancers, the poly(dT-dG) poly (dC-dA) was equally active in monkey (CV-1) or human (HeLa) cells.

The BK enhancer sequences exemplified herein are obtained from BK virus, a human papovavirus that was first isolated from the urine of an immunosuppressed patient. BK virus is suspected of causing an unapparent childhood infection and is ubiquitous in the human population. Although BK virus grows optimally in human cells, the virus undergoes an abortive cycle in many non-primate cells, transforms rodent cells in vitro, and induces tumors in hamsters. BK virus is very similar to SV40 virus, but the enhancer sequences of these two papovaviruses, SV40 and BK, differ substantially in nucleotide sequence. The complete nucleotide sequence of BK virus (~5.2 kb) has been disclosed by Seif et al., 1979, *Cell* 18:963, and Yang and Wu, 1979, *Science* 206:456. Prototype BK virus is available from the American Type Culture Collection (ATCC), 12301 Parklawn Dr., Rockville, Md. 20852-1776, under the accession number ATCC VR-837. A restriction site and function map of prototype BK virus is presented in FIG. 1 of the accompanying drawings.

Enhancer elements are cis-acting elements that increase the level of transcription of an adjacent gene from its promoter in a fashion that is relatively independent of the position and orientation of the enhancer element. In fact, Khoury and Gruss, 1983, *Cell* 33:313, state that "the remarkable ability of enhancer sequences to function upstream from, within, or downstream from eukaryotic genes distinguishes them from classical promoter elements . . ." and suggest that certain experimental results indicate that "enhancers can act over considerable distances (perhaps >10 kb)."

The present invention teaches a novel enhancer system, because the poly-GT element, when placed in combination with certain promoters, such as the adenovirus late promoter, functions as an enhancer only in the presence of a transacting early viral gene product, such as the E1A gene product. Other enhancer elements, such as the BK enhancer, may be used along with the poly-GT element in the present invention. The present invention specifically teaches an enhancer system for the adenovirus late promoter that results in unexpected increases in transcription only where there is a combination of a cis-acting poly-GT element with a trans-acting immediate-early gene product of a large DNA virus. Thus, a viral transacting protein is required to activate enhancer activity from the poly-GT element. This is in striking contrast to the enhancer system of Hamada et al, supra, where a poly-GT sequence alone was capable of enhancing expression of the CAT gene product using the SV40 early promoter. In the present invention, another enhancer element may be used along with the poly-GT element and the trans-acting viral gene product to further increase transcription and thus expression of a useful gene product.

When the BK enhancer is used along with the poly-GT element, still further increases in transcription result upon positioning the BK enhancer immediately upstream of (on the 5' side of) the "CCAAT" region of a eukaryotic promoter that is used in tandem with the BK enhancer to transcribe a DNA sequence encoding a useful substance. The CCAAT region or "immediate upstream region" or "−80 homology sequence" is a cis-acting upstream element that is a conserved region of nucleotides observed in promoters whose sequences for transcriptional activity have been dissected. The CCAAT region is found in many, but not all, promoters. In other promoters, equivalent cis-acting upstream sequences are found, including SP1 binding sites, ATF binding sites, the octa sequence, nuclear factor 1 binding sites (which may be the same binding site as the CCAAT transcription factor), the AP1 and AP2 homologies, glucocorticoid response elements, and heat shock response elements. Recently, a comprehensive compilation of currently known upstream sequences, including those just listed, has been published. Wingender, 1988, *Nucl. Acids Res.* 16:1879–1912. The CCAAT region equivalent in the adenovirus major la.te promoter is the upstream transcription factor (UTF) or major late transcription factor (MLTF) binding site (approximate nucleotides −50 to −65 upstream of the CAP site). The CCAAT sequence mediates the efficiency of transcription and, with few exceptions, cannot be deleted without decreasing promoter strength.

Enhancer elements have been identified in the DNA of a number of viruses, including murine polyomavirus, papilloma virus, adenovirus, retrovirus, hepatitis virus, cytomegalovirus, herpes virus, papovaviruses, such as SV40 and BK, and in many non-viral genes, such as within immunoglobulin gene introns. Enhancer elements may also be present in the DNA of a wide variety of other organisms. Enhancer elements often function differently in different host cells, and this cellular specificity can be due to differences in host gene products that interact with the enhancer element during gene expression.

The activity of enhancer elements can be affected by viral gene products present in the host cell. Velcich and Ziff, 1983, *Cell* 40:705; Borrelli et al., 1984, *Nature* 312:608; and Hen et al., 1985, *Science* 230:1391, disclose that the adenovirus-2 early region 1A (E1A) gene products repress activation of transcription induced by the SV40, polyoma virus, mouse immunoglobulin gene and adenovirus-2 E1A enhancers. This affect by E1A can be host cell dependent. Eukaryotic expression vectors that utilized enhancers to increase transcription of recombinant genes consequently were not expected to work better than vectors without enhancers in E1A-containing host cells. In striking contrast to the above-referenced prior art methods of using enhancers, co-pending application Ser. No. 07/129,028, filed on Dec. 4, 1987, attorney docket number X-6606A, teaches a method for using the BK virus enhancer element that involves using the E1A gene product or a similar immediate-early gene product of a large DNA virus to maximize gene expression. Thus, co-pending application Ser. No. 07/129,028 demonstrates. for the first time that the ability of the BK enhancer to promote transcription of DNA is increased in the presence of the E1A gene product of any adenovirus. It has now been unexpectedly found that a poly-GT element may be used along with the BK enhancer to further increase transcription of DNA in the presence of the E1A gene product of any adenovirus. When the adenovirus late promoter is used to drive transcription, the polyoGT element surprisingly does not itself enhance transcription, but is activated and does demonstrate enhancer activity only in the presence of the E1A gene product or a similar immediate-early gene product of a large DNA virus. Because the E1A gene product has been shown to repress activation of transcription by most enhancers tested, it was not expected that E1A would have the ability to activate an enhancer-like activity of a poly-GT element. The E1A gene product (actually, the E1A gene produces two products, which are collectively referred to herein as "the E1A gene product") is one such immediate-early gene product from adenovirus, a large DNA virus. The present invention encompasses the use of any immediate-early gene product of a large DNA virus or any retroviral protein product that functions similarly to the E1A gene product to increase the activity of a poly-GT element with or without another enhancer element, such as the BK enhancer. The herpes simplex virus ICP4 protein, described by DeLuca et al., 1985, *Mol. Cell. Biol.* 5:1997–2008, the pseudorabies virus IE protein, described by Feldman et al., 1982, *Proc. Natl. Acad. Sci.* U.S.A. 79:4952– 4956, the cytomegalovirus IE protein described by Tevethia et al., 1987, *Virology* 161:276–285, and the E1B protein of adenovirus are all immediate-early gene products of large DNA viruses that have functions similar to the E1A protein. Therefore, the method of the present invention includes the use of the ICP4, IE, or E1B proteins, or any other similarly acting immediate-early gene product, either in the presence or absence of E1A protein, to produce or activate an enhancer-like activity from a poly-GT element. In addition, other trans-acting viral proteins, such as the TAT gene product of the HIV virus or other retroviral proteins, may be useful in the method to activate a poly-GT element.

SUMMARY OF THE INVENTION

The present invention concerns a method of using a poly-GT element in the presence of an immediate-early gene product of a large DNA virus, such as the E1A gene product of adenovirus, or a similarly functioning viral gene product, for purposes of increasing transcription and thus improving expression of recombinant genes in eukaryotic host cells. Another significant aspect of the present invention relates to a variety of expression vectors that utilize the poly-GT element with a eukaryotic promoter, such as the adenovirus late promoter (MLP), in the presence of an immediate-early gene product of a large DNA virus, such as the E1A gene product of adenovirus, to drive expression of useful products in eukaryotic host cells. In addition, an enhancer element such as the BK enhancer may be used along with the poly-GT element to further enhance expression of such useful products. Many of these expression vectors comprise a poly-GT-adenovirus late promoter cassette, which can be readily transferred to other vectors for use in the present method. The cassette may further comprise an enhancer element, such as the BK enhancer. The versatility of the present expression vectors is demonstrated by the highlevel expression that may be driven by these vectors of such diverse proteins as chloramphenicol acetyltransferase, protein C, tissue plasminogen activator, modified tissue plasminogen activator or an interferon ($\alpha$, $\beta$ or $\gamma$ interferon).

It is a characteristic of enhancer elements that they can enhance transcription from a distance and that their activity is not dependent on their orientation. Consistent with this, the poly-GT element of this invention may be positioned 5' or 3' to the structural gene to be expressed. Thus, in the construction of certain recombinant DNA expression vectors of the present invention, the poly-GT element was placed upstream of the adenovirus late promoter, itself positioned to drive expression of a recombinant gene on a recombinant DNA expression vector. In addition, in certain of such constructions, a BK enhancer element was placed upstream of the poly-GT element. In the construction of the other recombinant DNA expression vectors of the invention, the poly-GT element was placed at the 3' end of a structural gene to be expressed, demonstrating that the poly-GT element could function in various positions and orientations as has been described for other enhancer elements.

The practice of the invention results in increase in expression of human protein C in adenovirus-transformed cells. Such cells are especially preferred hosts for the production of fully $\gamma$-carboxylated proteins, such as human protein C. Consequently, a further aspect of the invention comprises an improved method for making $\gamma$-carboxylated proteins.

Yet another important aspect of the present invention concerns a method of further increasing the expression of a useful gene product by (a) positioning the BK enhancer relative to an adjacent eukaryotic promoter, (b) placing a poly-GT element in such an expression vector and (c) activating such a poly-GT element (and the BK enhancer) with an immediate-early gene product of a large DNA virus or any viral gene product that functions similarly to the E1A gene product. In a first step, these derivatives were constructed by enzymatic treatment that positioned the BK enhancer very close to the MLTF binding site. Dramatic increases in expression levels, as compared with constructions that lack this positioning, were observed when these modified BK enhancer-adenovirus late promoter sequences were incorporated into expression vectors and then used to drive expression of useful gene products in eukaryotic host cells. In a second step, these derivatives were further constructed by placing a poly-GT element in either orientation at the 3' end of a gene encoding a useful product. Further increases in expression levels, as compared with constructions that lack the poly-GT element, were observed. Thus, the present invention provides a method for further increasing expression of a useful gene product by increasing the activity of the BK enhancer relative to an adjacent eukaryotic promoter that comprises positioning the enhancer immediately upstream, within 0 to about 300 nucleotides, of the 5' end of the CCAAT region or CCAAT region equivalent of the eukaryotic promoter and by activating a poly-GT element irrespective of its position and orientation with E1A gene product.

Yet another aspect of the invention results from attempts to increase expression of recombinant products encoded on the vectors described herein by incorporation of a poly-GT element into certain expression vectors in which have been incorporated portions of the tripartite leader (TPL) sequence of adenovirus. Increases in expression result when the TPL sequence is incorporated along with the poly-GT element in such expression vectors and the poly-GT element is activated in the presence of the E1A gene product of adenovirus. Further increases in expression in such TPL-containing vectors may result in the presence of the VA gene product of adenovirus.

For purposes of the present invention, the following terms are as defined below:

Antibiotic—a substance produced by a microorganism that, either naturally or with limited chemical modification, will inhibit the growth of or kill another microorganism or eukaryotic cell.

Antibiotic Resistance-Conferring Gene—a DNA segment that encodes an activity that confers resistance to an antibiotic.

ApR—the ampicillin-resistant phenotype or gene conferring same.

Cloning—the process of incorporating a segment of DNA into a recombinant DNA cloning vector.

CmR—the chloramphenicol-resistant phenotype or gene conferring same.

E1A—an immediate-early gene product of adenovirus which can activate a poly-GT element to express enhancer activity.

ep—a DNA segment comprising the SV40 early promoter of the T-antigen gene, the T-antigen binding sites, and the SV40 origin of replication.

Eukaryotic promoter—any DNA sequence that functions as a promoter in eukaryotic cells.

GT enhancer system—any poly-GT element linked to a promoter, such as MLP, in which the poly-GT element does not itself possess enhancer activity but is activated as an enhancer by an immediate-early gene product of a large DNA virus, such as the E1A gene product or by any similarly activating viral gene product.

HmR—the hygromycin-resistant phenotype or gene conferring same.

IVS—DNA encoding an intron, also called an intervening sequence.

Large DNA virus—a virus that infects eukaryotic cells and has a genome greater than ~10 kb in size, i.e., any of the pox viruses, adenoviruses, and herpes viruses.

MLP—the major late promoter of adenovirus, which is also referred to herein as the adenovirus late promoter, adenovirus-type-2 late promoter, or Ad2 late promoter.

MLTF binding site—the site in adenovirus DNA where the major late transcription factor (MLTF) binds; the MLTF is required for MLP activity.

NeoR—the neomycin resistance-conferring gene, which can also be used to confer G418 resistance in eukaryotic host cells.

ori—a plasmid origin of replication.

pA—a DNA sequence encoding a polyadenylation signal.

Poly-GT element—a DNA sequence of $(GT)_n$-$(CA)_n$, which is illustrated herein by a sequence where n is 21, but which can also refer to sequences of varying lengths where n is greater or less than 21, and may refer to chemically synthesized $(GT)_n$-$(CA)_n$ sequences or human genomic DNA fragments containing a $(GT)_n$-$(CA)_n$ tract.

Promoter—a DNA sequence that directs transcription of DNA into RNA.

Recombinant DNA Cloning Vector—any autonomously replicating or integrating agent that comprises a DNA molecule to which one or more additional DNA segments can be or have been added.

Recombinant DNA Expression Vector—any recombinant DNA cloning vector comprising a promoter and associated insertion site, into which a DNA sequence that encodes a useful product can be inserted and expressed.

Recombinant DNA Vector—any recombinant DNA cloning or expression vector.

Replicon—any DNA sequence that controls the replication of a recombinant DNA vector.

Restriction Fragment—any linear DNA generated by the action of one or more restriction enzymes.

rRNA—ribosomal ribonucleic acid.

Sensitive Host Cell—a host cell that cannot grow in the presence of a given antibiotic or other toxic compound without a DNA segment that confers resistance thereto.

Structural Gene—any DNA sequence that encodes a polypeptide, inclusive of that DNA encoding the start and stop codons.

TAT—a gene product of the retrovirus HIV which has activity as a trans-acting viral protein.

TcR—the tetracycltne-resistance phenotype or gene conferring same.

Transformant—a recipient host cell that has undergone transformation.

Transformation—the introduction of DNA into a recipient host cell.

tRNA—transfer ribonucleic acid.

BRIEF DESCRIPTION OF THE FIGURES

FIG. 12, Part 2; FIG. 12, Part 3, Page 1; and FIG. 12, Part 3, Page 2 depict the construction and presents a restriction site and function map of plasmid pBW32.

DETAILED DESCRIPTION OF THE INVENTION

Figure 1:
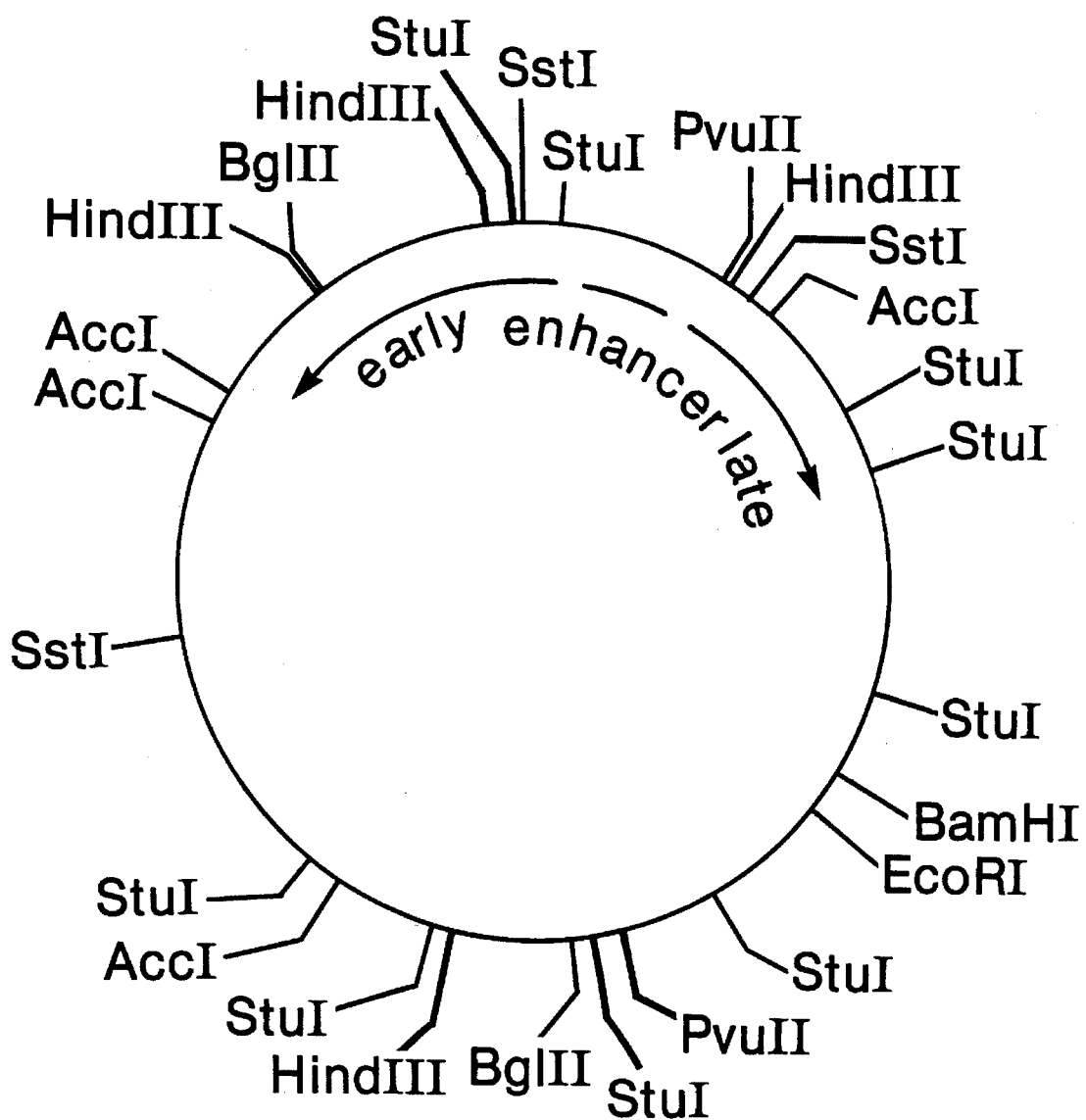
FIG. 1 is a restriction site and function map of BK virus.

The present invention concerns an improved method for producing a useful substance in a eukaryotic host cell wherein the cell is transformed with a recombinant DNA vector that comprises a eukaryotic promoter, a poly-GT element positioned to stimulate the promoter, and a DNA sequence that encodes the useful substance, the DNA sequence being positioned for expression from the promoter, and wherein the cell containing the vector is cultured under conditions suitable for expression of the useful substance, wherein the improvement comprises: (a) providing the cell with a DNA sequence that codes for the expression of an immediate-early gene product of a large DNA virus; and (b) culturing the cell of step (a) under conditions suitable for expressing the immediate-early gene product and stimulating the activity of the poly-GT element. Those skilled in the art recognize that many established cell lines express an immediate-early gene product of a large DNA virus and that such cell lines are especially useful in the present method. Thus, the present invention also comprises an improved method for producing a useful substance in a eukaryotic host cell wherein the cell is transformed with a recombinant DNA vector that comprises a eukaryotic promoter, a poly-GT element positioned to stimulate the promoter, and a DNA sequence that encodes the useful substance, the sequence being positioned for expression from the promoter, and wherein the cell containing the vector is cultured under conditions suitable for expression of the useful substance, wherein the improvement comprises: (a) inserting the vector into a eukaryotic host cell that expresses an immediate-early gene product of a large DNA virus, and (b) culturing the cell of step (a) under conditions suitable for expressing the immediate-early gene product and stimulatin the activity of the poly-GT element.

An important aspect of the present invention is the novel group of expression vectors that comprise a poly-GT element with the adenovirus-2 late promoter. The expression vectors of the present invention were constructed so that DNA molecules encoding useful products can be or have been readily inserted in other vectors in the correct position for enhanced expression via the activation of the poly-GT element by the E1A gene product. Furthermore, the poly-GT element and eukaryotic promoter have been constructed to form a "cassette," which can be isolated from the expression vectors on a relatively small restriction fragment. The cassette can be readily shuttled between a variety of expression vectors. The cassette may contain, in addition to the poly-GT element, an enhancer element, such as the BK enhancer. The expression vectors specifically exemplified herein utilize the adenovirus-2 late promoter in the poly-GT—BK enhancer-eukaryotic promoter cassette that drives transcription in the presence of the E1A gene product in the method of the present invention.

Single-stranded DNA fragments used in the construction of a poly-GT element were chemically synthesized by using a DNA synthesizer. Many DNA synthesizing instruments are known in the art and can be used to synthesize the single-stranded fragments which are then annealed to form a poly-GT element. A poly-GT element is a DNA sequence of $(GT)_n$ -$(CA)_n$, which is illustrated herein by a sequence wherein n is 21, but also refers to sequences of varying lengths where n is greater or less than 21. Such sequences may be chemically synthesized or may be human genomic DNA fragments. The sequence of a prototype poly-GT element is illustrated in Example 1. The illustrated poly-GT element has BamHI and XhoI sites and thus may be conveniently inserted into a BamHI or an XhoI site in a variety of expression vectors. Those skilled in the art will recognize that a synthetic poly-GT element may contain sequences for restriction enzyme recognition sites other than BamHI or XhoI so as to make the poly-GT element easily insertable into any expression vector. Alternatively, regardless of the restriction enzyme recognition sites available in the poly-GT element, the poly-GT element may be inserted by blunt-end ligation into any suitable expression vector.

Figure 2:
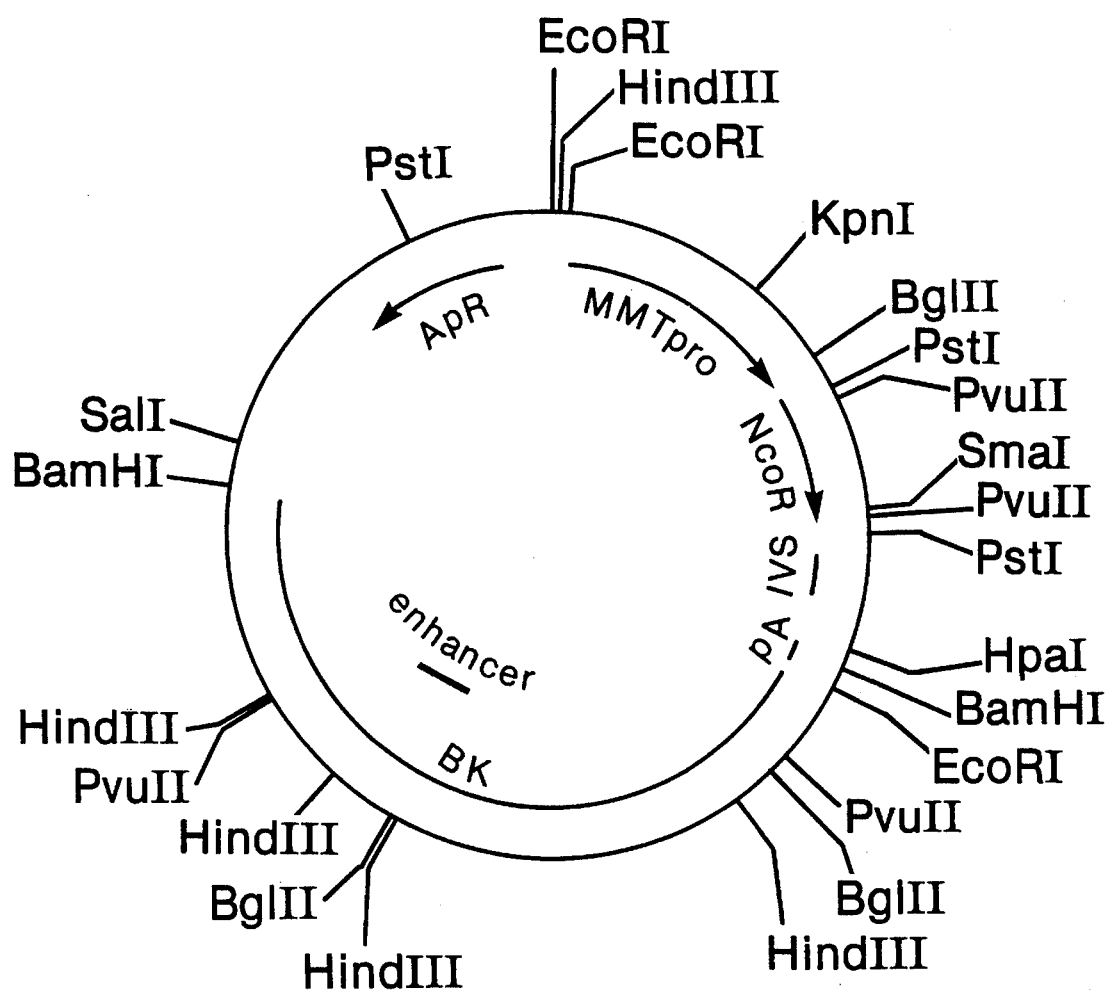
FIG. 2 is a restriction site and function map of plasmid pBKneo1.

BK virus (ATCC VR-837) can be purchased or readily isolated in large quantities, as described in Example 2, for use as a source of BK viral sequences, in particular, as a source of BK enhancer. It is also convenient to clone the BK viral DNA onto a plasmid cloning vector and use the recombinant vector as a source of BK viral DNA sequences. Consequently, the BK viral genome has been combined with a portion of plasmid pdBPV-MMTneo to construct plasmids pBKneo1 and pBKneo2. Plasmid pdBPV-MMTneo, about 15 kb in size and available from the ATCC under the accession number ATCC 37224, comprises the replicon and β-lactamase gene from plasmid pBR322, the mouse metallothionein promoter positioned to drive expression of a structural gene that encodes a neomycin resistance-conferring enzyme, and about 8 kb of bovine papilloma virus (BPV) DNA. Plasmid pdBPV-MMTneo can be digested with restriction enzyme BamHI to generate two fragments: the ~8 kb fragment that comprises the BPV DNA and an ~7 kb fragment that comprises the other sequences described above. BK virus has only one BamHI restriction site, and plasmids pBKneo1 and pBKneo2 were constructed by ligating the ~7 kb BamHI restriction fragment of plasmid pdBPV-MMTneo to BamHI-linearized BK virus DNA. The construction of plasmids pBKneo1 and pBKneo2, which differ only with respect to the orientation of the BK virus DNA, is described in Example 2, and a restriction site and function map of plasmid pBKneo1 is presented in FIG. 2 of the accompanying drawings.

Because plasmids pBKneo1 and pBKneo2 comprise the entire genome of the BK virus, including the enhancer sequence, they serve as useful starting materials for the poly-GT containing expression vectors described herein that also contain the BK enhancer. Other expression vectors that do not contain the BK enhancer are also useful in the present invention.

Figure 3:
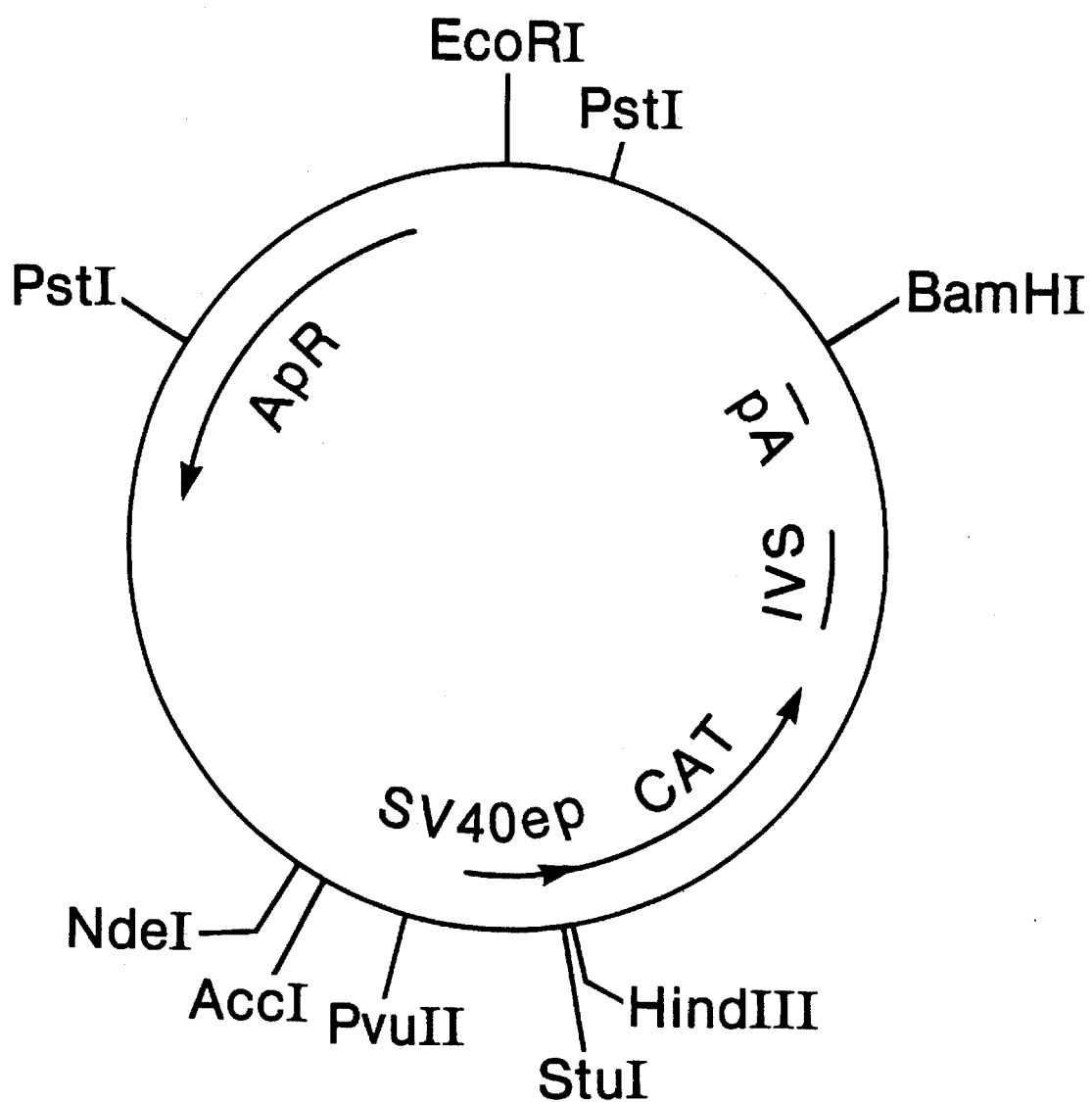
FIG. 3 is a restriction site and function map of plasmid pSV2cat.

One expression vector, plasmid pBLcat, comprises the BK enhancer sequence in tandem with the human adenovirus-type-2 late promoter positioned to drive expression of the chloramphenicol acetyltransferase enzyme (CAT). Plasmid pSV2cat serves as a convenient source of the CAT gene and can be obtained from the ATCC under the accession number ATCC 37155. A restriction site and function map of plasmid pSV2cat is presented in FIG. 3 of the accompanying drawings. Human adenovirus-type-2 DNA is commercially available and can also be obtained from the ATCC under the accession number ATCC VR-2. Another expression vector, plasmid pLPcat, not containing the BK enhancer, comprises the human adenovirus-type-2 late promoter positioned to drive expression of chloramphenicol acetyltransferase. A poly-GT element has been inserted into both plasmids pLPcat and pBLcat to create plasmids pLP(GT)cat and pBL(GT)cat, respectively.

Figure 4:
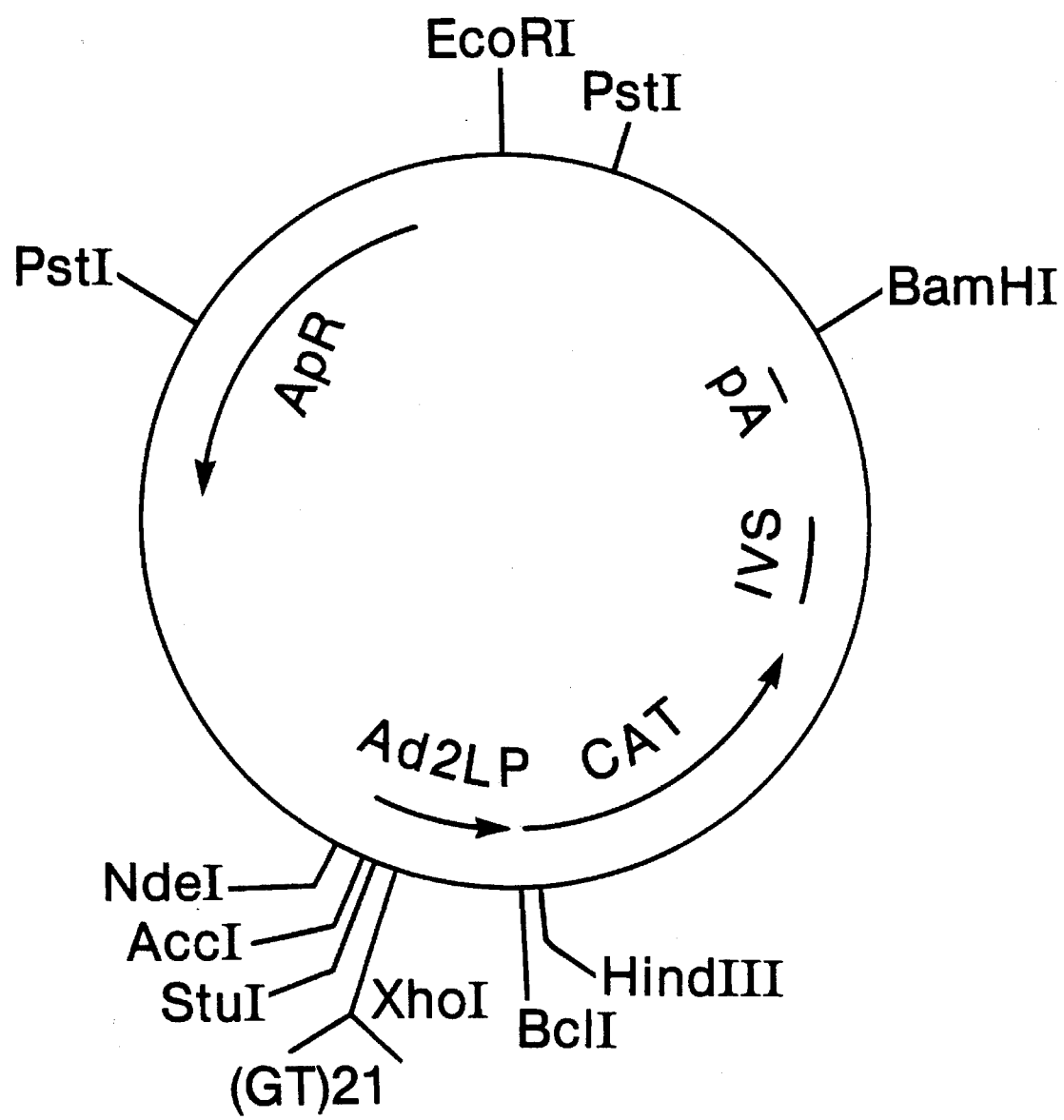
FIG. 4 is a restriction site and function map of plasmid pLP(GT)cat.
Figure 5:
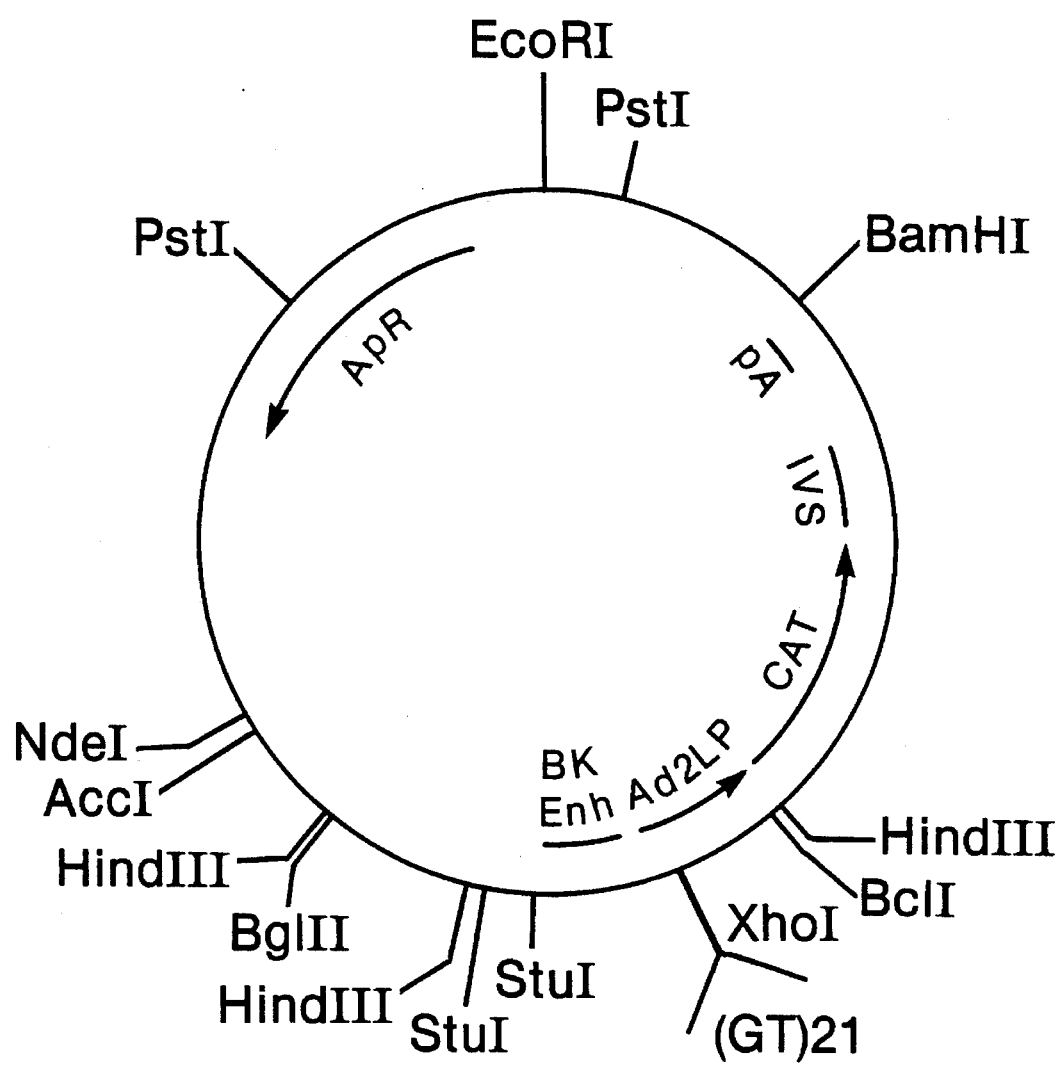
FIG. 5 is a restriction site and function map of plasmid pBL(GT)cat.

Plasmids pLPcat and pBLcat were constructed as follows. The ~0.32 kb late-promoter-containing AccI-PvuII restriction fragment of human adenovirus-type-2 DNA was ligated to blunt-ended BclI linkers that attached only to the PvuII end of the AccI-PvuII restriction fragment. The resulting fragment was then ligated to the ~4.51 kb AccI-StuI restriction fragment of plasmid pSV2cat to yield plasmid pLPcat. Plasmid pBLcat was constructed from plasmid pLPcat by ligating the origin of replication and enhancer-containing, ~1.28 kb AccI-PvuII restriction fragment of BK virus DNA to the ~4.81 kb AccI-StuI restriction fragment of plasmid pLPcat. A poly-GT element is inserted into plasmids pLPcat and pBLcat as follows. A poly-GT element with XhoI linkers is ligated into XhoI digested plasmid pLPcat or pBLcat to create plasmids pLP(GT)cat and pBL(GT)cat, respectively. The unique XhOI site in plasmids pLPcat and pBLcat is located between the BK enhancer and the adenovirus late promoter. The construction of plasmids pLPcat, pLP(GT)cat, pBLcat, and pBL(GT)cat are further described in Examples 4 and 5. Restriction site and function map of plasmids pLP(GT)cat and pBL(GT)cat are presented in FIGS. 4 and 5, respectively, of the accompanying drawings.

Plasmid pBLcat is a convenient source of the BK enhancer-adenovirus late promoter "cassette". This cassette is an ~870 bp HindIII restriction fragment that can be conveniently inserted into a eukaryotic expression vector to increase expression of a product encoded by that vector. Plasmid pBL(GT)cat is a convenient source of the poly-GT BK enhancer—adenovirus late promoter cassette of the present invention. This poly-GT containing cassette is an ~930 bp HindIII restriction fragment that can also be conveniently inserted into a eukaryotic expression vector to further increase expression of a useful gene product encoded by that vector in the presence of an immediate-early gene product of a large DNA virus, such as the E1A gene product. Plasmid pSBLcat and pSBL(GT)cat may be prepared using the above described cassettes. For plasmid pSBLcat, this was done by digesting plasmid pSV2cat with restriction enzyme HindIII and inserting the BK enhancer-adenovirus late promoter cassette. The resultant plasmid, designated as plasmid pSBLcat, contains the BK enhancer and, in addition, the SV40 origin of replication, SV40 early promoter, and SV40 enhancer and therefore differs from plasmid pBLcat in which those additional sequences have been deleted. The tandem SV40 enhancer-BK enhancer-adenovirus major late promote (SBL promoter) cassette can be excised from plasmid pSBLcat on a PvuII restriction enzyme fragment, which can be conveniently inserted into any recombinant DNA expression vector.

Plasmid pSBLcat drives expression of CAT to higher levels than does plasmid pBLcat, so long as no E1A gene product is present. This increased expression in the absence of EIA gene product indicates that the two enhancers, one from SV40 and the other from BK, have an additive, enhancing effect on transcription from nearby promoters in some cell lines. Thus, andem enhancer sequences upstream of a eukaryotic promoter may be used for the efficient expression of genes in a wide variety of mammalian cells. In the presence of E1A gene product, plasmid pBLcat drives expression of CAT to higher levels than does plasmid pSBLcat, presumably because the SV40 enhancer is inhibited by the E1A gene product. Higher levels of expressions of CAT therefore would be expected with plasmid pBL(GT)cat as compared with pSBL(GT)cat in the presence of E1A gene product. Conversely, in HeLa cells, the SV40 enhancer markedly stimulated transcription from the adenovirus 2 late promoter, but the BK enhancer only minimally stimulated transcription from the adenovirus 2 late promoter in HeLa cells. Because the basal level of BK activity in HeLa cells is so low, stimulation of that activity with the immediate-early gene product of a large DNA virus, such as E1A gene product, still does not result in optimal expression levels.

Figure 6:
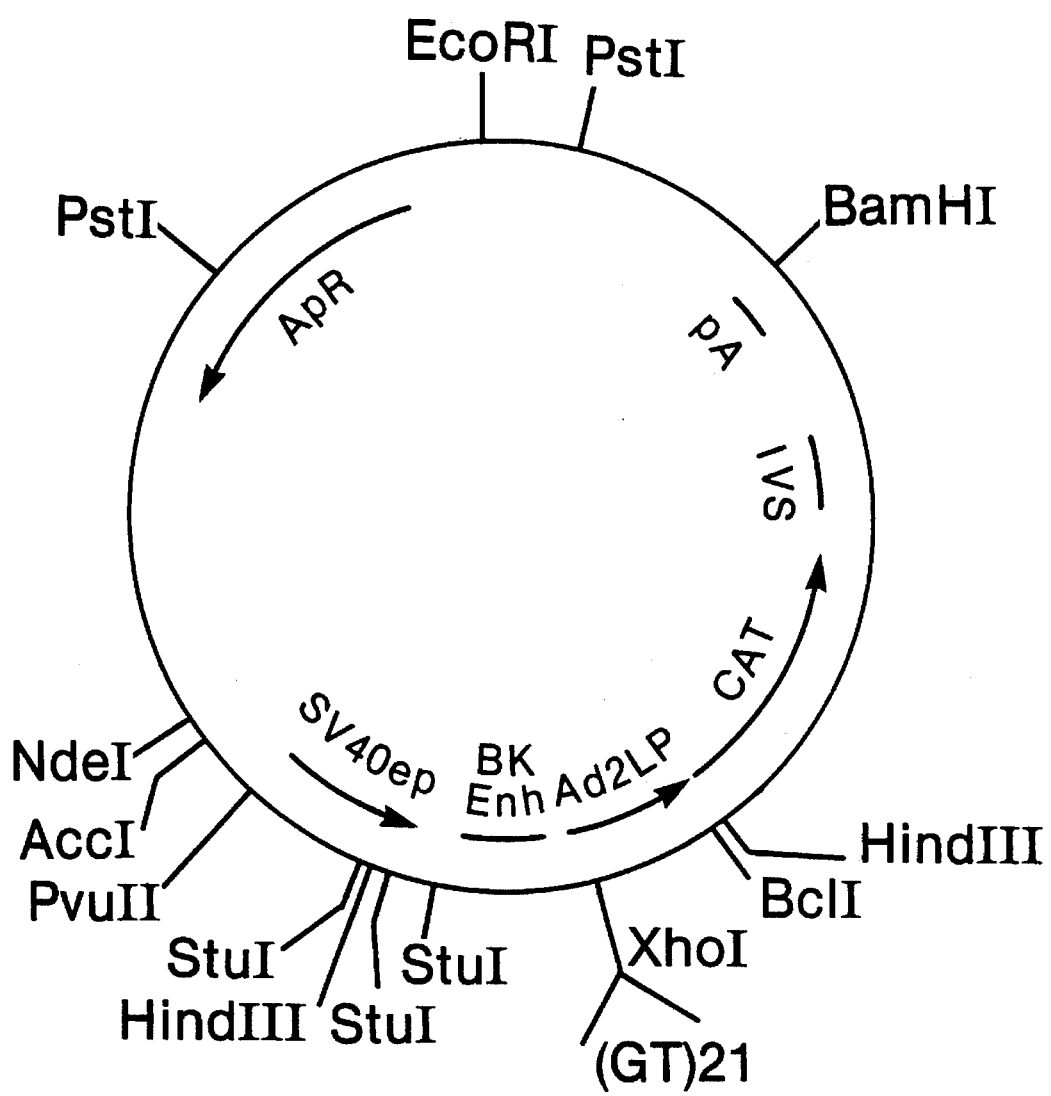
FIG. 6 is a restriction site and function map of plasmid pSBL(GT)cat.

Inserting a poly-GT element along with the BK enhancer appears to have no effect on increasing expression in HeLa cells. This low level activity of the BK enhancer in HeLa cells is thought to be due to a repressor activity present in HeLa cells that interacts with the BK enhancer. This repressor activity in HeLa cells can be titrated out by introducing more copies of the BK enhancer into the HeLa cell. In fact, in the HeLa cell line, E1A may increase the level of the repressor. However, optimal expression levels can be obtained in HeLa cells using the tandem SV40 enhancer—BK-enhancer. This tandem enhancer thus has the advantage of avoiding cell-specific negative interactions that may be encountered, as in HeLa cells, in some host cells. A restriction site and function map of plasmid pSBL(GT)cat is presented in FIG. 6 of the accompanying drawings, and- the construction of plasmids pSBLcat and pSBL(GT)cat are described in Example 6.

Figure 7:
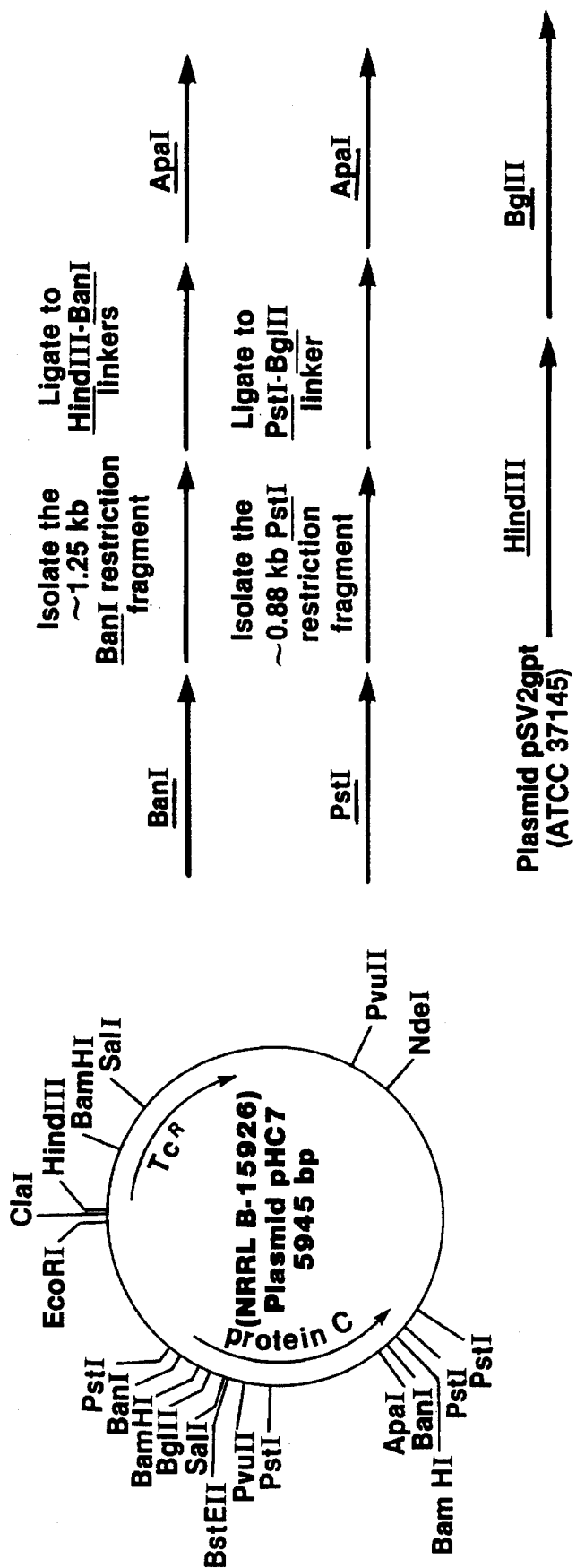
FIG. 7 depicts the construction and presents a restriction site and function map of plasmid pL133.
Figure 7:
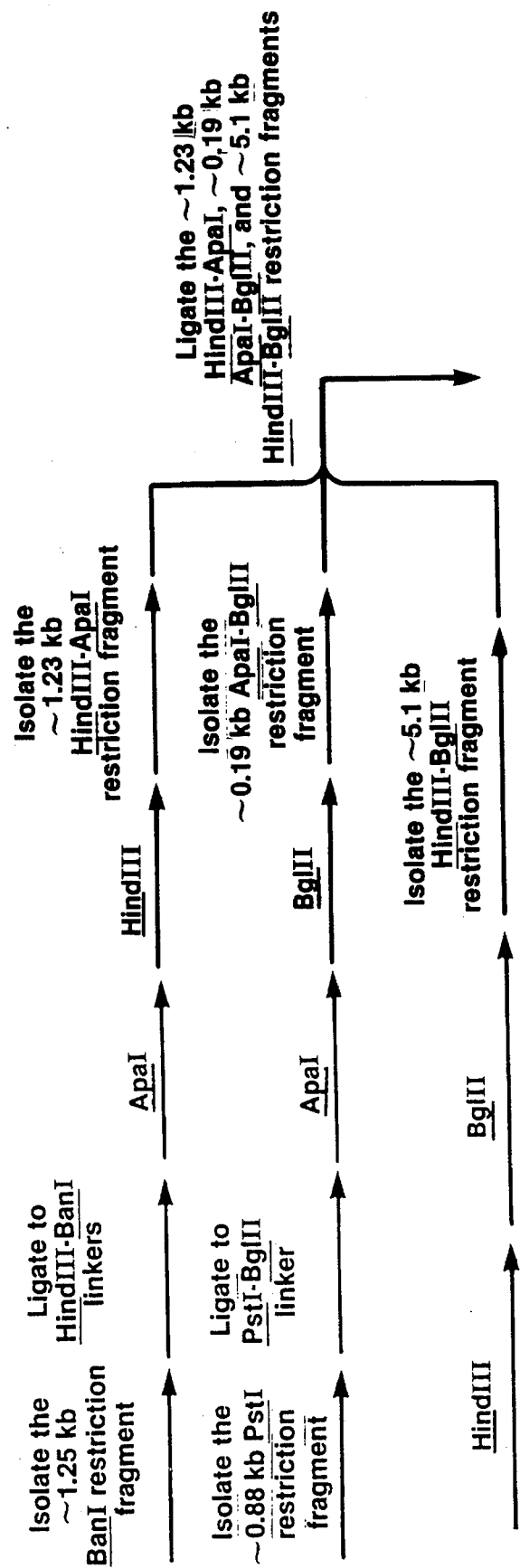
Figure 7:
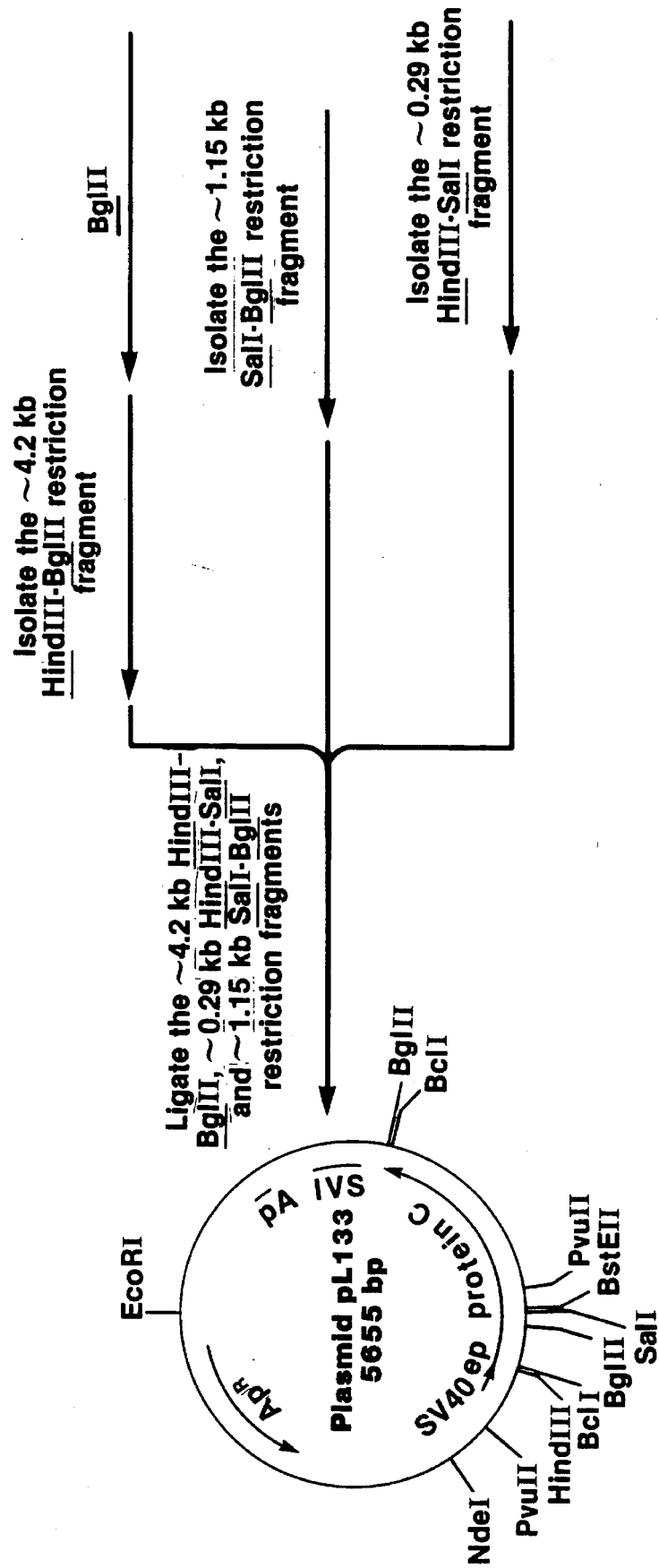
Figure 7:
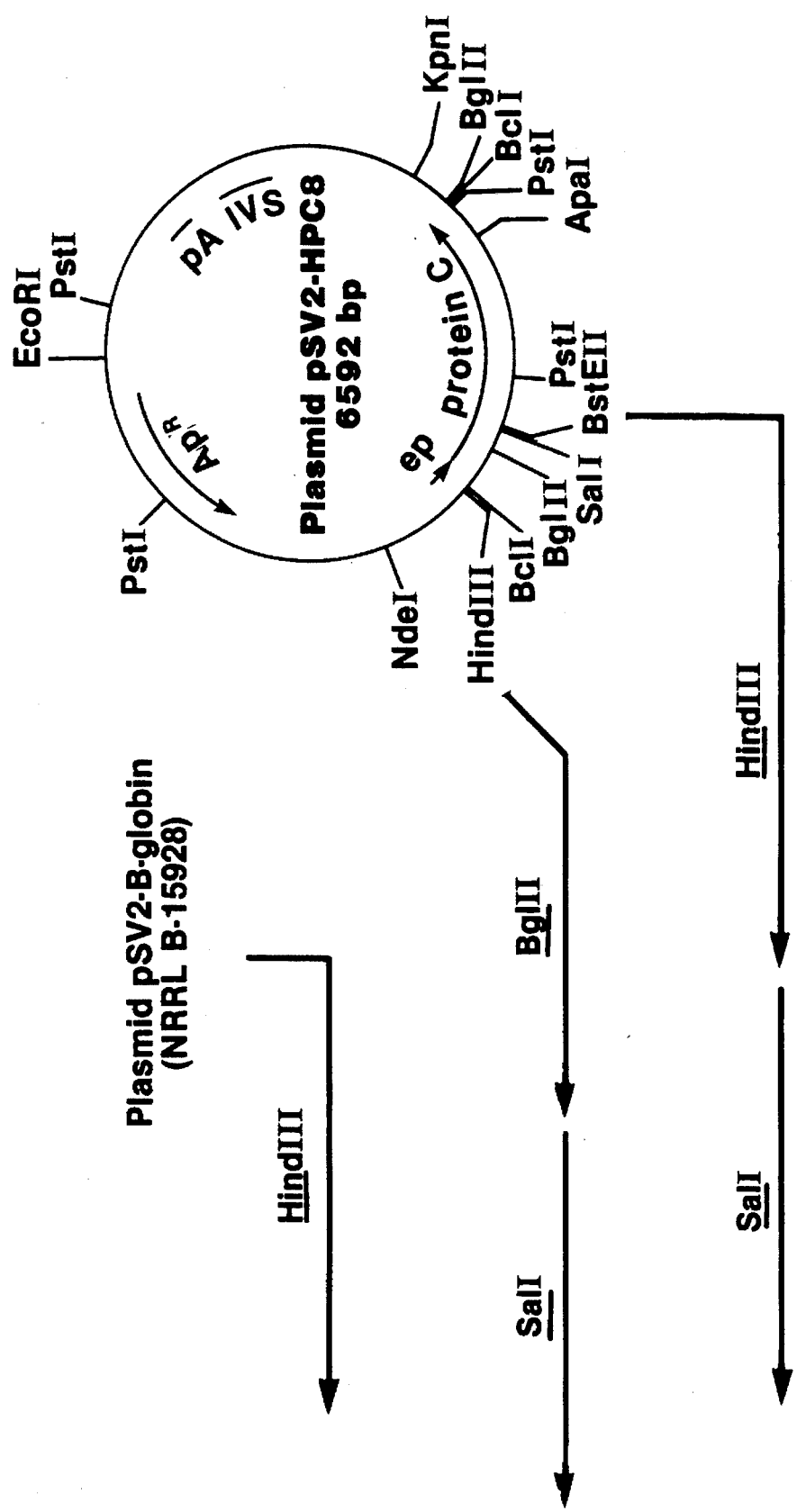
Figure 8:
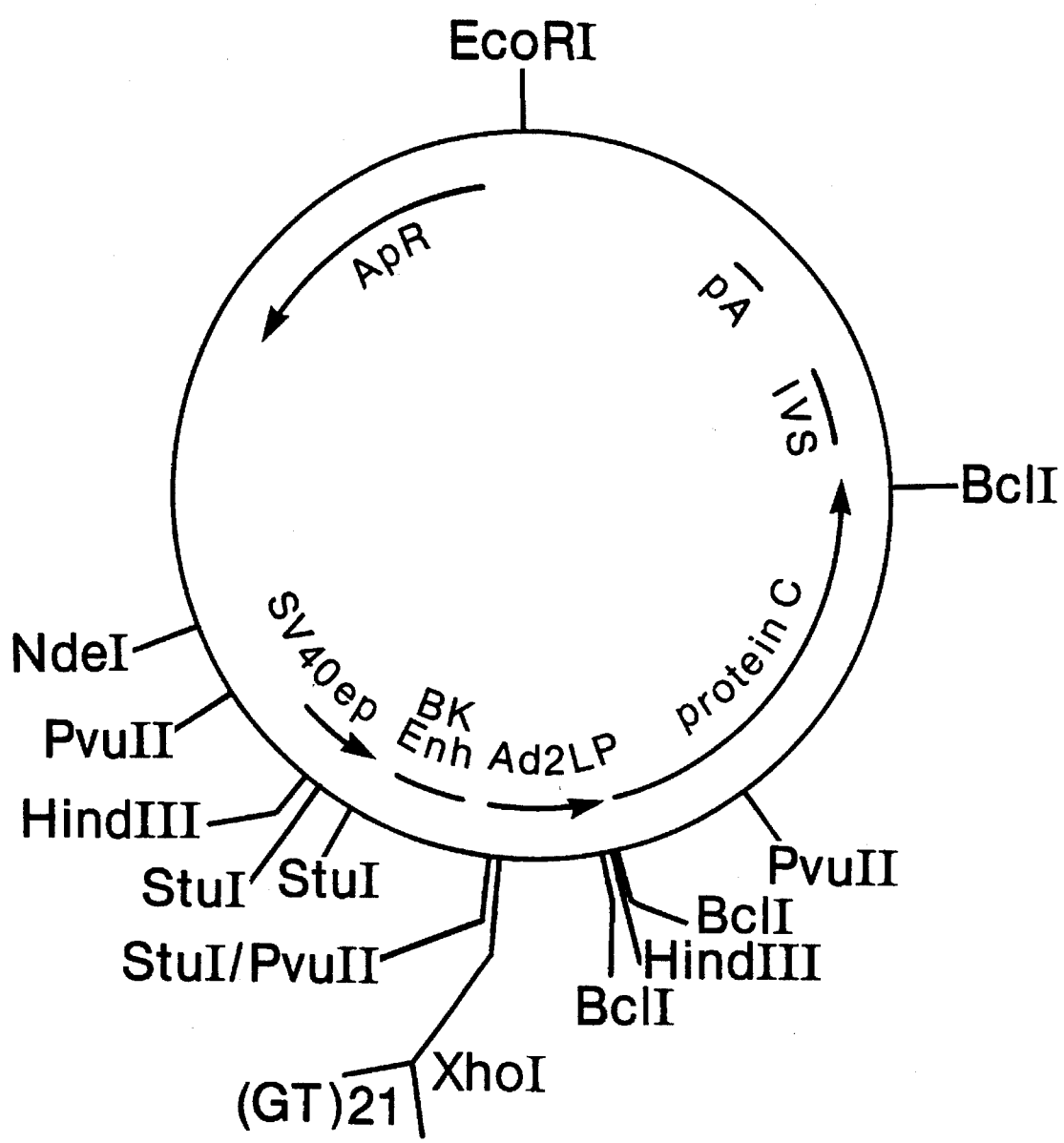
FIG. 8 is a restriction site and function map of plasmid pLPC(GT).

The BK enhancer-adenovirus late promoter cassette has been used for expression of human protein C. The poly-GT— BK enhancer—adenovirus late promoter cassette has been used in the present invention to improve expression of human protein C. Increased expression may be achieved by ligating either of the above-described cassettes into plasmid pL133, a plasmid disclosed and claimed in U.S. patent application Ser. No. 699,967, filed Feb. 8, 1985, (notice of allowance, Apr. 12, 1988) incorporated herein by reference. A restriction site and function map of plasmid pL133 is presented in FIG. 7 of the accompanying drawings. Plasmid pL133, the construction of which is given in Example 7, was digested with restriction enzyme HindIII and then ligated to the ~0.87 kb HindIII restriction fragment of plasmid pBLcat to yield plasmid pLPC. A poly-GT element is inserted into the unique XhoI site of plasmid pLPC to yield plasmid pLPC(GT). A restriction site and function map of plasmid pLPC(GT) is presented in FIG. 8 of the accompanying drawings, and the construction of plasmids pLPC, pLPC(GT) are further described in Example 8. Alternatively, plasmid pLPC(GT) is prepared by digesting pL133 with HindIII and then ligating it with the ~0.93 kb HindIII fragment of pBL(GT).

Plasmids pLPC(GT) and pLPC, like plasmid pL133, comprise the enhancer, early and late promoters, T-antigen-binding sites, and origin of replication of SV40. Thus, use of plasmid pLPC or pLPC(GT) and derivatives thereof in any recombinant host cells is illustrative of the tandem enhancer expression method described herein. Plasmid pLPC or pLPC(GT) may serve as a useful starting material for many vectors described herein, including plasmids pSBL and pSBL(GT). Plasmids pSBL and pSBL(GT) may be constructed by deleting the protein C-encoding DNA on plasmids pLPC and pLPC(GT), respectively. This deletion merely requires excision of plasmid pLPC's or pLPC(GT)'s single BclI restriction fragment by digestion with BclI and self-ligation. The resulting plasmid pSBL or pSBL(GT) serves as a convenient expression vector for use in the tandem enhancer method described herein, because coding sequences of interest can be readily inserted at the sole remaining BclI site.

The SV40 regulatory elements present on plasmid pLPC or pLPC(GT) are situated closely together and difficult to delineate. The binding of T antigen to the T-antigen-binding sites, which is necessary for SV40 replication, is known to enhance transcription from the SV40 late promoter. Because the high level of T-antigen-driven replication of a plasmid that comprises the SV40 origin of replication is generally lethal to the host cell, neither plasmid pLPC nor plasmid pL133, for example, are stably maintained in the presence of SV40 T antigen.

Figure 9:
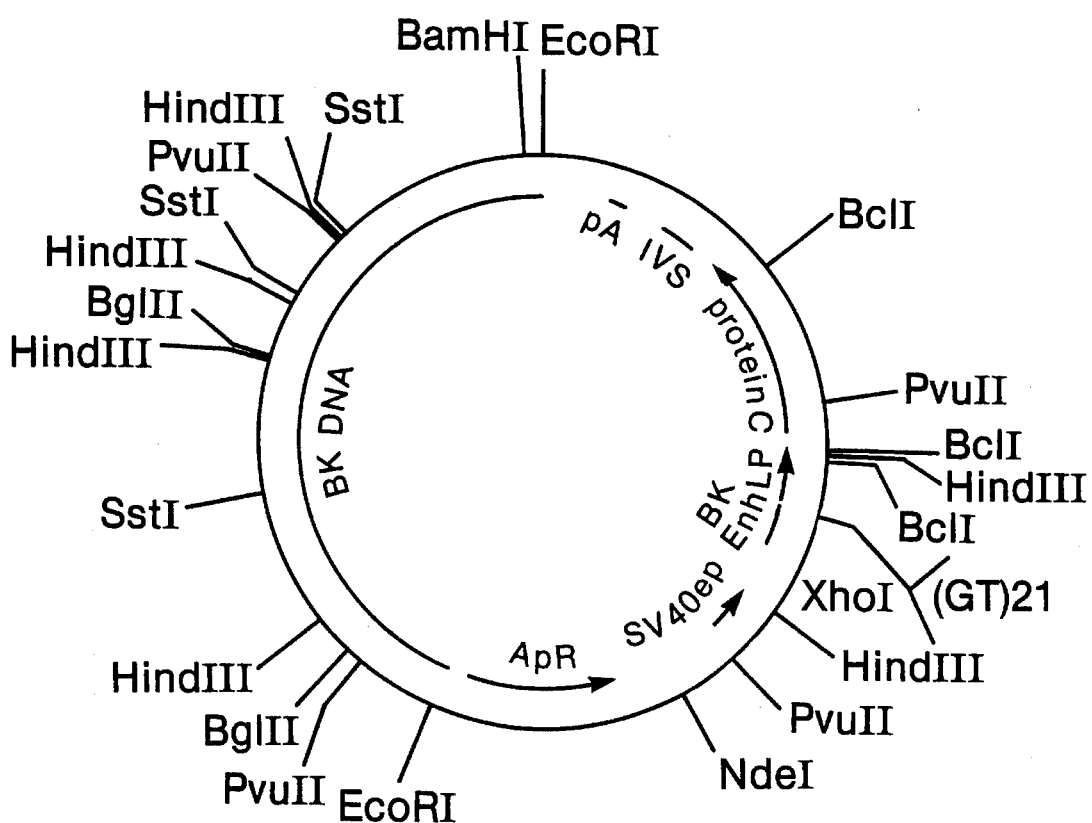
FIG. 9 is a restriction site and function map of plasmid pLPC4(GT).

The overall structure of the BK regulatory region is quite similar to that of SV40, for the BK enhancer, origin of replication, early and late promoters, and the BK analogue of the T-antigen-binding sites are all closely situated and each functional domain is not easily separated from the other. However, when grown in the present of BK T antigen, a plasmid that comprises the BK origin of replication and T-antigen-binding sites does not necessarily replicate to an extent that proves lethal and can be stably maintained as an episomal element in the host cell. In addition, the T-antigen-driven replication can be used to increase the copy number of a vector comprising the BK origin of replication so that when selective pressure is applied more copies of the plasmid integrate into the host cell's chromosomal DNA. Apparently due to the similar structure-function relationships between the BK and SV40 T antigens and their respective binding sites, BK replication is also stimulated by SV40 T antigen. To construct a derivative of plasmid pLPC that can exist as a stably-maintained element in a transformed eukaryotic cell, the entire BK genome, as an EcoRI-linearized restriction fragment, was inserted into the single EcoRI restriction site of plasmid pLPC. This insertion produced two plasmids, designated pLPC4 and pLPC5, which differ only with respect to the orientation of the BK EQoRI fragment. The construction of plasmids pLPC4 and pLPC5 is further described in Example 9A. A poly-GT element is inserted into the unique XhoI site of plasmids pLPC4 or pLPC5 to create plasmids pLPC4(GT) and pLPC-S(GT), respectively, as described in Example 9B. A restriction site and function map of plasmid pLPC4(GT) is presented in FIG. 9 of the accompanying drawings.

Episomal maintenance of a recombinant DNA expression vector is not always preferred over integration into the host cell chromosome. However, due to the absence of a selectable marker that functions in eukaryotic cells, the identification of stable, eukaryotic transformants of plasmid pLPC or pLPC(GT) is difficult, unless the plasmid is cotransformed with another plasmid that does comprise a selectable marker. Consequently, plasmid pLPC or plasmid pLPC(GT) may be modified to produce derivative plasmids that are selectable in eukaryotic host cells.

Figure 10:
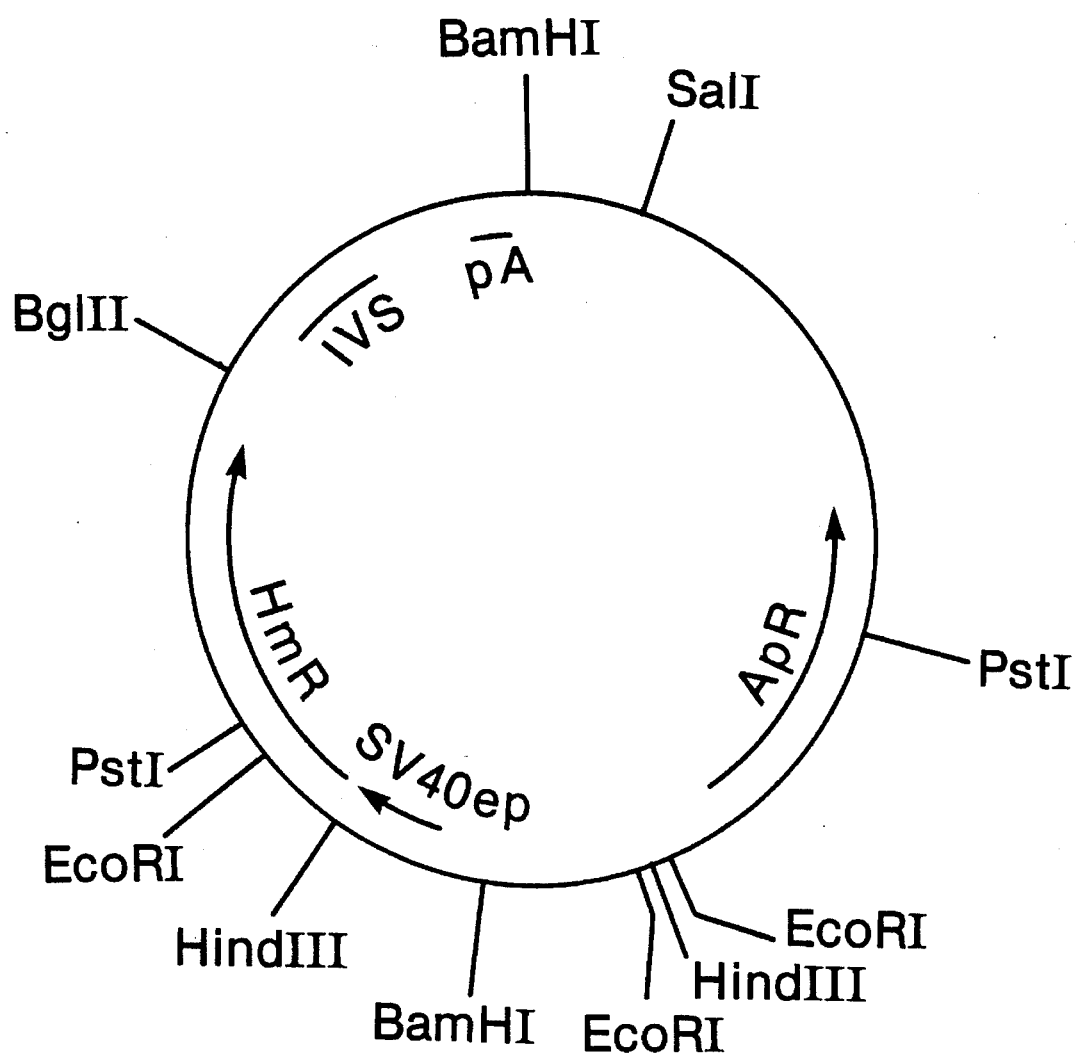
FIG. 10 is a restriction site and function map of plasmid pSV2hyg.
Figure 11:
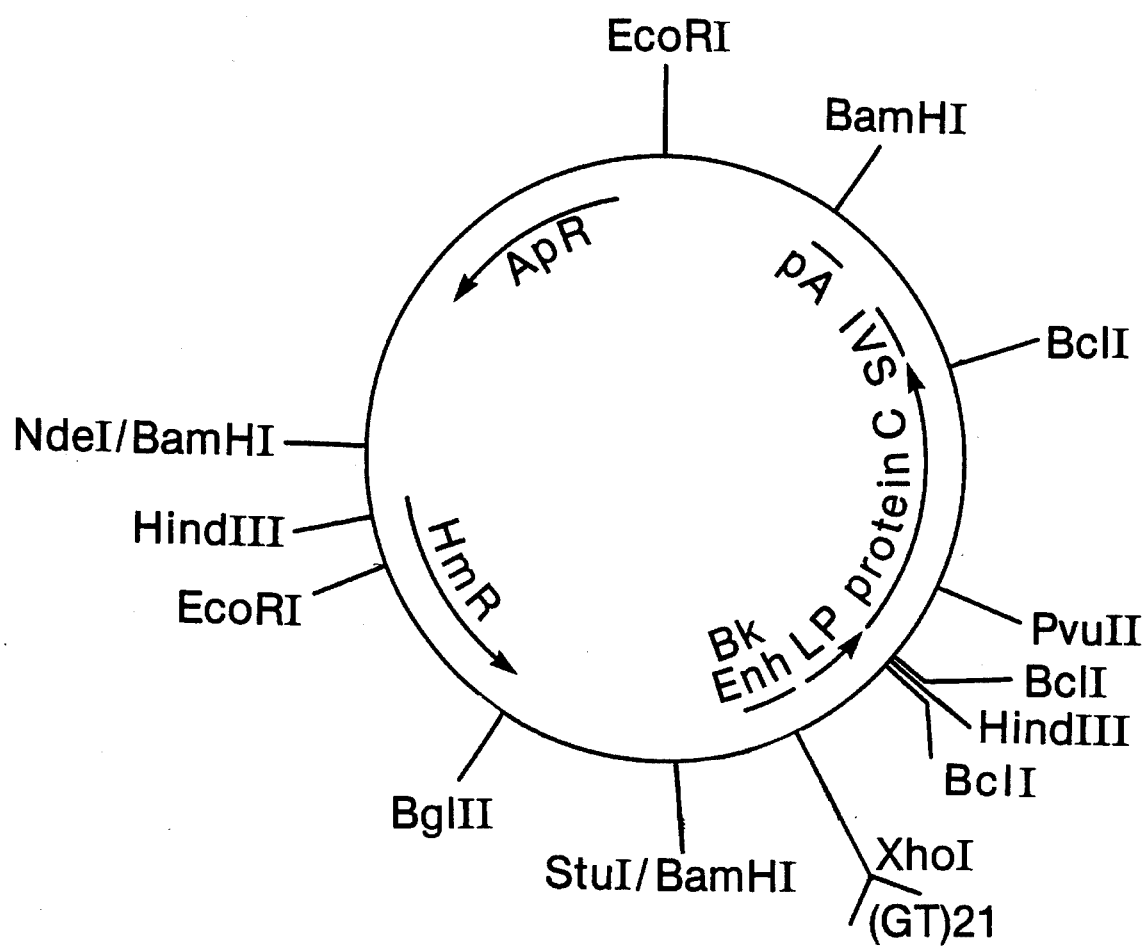
FIG. 11 is a restriction site and function map of plasmid pLPChyg1(GT).
Figure 12A:
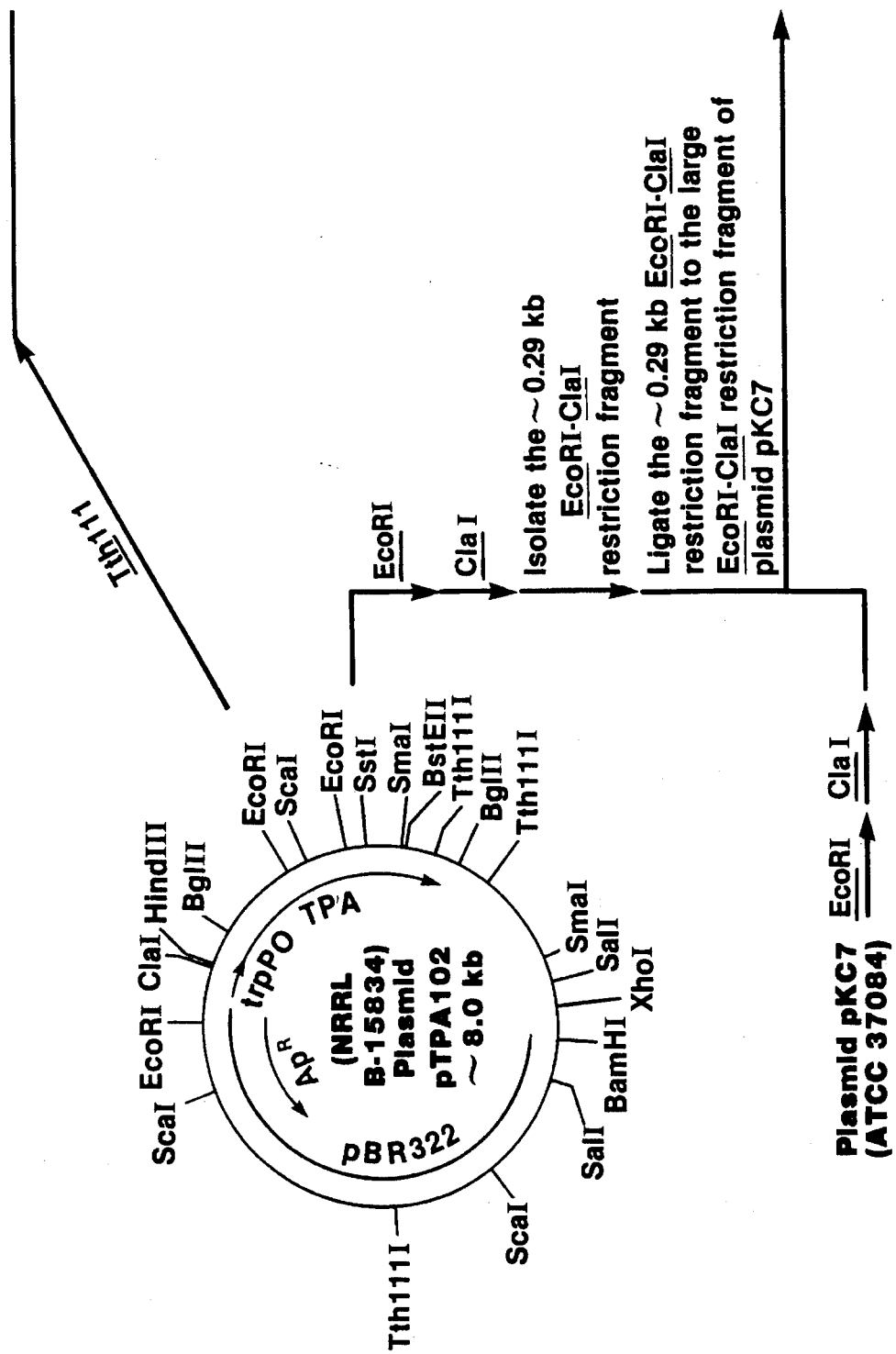
FIG. 12, Part 1.
Figure 12B:
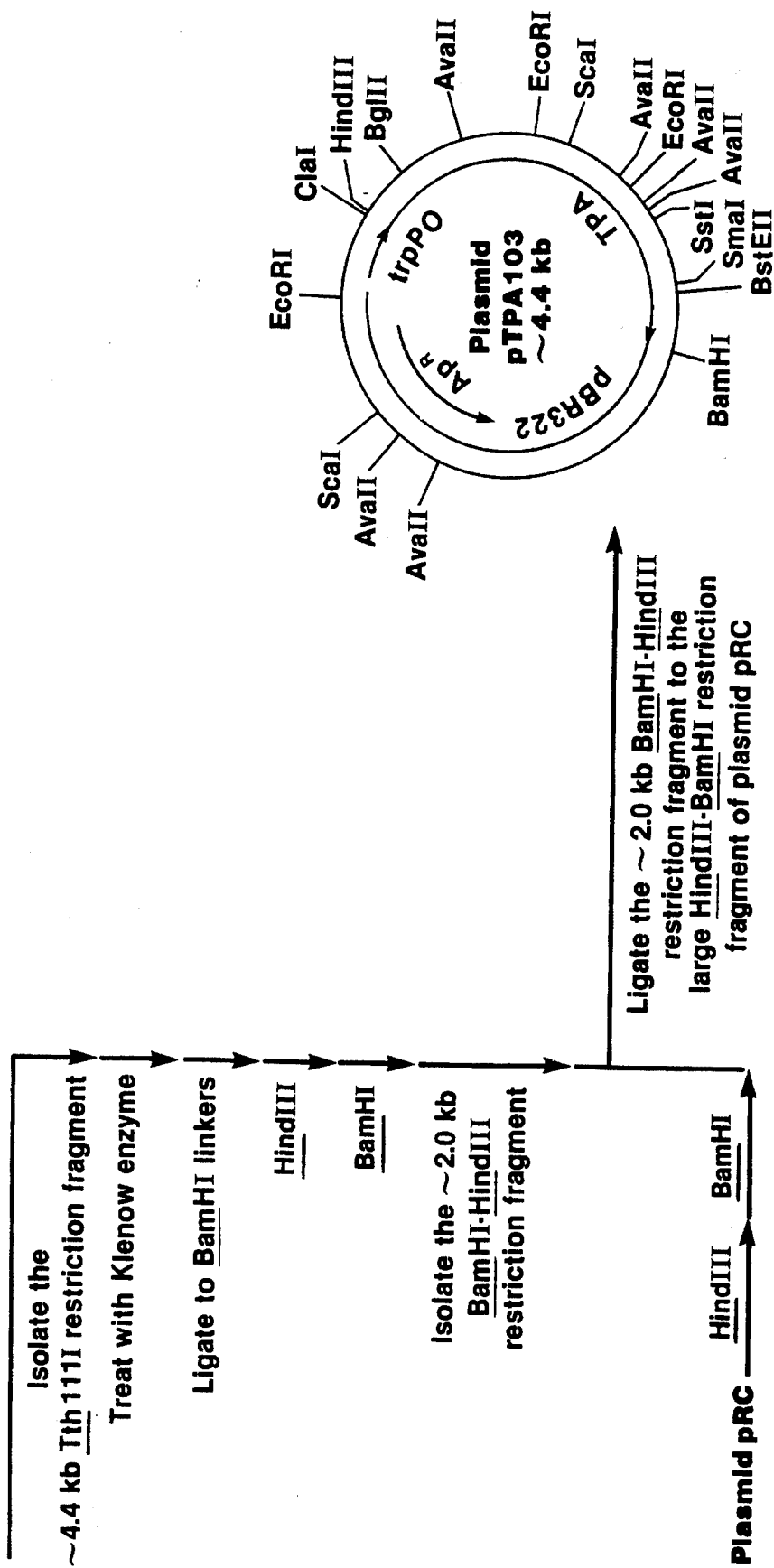
Figure 12C:
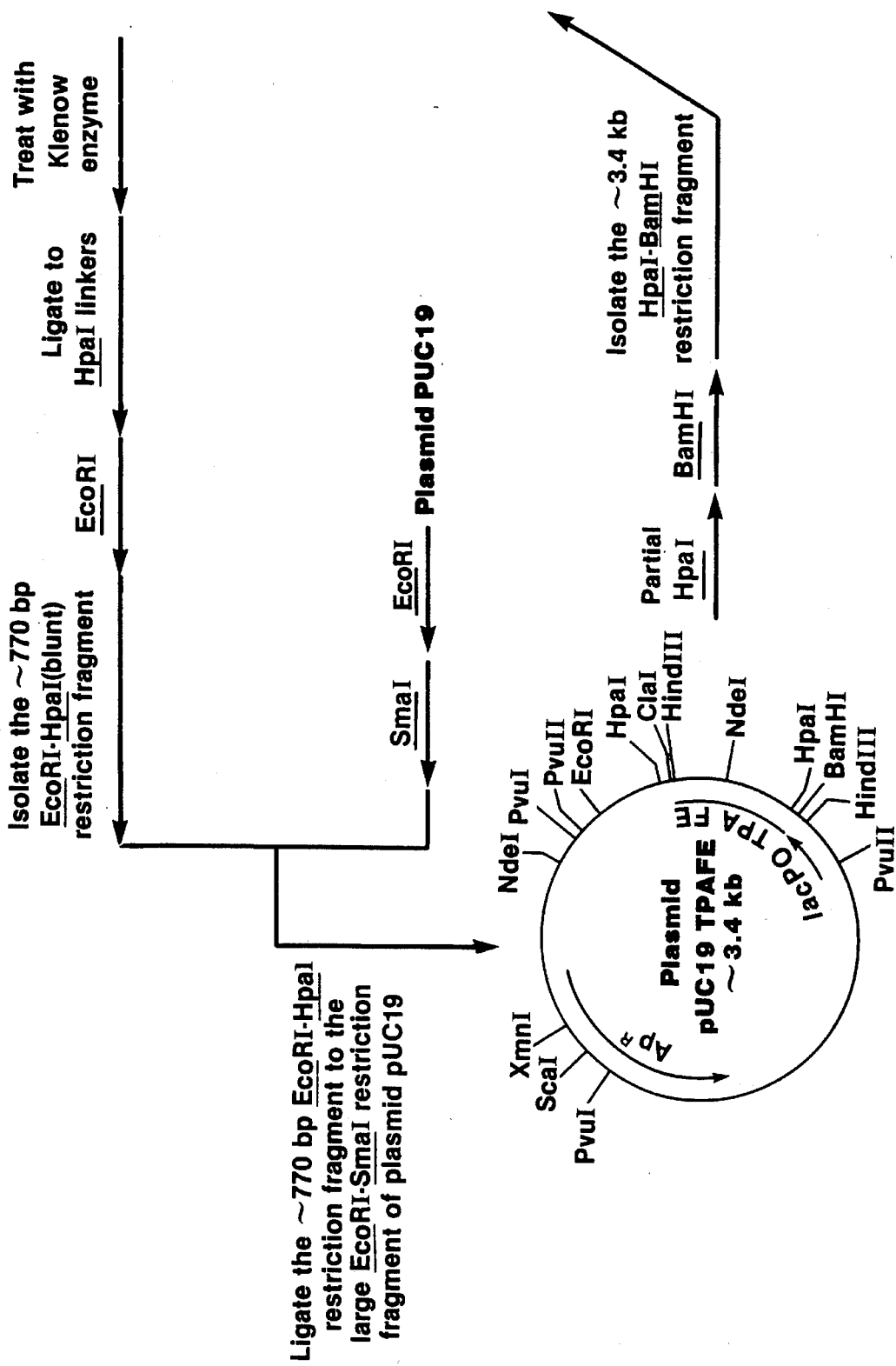
Figure 12D:
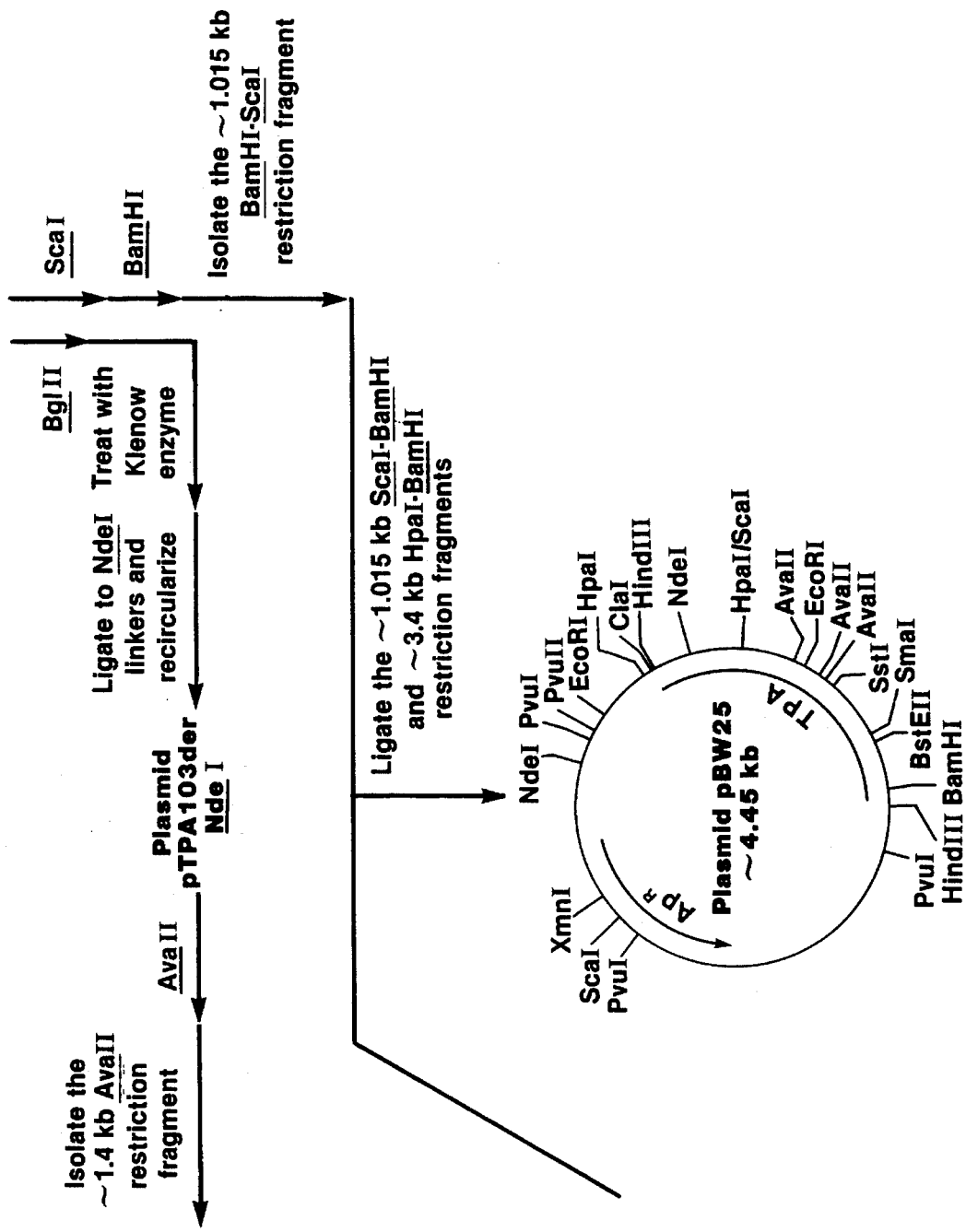
Figure 12E:
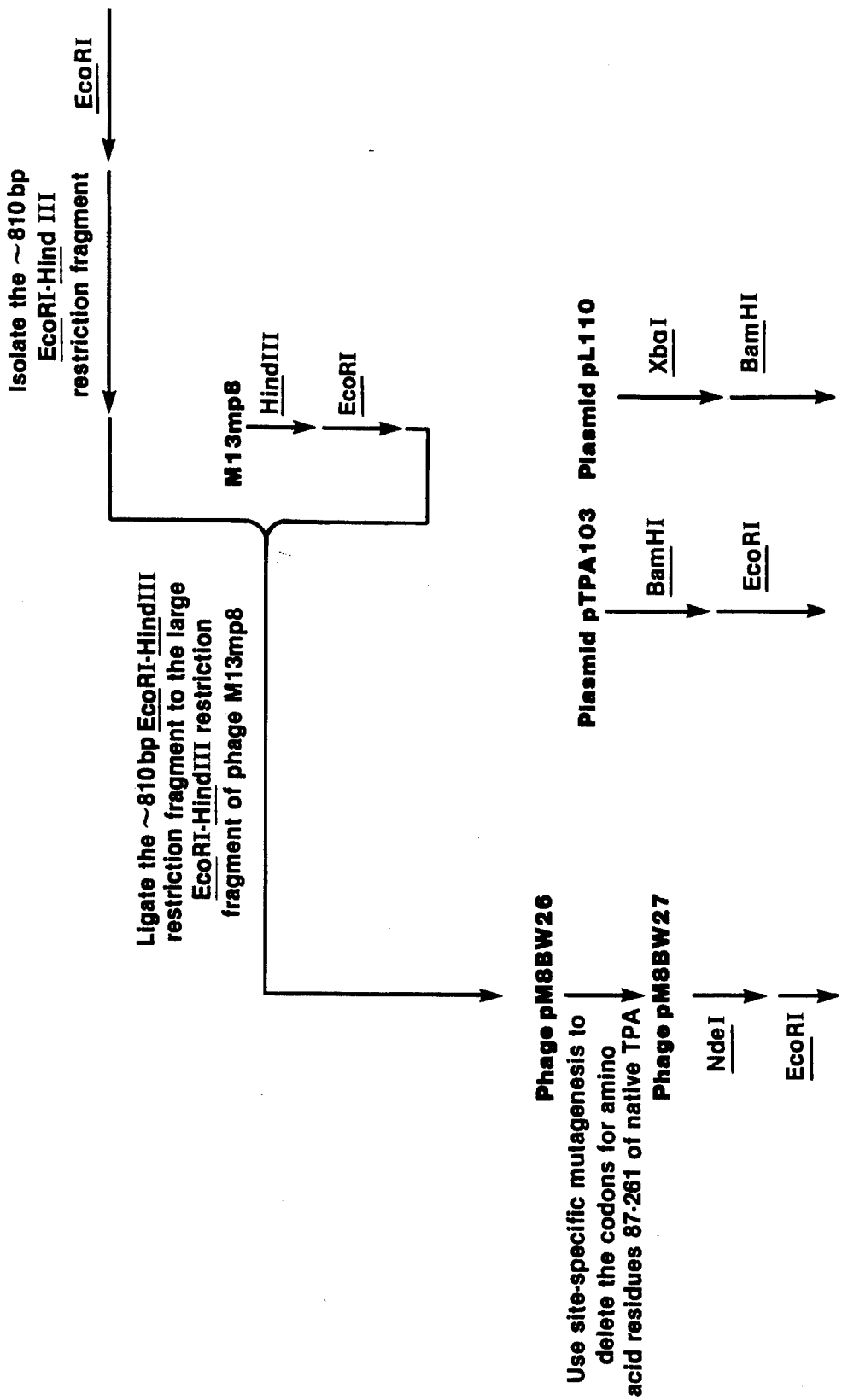
Figure 12F:
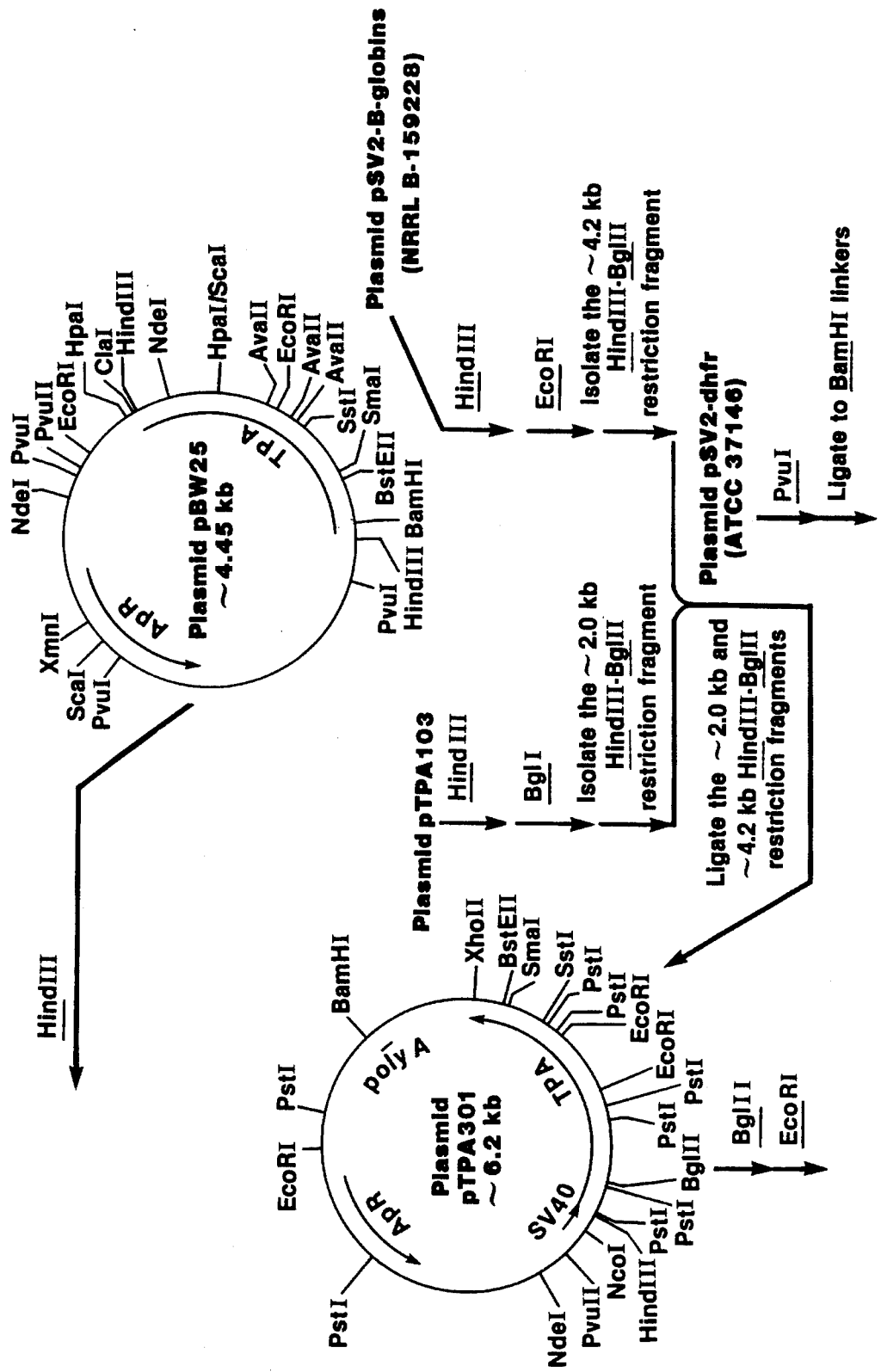
Figure 12G:
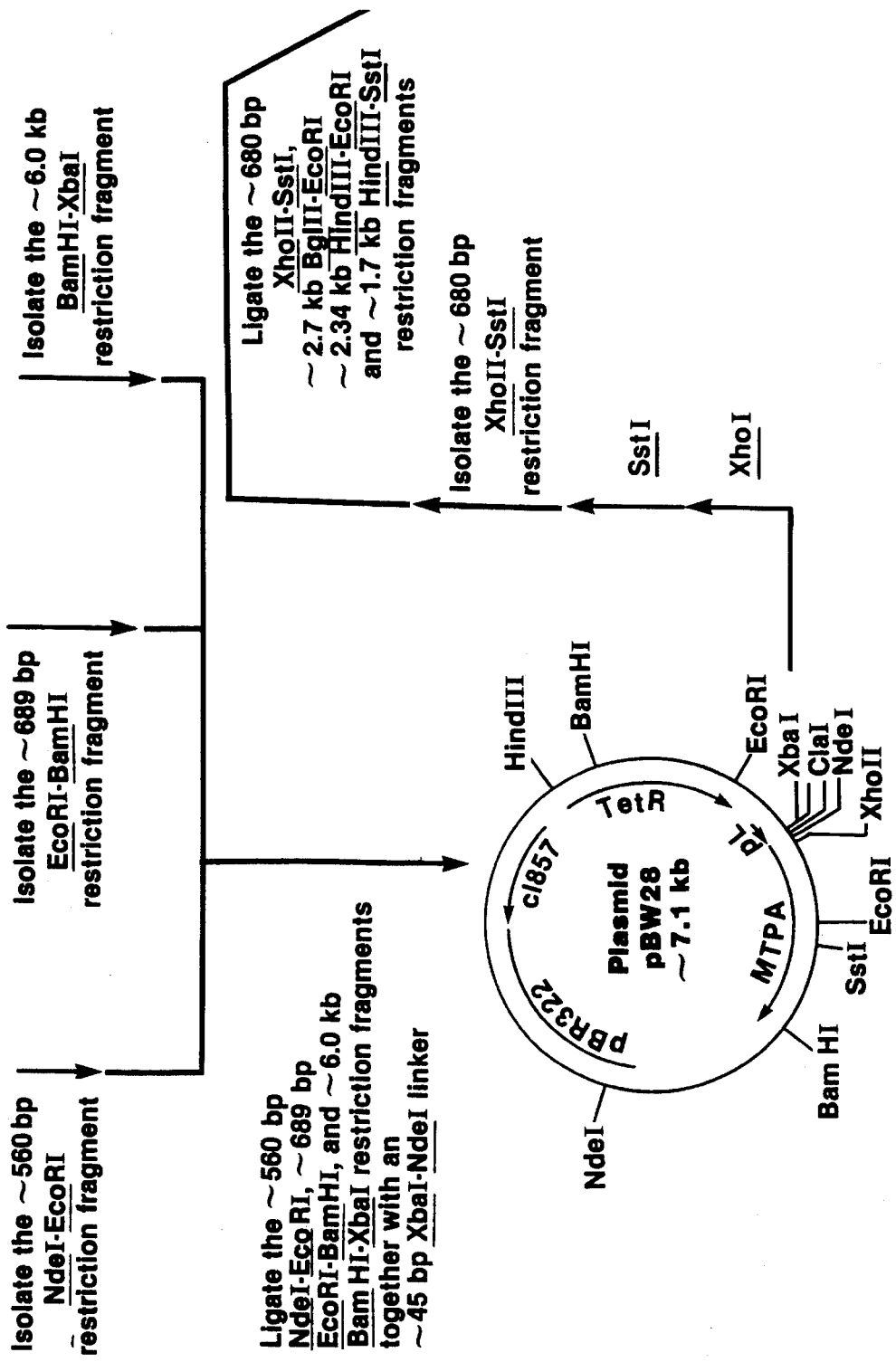
Figure 12H:
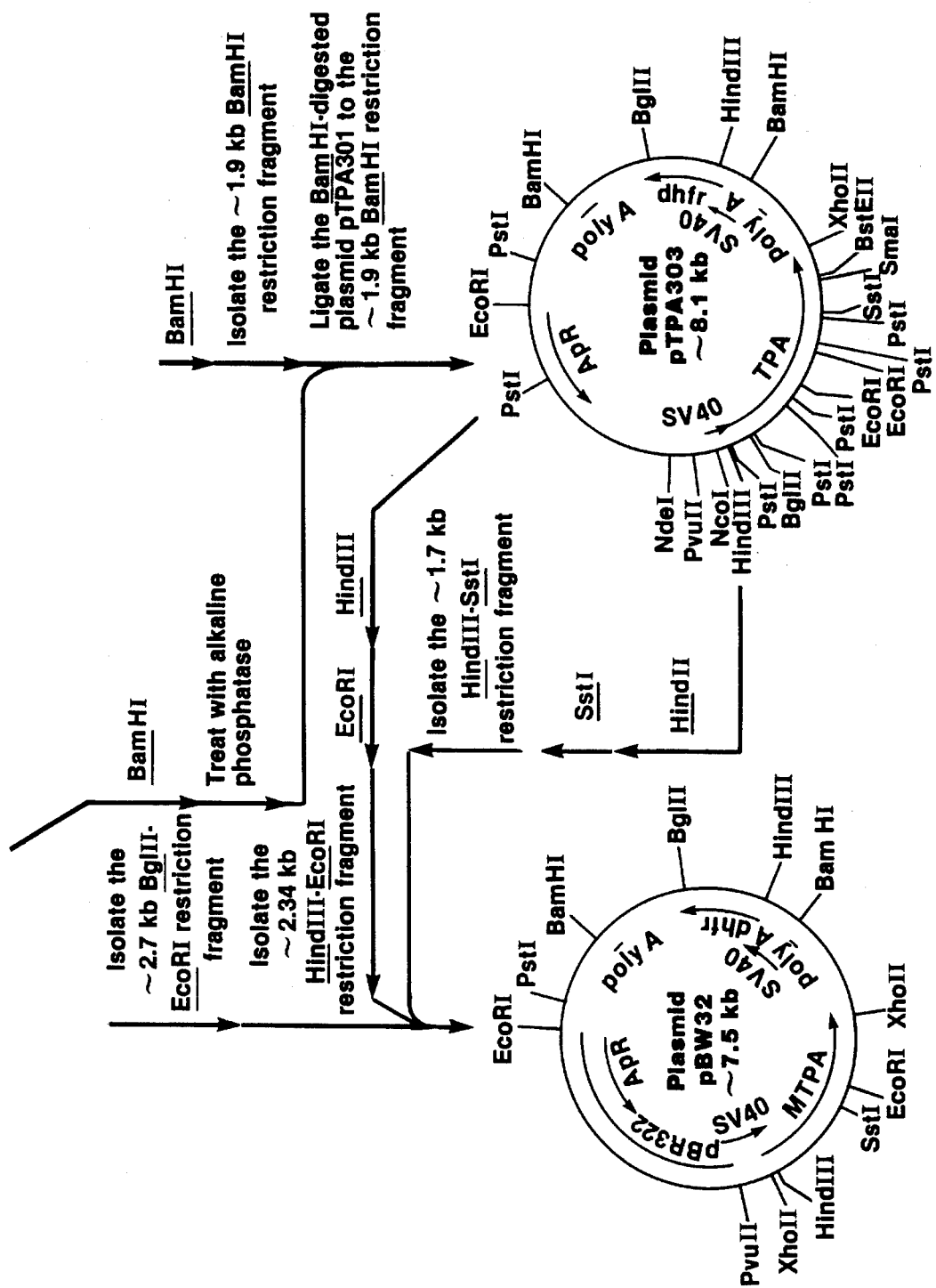
Figure 12I:
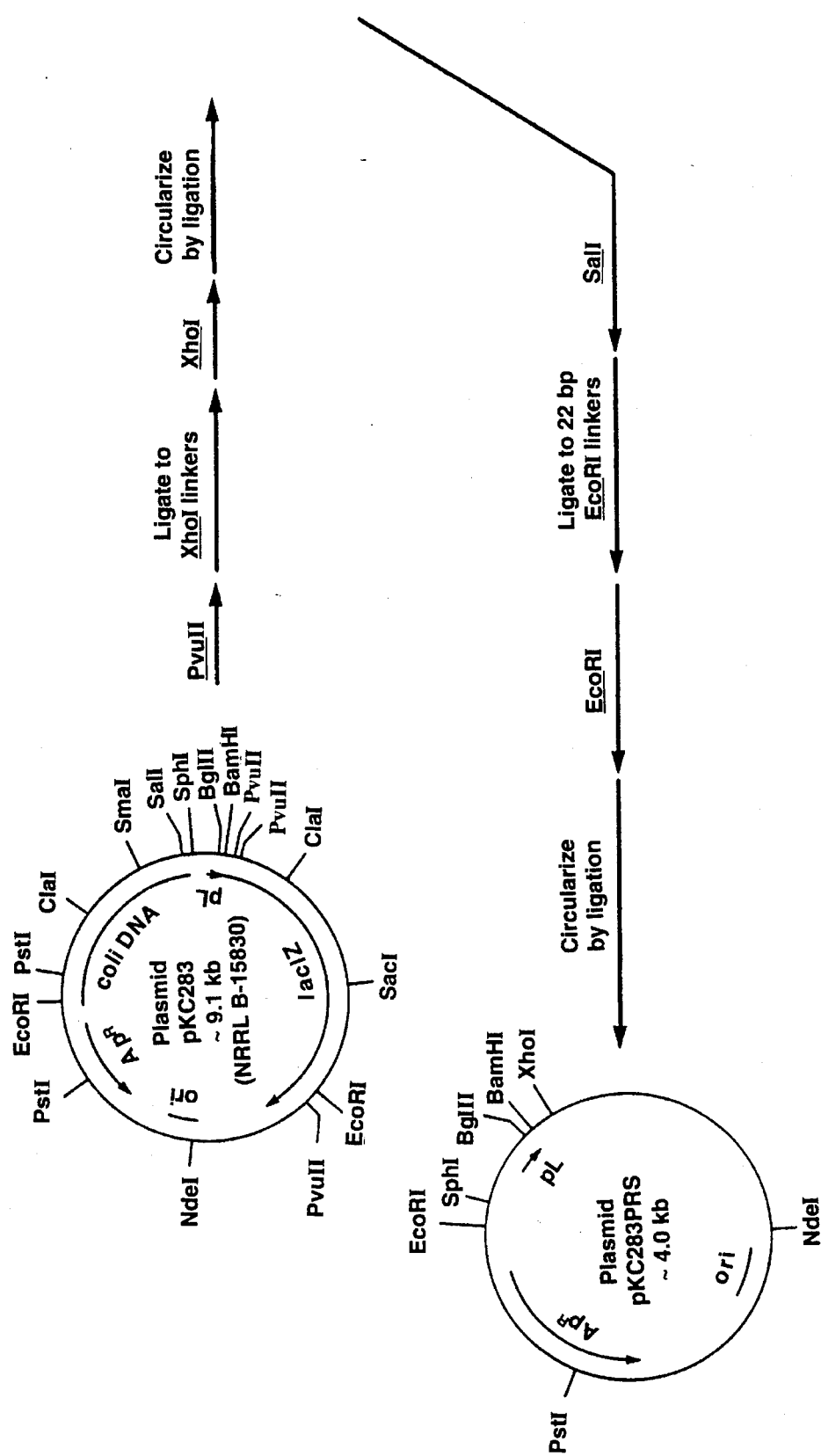
Figure 12J:
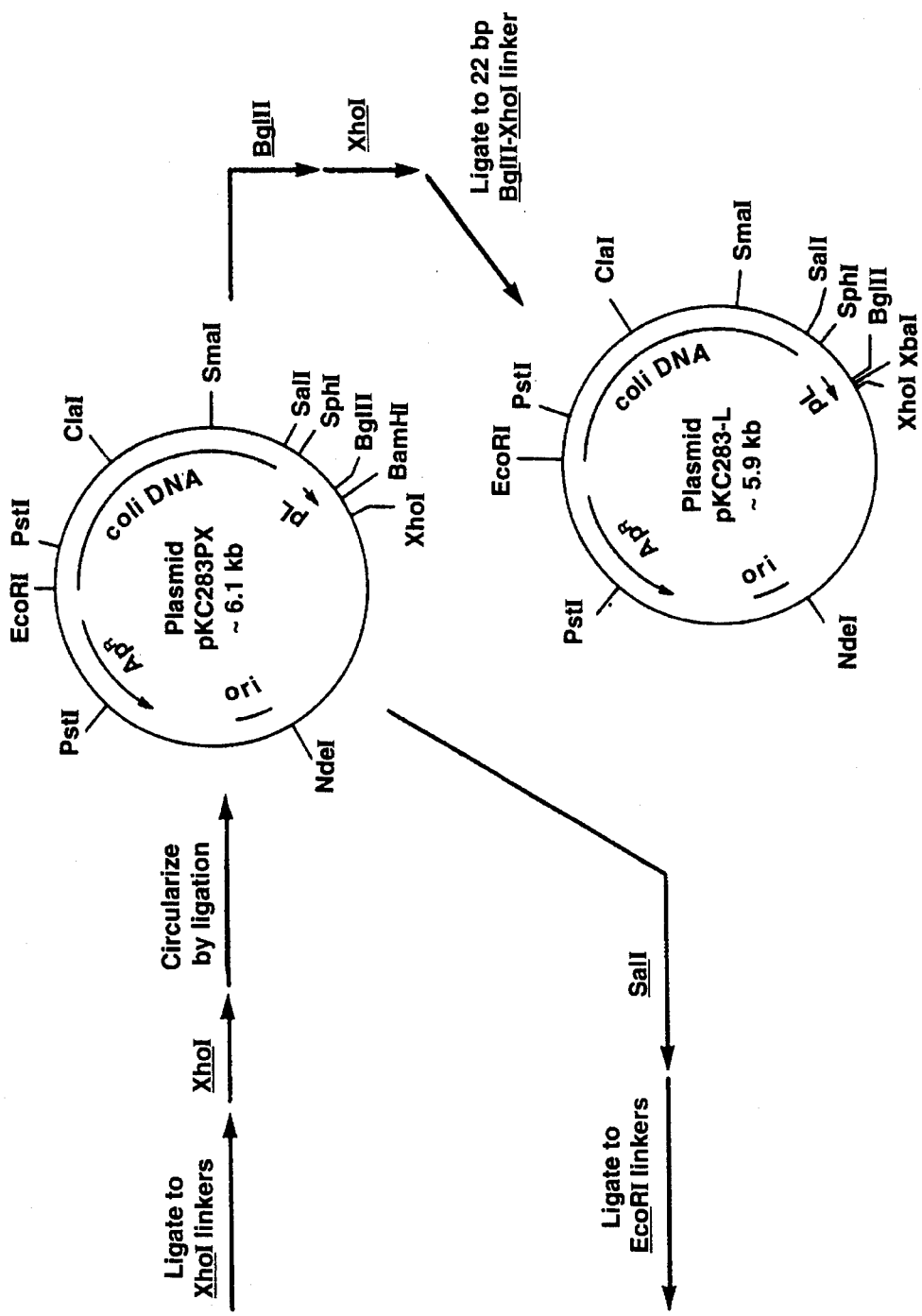
Figure 12K:
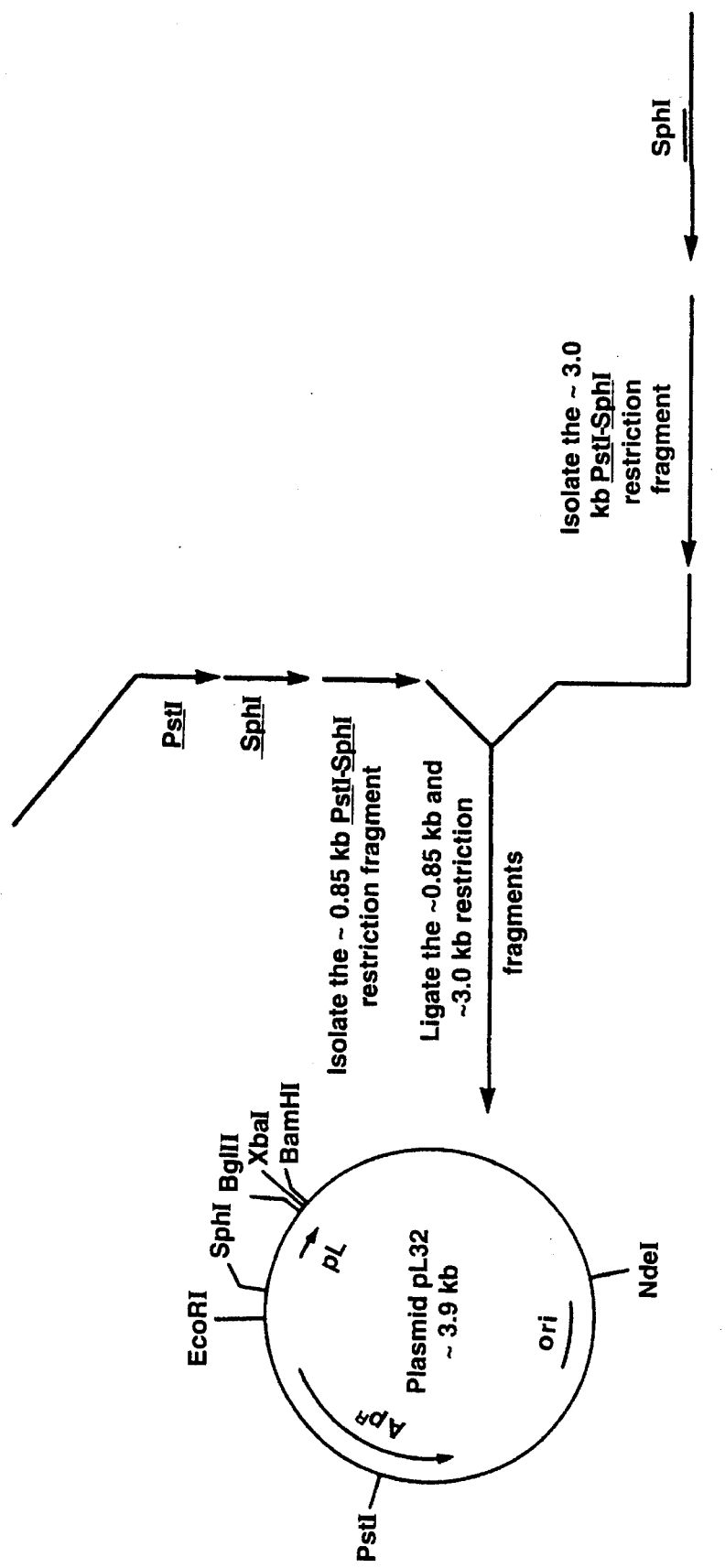
Figure 12L:
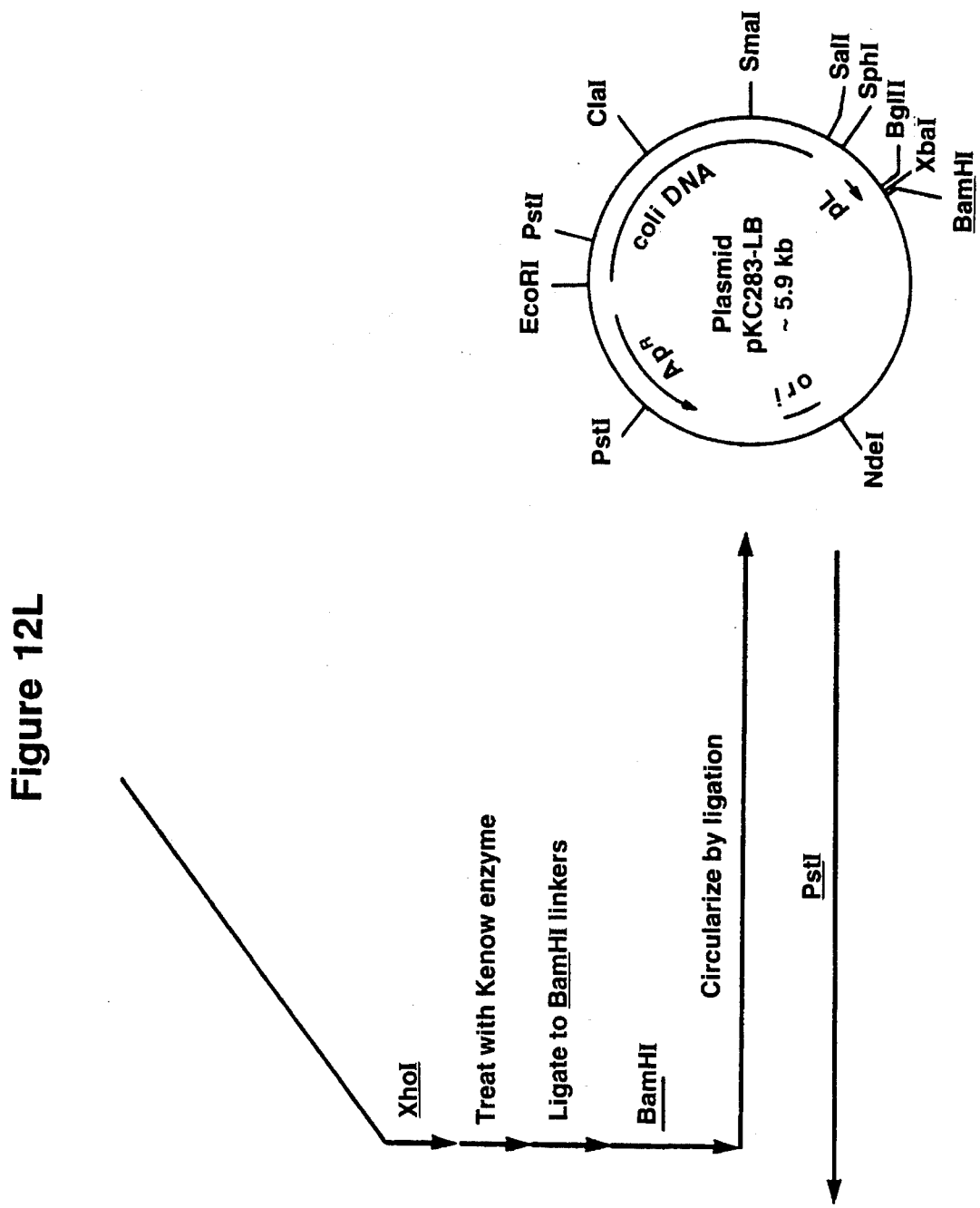
Figure 12M:
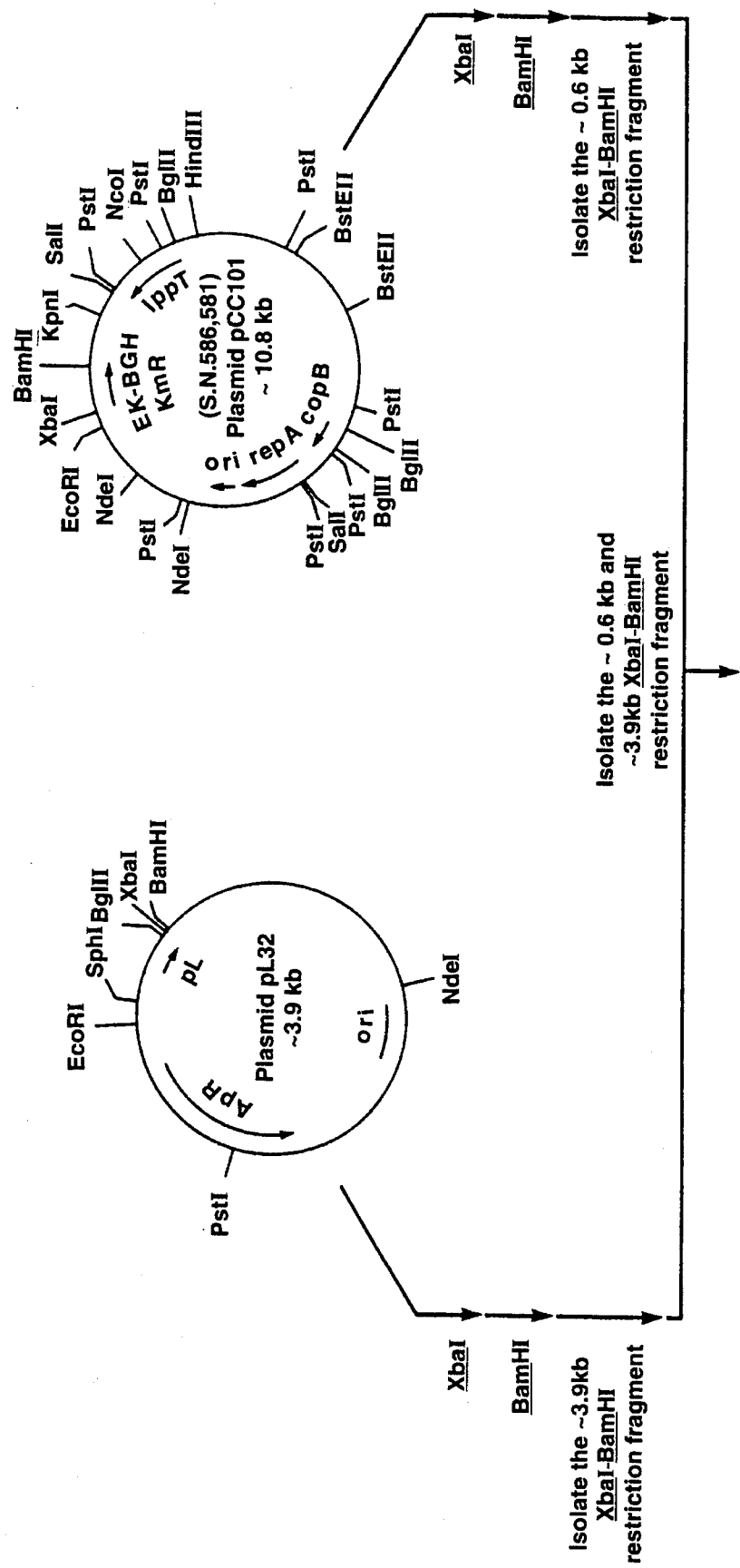
Figure 12N:
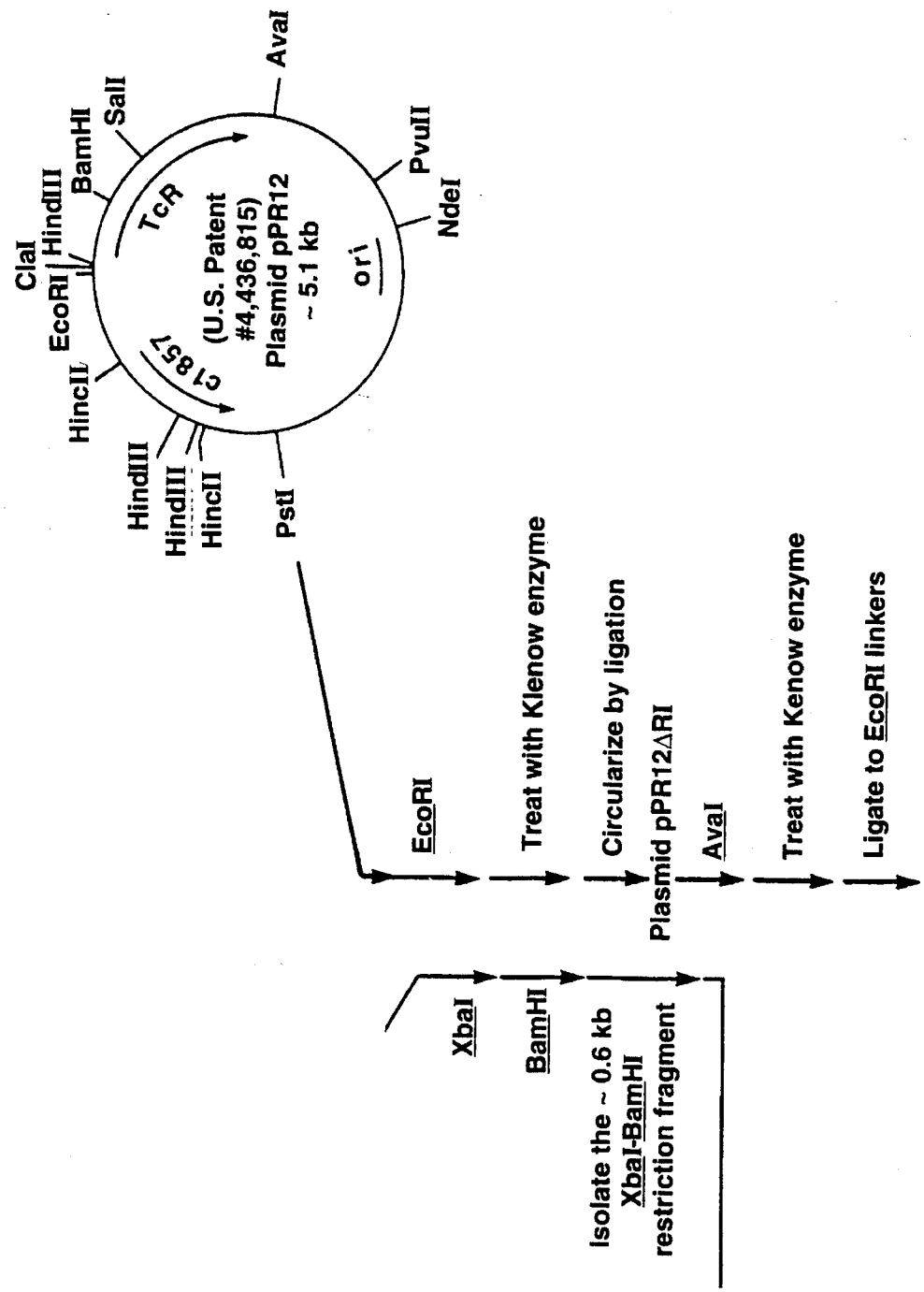
Figure 12O:
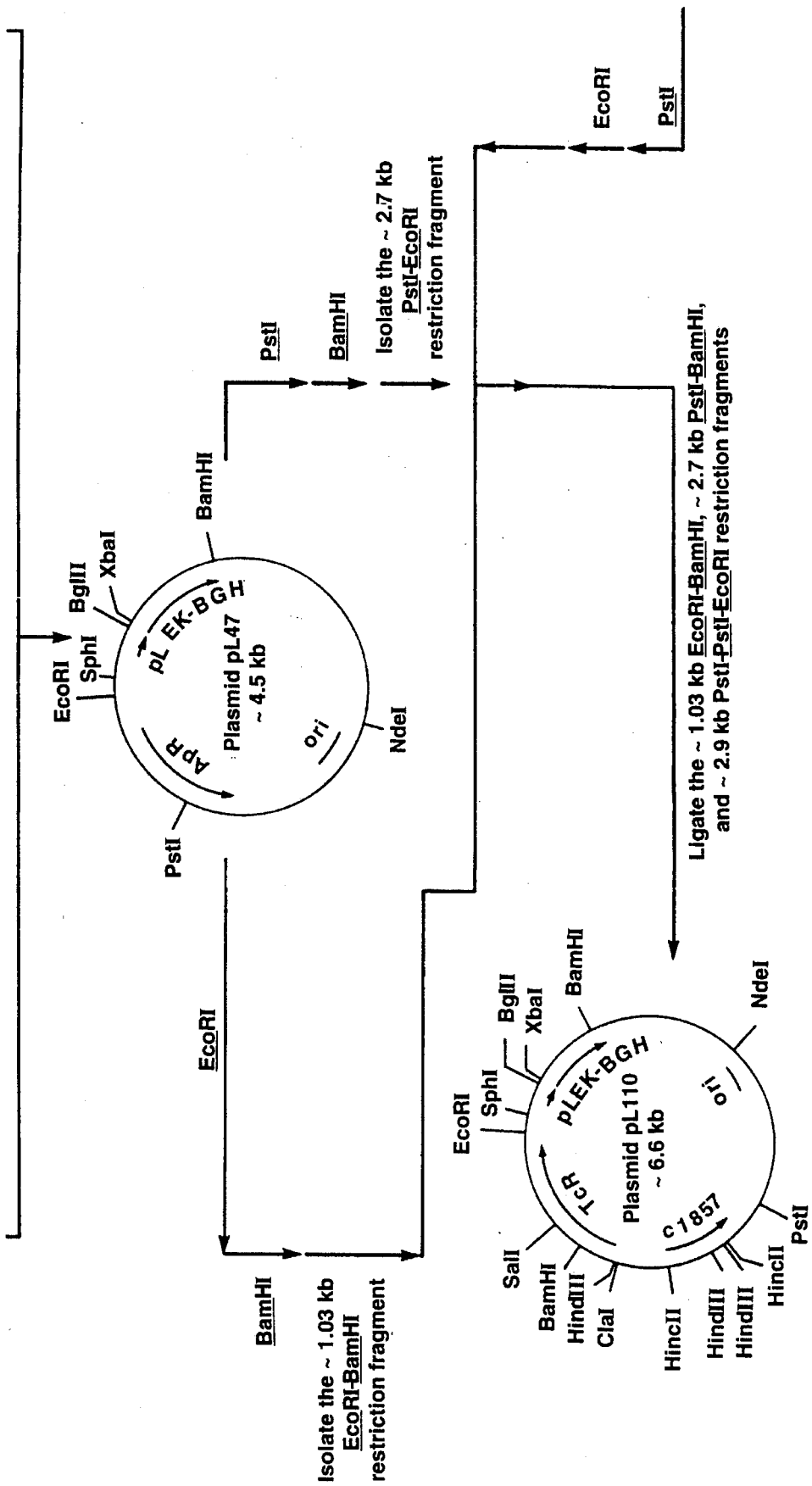
Figure 12P:
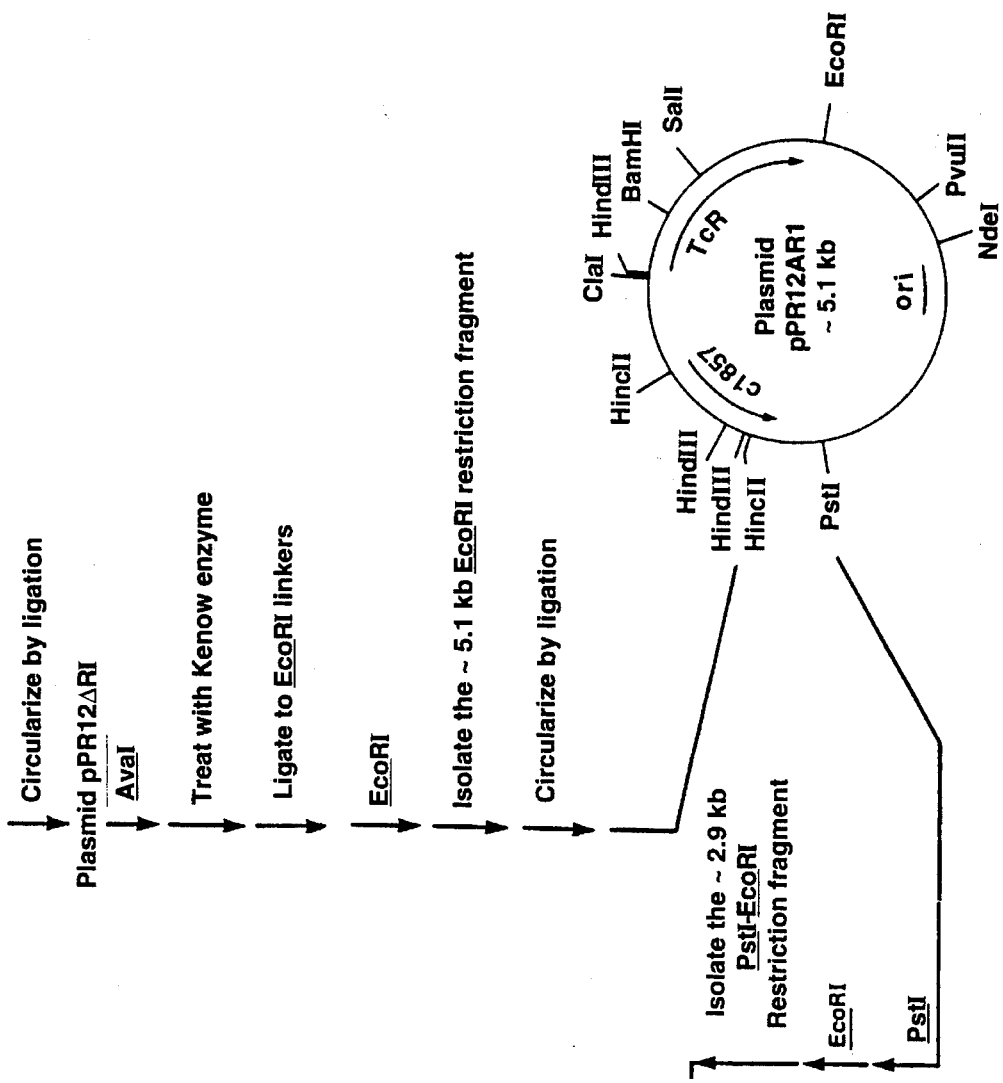

In the case of plasmid pLPC, this was done by ligating the plasmid to a portion of plasmid pSV2hyg; plasmid pSV2hyg is a plasmid that comprises a hygromycin resistance-conferring gene. A restriction site and function map of plasmid pSV2hyg, which can be obtained from the Northern Regional Research Laboratory (NRRL), Peoria, Ill. 61640, under the accession number NRRL B-18039, is presented in FIG. 10 of the accompanying drawings. Plasmid pSV2hyg was digested with restriction enzyme. BamHI, and the ~2.5 kb BamHI restriction fragment, which comprises the entire hygromycin resistance-conferring gene, was isolated, treated with Klenow enzyme (the large fragment produced upon subtilisin cleavage of $E.$ $coli$ DNA polymerase I), and then ligated to the Klenow-treated, ~5.82 kb NdeI-StuI restriction fragment of plasmid pLPC to yield plasmids pLPChyg1 and pLPChyg2. Plasmids pLPChyg1 and pLPChyg2 differ only with respect to the orientation of the hygromycin resistance-conferring fragment. The construction protocol for plasmids pLPChyg1 and pLPChyg2 is described in Example 10A. A poly-GT element is inserted into the unique XhoI site of plasmids pLPChyg1 and pLPChyg2, to create plasmids pLPChyg1(GT) and pLPChyg2(GT), respectively, as described in Example 10B. A restriction site and function map of plasmid pLPChyg1(GT) is presented in FIG. 11 of the accompanying drawings.

Human protein C expression plasmids similar to plasmids pLPChyg1 and pLPChyg2 containing the dihydrofolate reductase (dhfr) gene were constructed by inserting the dhfr gene-containing, Klenow-treated ~1.9 kb BamHI restriction fragment of plasmid pBW32 into the ~5.82 kb NdeI-StuI restriction fragment of plasmid pLPC. The resulting plasmids, designated as pLPCdhrf1 and pLPCdhrf2, differ only with respect to the orientation of the dhfr gene. A poly-GT element is inserted in the XhoI site of plasmids pLPCdhrf1 and pLPCdhrf2, to create plasmids pLPCdhrf1(GT) and pLPCdhrf2(GT), respectively. The construction of these plasmids is described in Example 12. Plasmid pLPChyg1 was further modified to introduce a dihydrofolate reductase (dhfr) gene. The dhfr gene is a selectable marker in dhfr-negative cells and can be used to increase the copy number of a DNA segment by exposing the host cell to increasing levels of methotrexate. The dhfr gene can be obtained from plasmid pBW32, a plasmid disclosed and claimed in U.S. patent application Ser. No. 769,298, filed Aug. 26, 1985, and incorporated herein by reference. A restriction site and function map of plasmid pBW32 is presented in FIG. 12 of the accompanying drawings. The construction protocol for plasmid pBW32 is described in Example 11.

Figure 13:
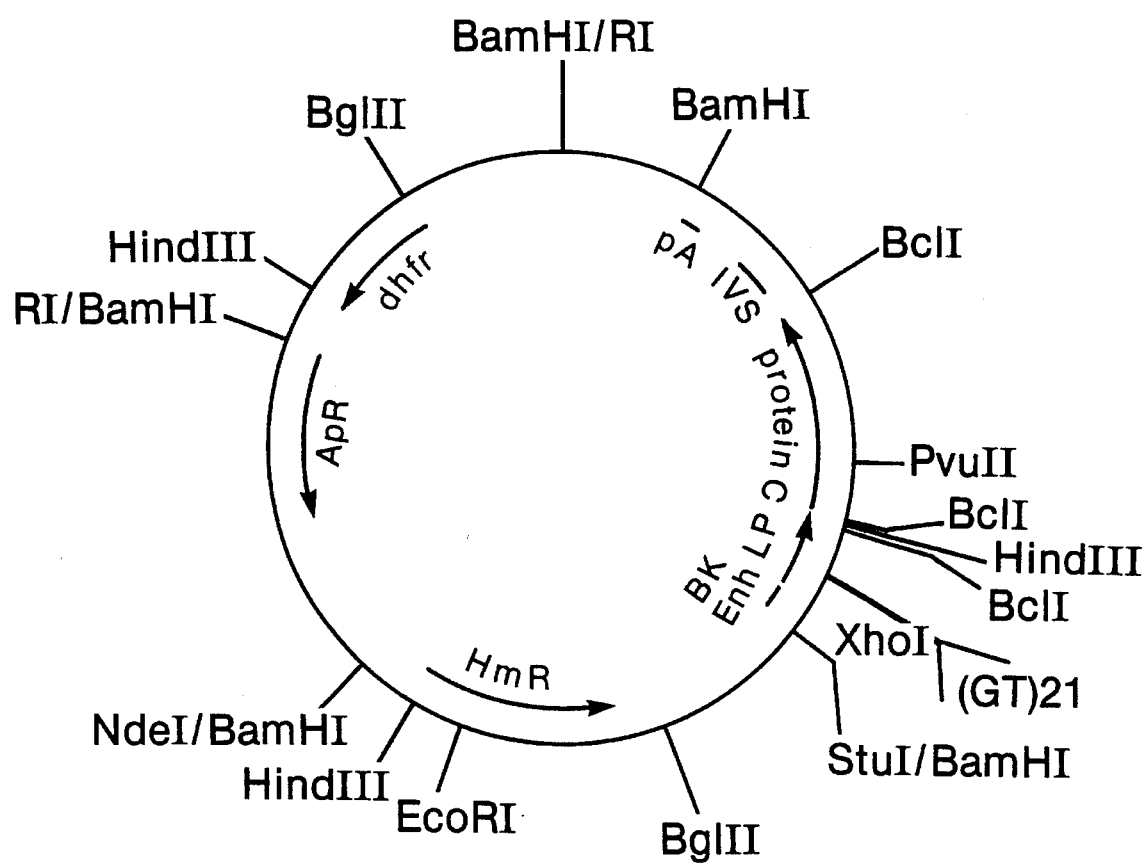
FIG. 13 is a restriction site and function map of plasmid pLPChd1(GT).

The dhfr gene-containing, ~1.9 kb BamHI restriction fragment of plasmid pBW32 was isolated, treated with Klenow enzyme, and inserted into partially-EcoRI-digested plasmid pLPChyg1 to yield plasmids pLPChd1 and pLPChd2. Plasmid pLPChyg1 contains two EcoRI restriction enzyme recognition sites, one in the hygromycin resistanceconferring gene and one in the plasmid pBR322-derived sequences. The fragment comprising the dhfr gene was inserted into the EcoRI site located in the pBR322-derived sequences of plasmid pLPCyg1 to yield plasmids pLPChd1 and pLPChd2. The construction of plasmids pLPChd1 and pLPChd2, which differ only with respect to the orientation of the dhfr gene-containing DNA segment, is described in Example 12A. A poly-GT element is inserted in the unique XhQI site of plasmids pLPChd1 and pLPChd2 to create plasmids pLPChd1(GT) and pLPChd2(GT), respectively, as described in Example 12B. A restriction site and function map of plasmid pLPChd1(GT) is presented in FIG. 13 of the accompanying drawings.

Figure 14:
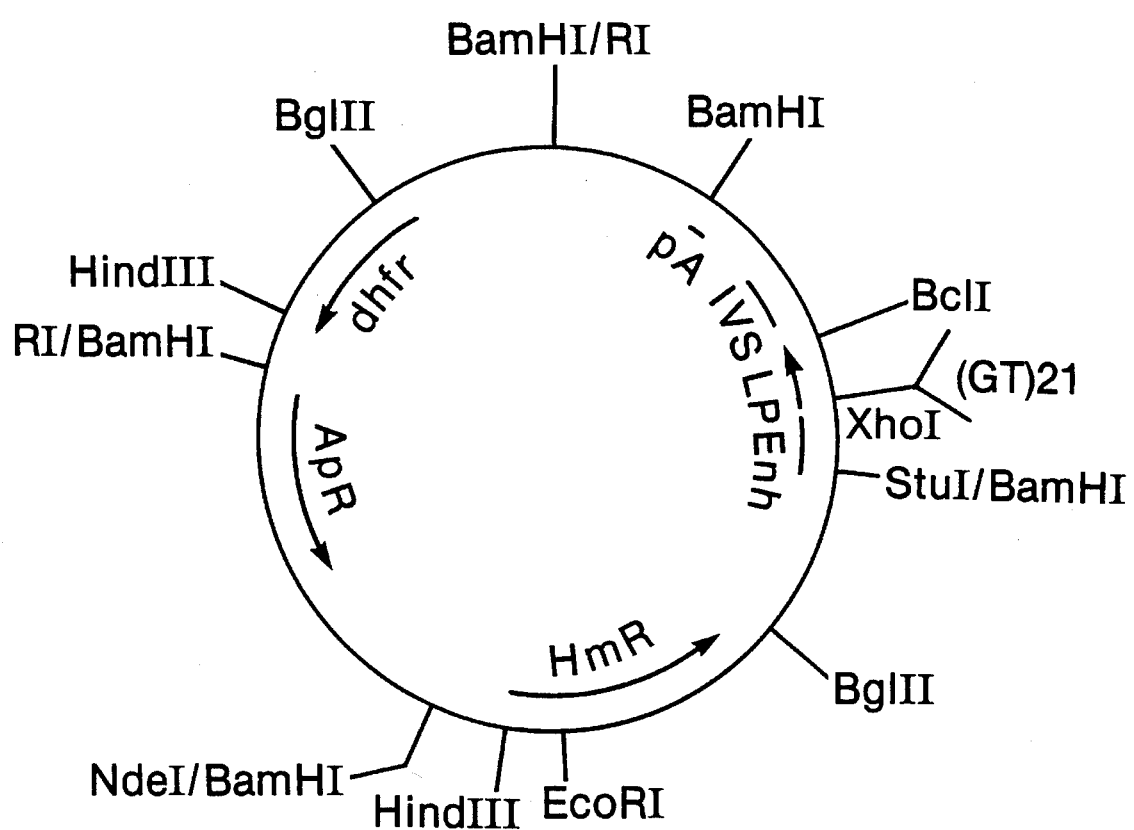
FIG. 14 is a restriction site and function map of plasmid phd(GT).

Plasmid pLPChd1 was modified to form plasmid phd, a plasmid that contains both the BK enhancer adenovirus late promoter cassette and also the hygromycin resistance-conferring and dhfr genes. To construct plasmid phd, plasmid pLPChd1 was prepared from dam E. coil host cells, digested with restriction enzyme BclI, and recircularized, thus deleting the human protein Cencoding DNA. Plasmid phd contains a single BclI restriction enzyme recognition site, which is conveniently positioned for the insertion of any sequence desired to be expressed from the BK enhancer-adenovirus late promoter as described herein. The construction protocol for plasmid phd is described in Example 13A. A poly-GT element is inserted into the XhoI site of plasmid phd to create plasmid phd(GT), as further described in Example 13B. The single BclI restriction enzyme recognition site of plasmid phd(GT) is conveniently positioned for the insertion of any sequence desired to be expressed from the BK enhancer-poly-GT-adenovirus late promoter of the present invention. A restriction site and function map of plasmid phd(GT) is presented in FIG. 14 of the accompanying drawings.

Figure 15:
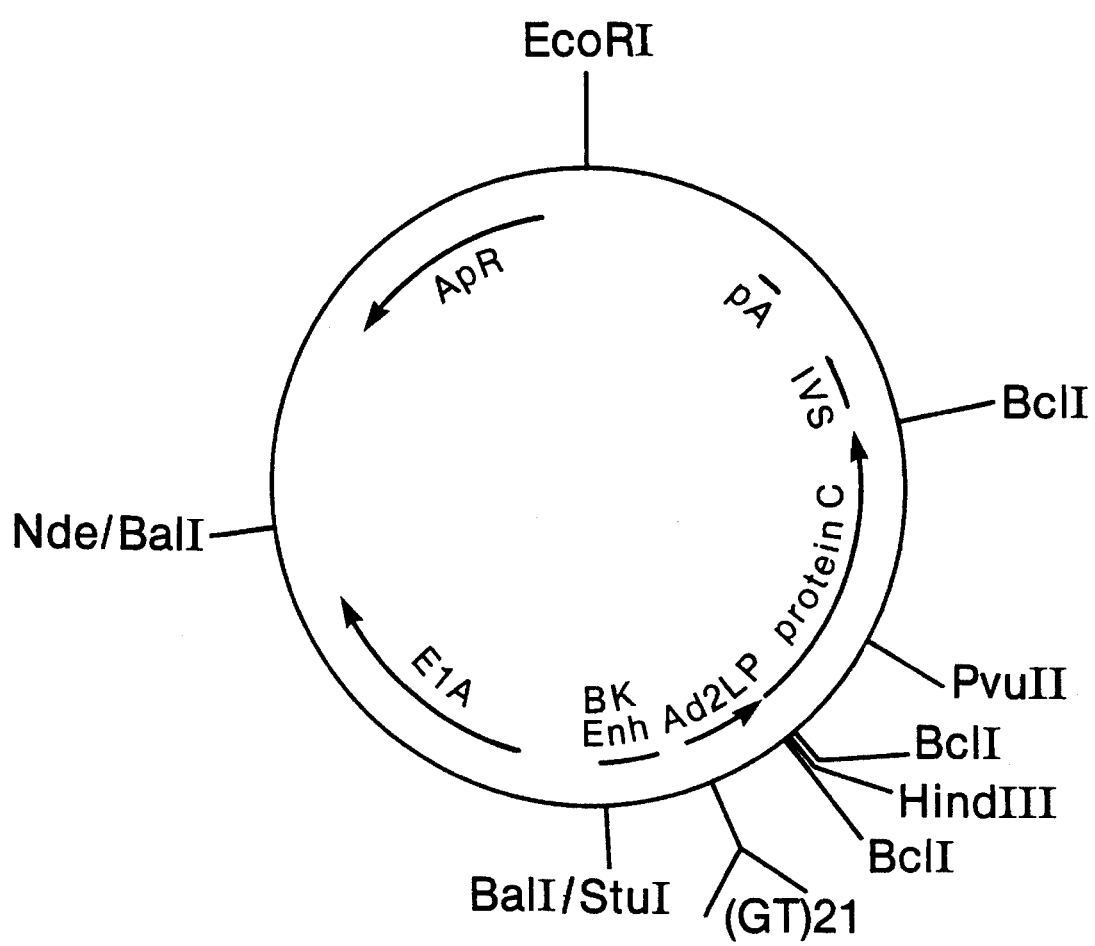
FIG. 15 is a restriction site and function map of plasmid pLPCE1A(GT).
Figure 16:
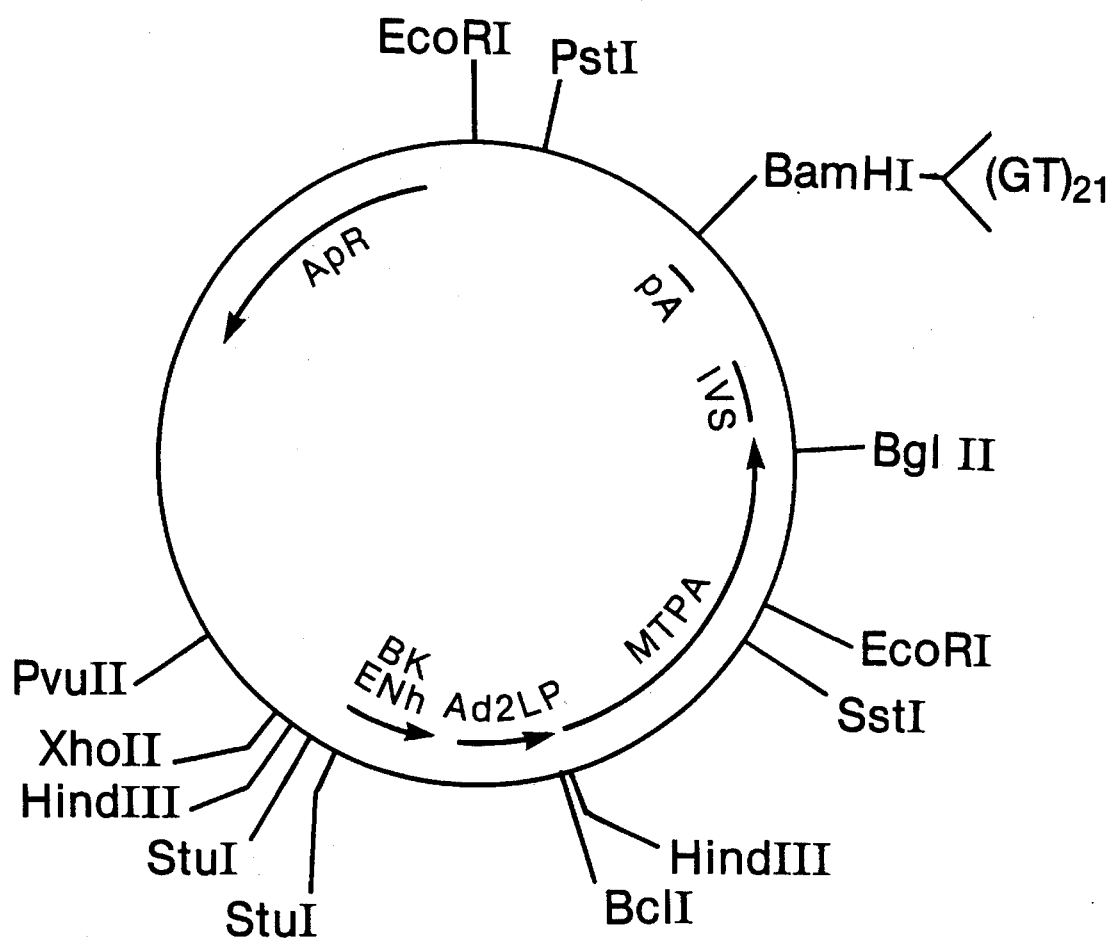
FIG. 16 is a restriction site and function map of plasmid pBLT(GT).

Other expression vectors that drive expression of human protein C are plasmids pLPCE1A and pLPCE1A(GT). Plasmids pLPCE1A and pLPCE1A(GT) contain the E1A gene of human adenovirus type 2, the gene product of which, as described above, increases the activity of the BK enhancer, and, as described in the present invention, activates the enhancer activity of the poly-GT element. Thus, transcription from a promoter in tandem with the BK enhancer and the poly-GT element increases in the presence of the E1A gene product. Plasmid pLPCE1A was constructed by ligating the E1A gene-containing, ~1.8 kb BaIl restriction fragment of human adenovirus-type-2 DNA with the ~5.82 kb el-stI restriction fragment of plasmid pLPC. The construction protocol for plasmid pLPCE1A is described in Example 14A. A poly-GT element is inserted into the unique XhoI site of plasmid pLPCE1A to created plasmid pLPCE1A(GT), as further described in Example 14B. A restriction site and function map of plasmid pLPCE1A(GT) is presented in FIG. 15 of the accompanying drawings. A variety of expression vectors of the present invention utilize the poly-GT—BK enhancer—adenovirus late promoter cassette or the BK enhancer—adenovirus late promoter cassette to drive expression of tissue plasminogen activator (TPA) or modified TPA (MTPA). To construct vectors with TPA or MTPA, plasmid pBW32 (FIG. 12) was digested with restriction enzyme BamHI, and the resultant ~5.6 kb fragment was recircularized to yield plasmid pBW32del. Plasmid pBW32del, which encodes modified TPA and contains only one HindIII restriction site, was digested with HindIII and then ligated with the ~0.65 kb HindIII restriction fragment of plasmid pBal8cat to yield plasmid pBLT. Plasmid pBal8cat comprises an improved BK enhancer-adenovirus late promoter cassette and is described in Example 18. A poly-GT element is inserted into the unique BamHI site of plasmid pBLT to create plasmids pBLT(GT). A restriction site and function map of plasmid pBLT(GT) is presented in FIG. 16 of the accompanying drawings, and the construction protocol for plasmids pBLT and pBLT(GT) is described in Example 15.

Figure 17:
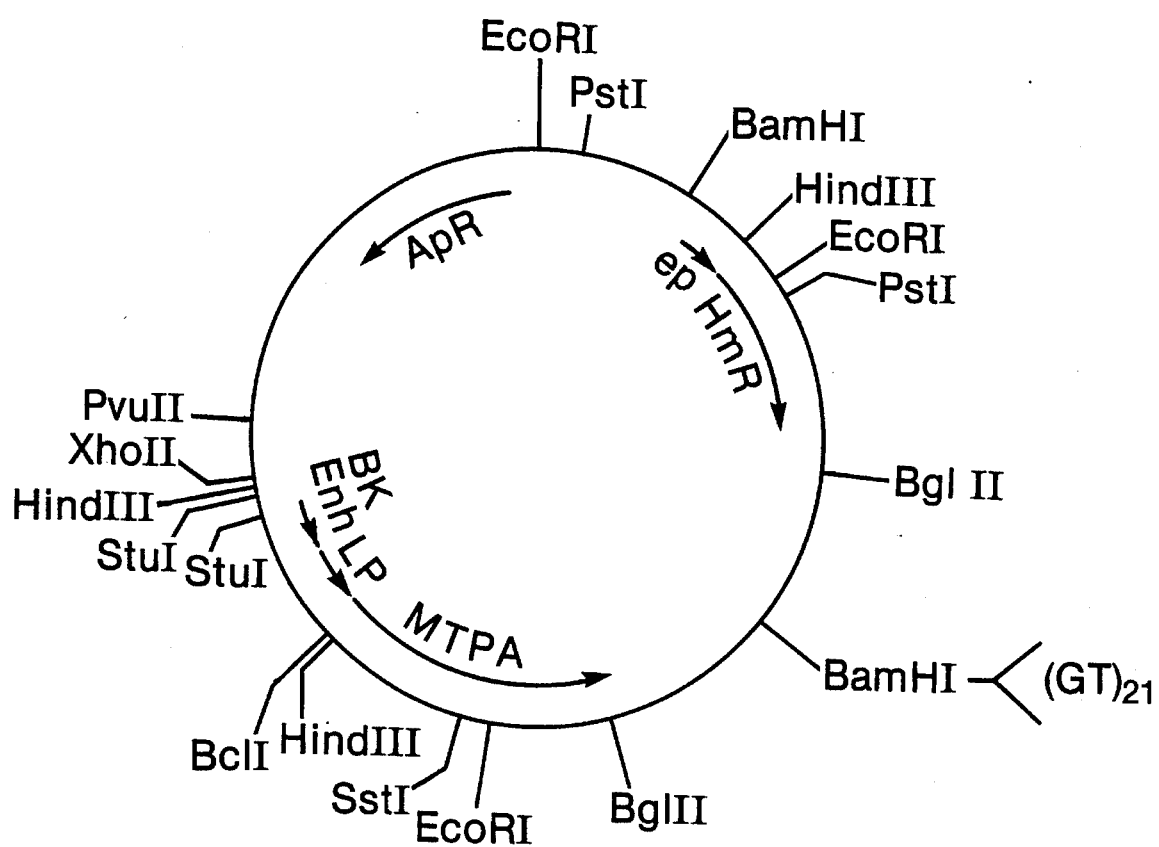
FIG. 17 is a restriction site and function map of plasmid pBLThyg1(GT).
Figure 18:
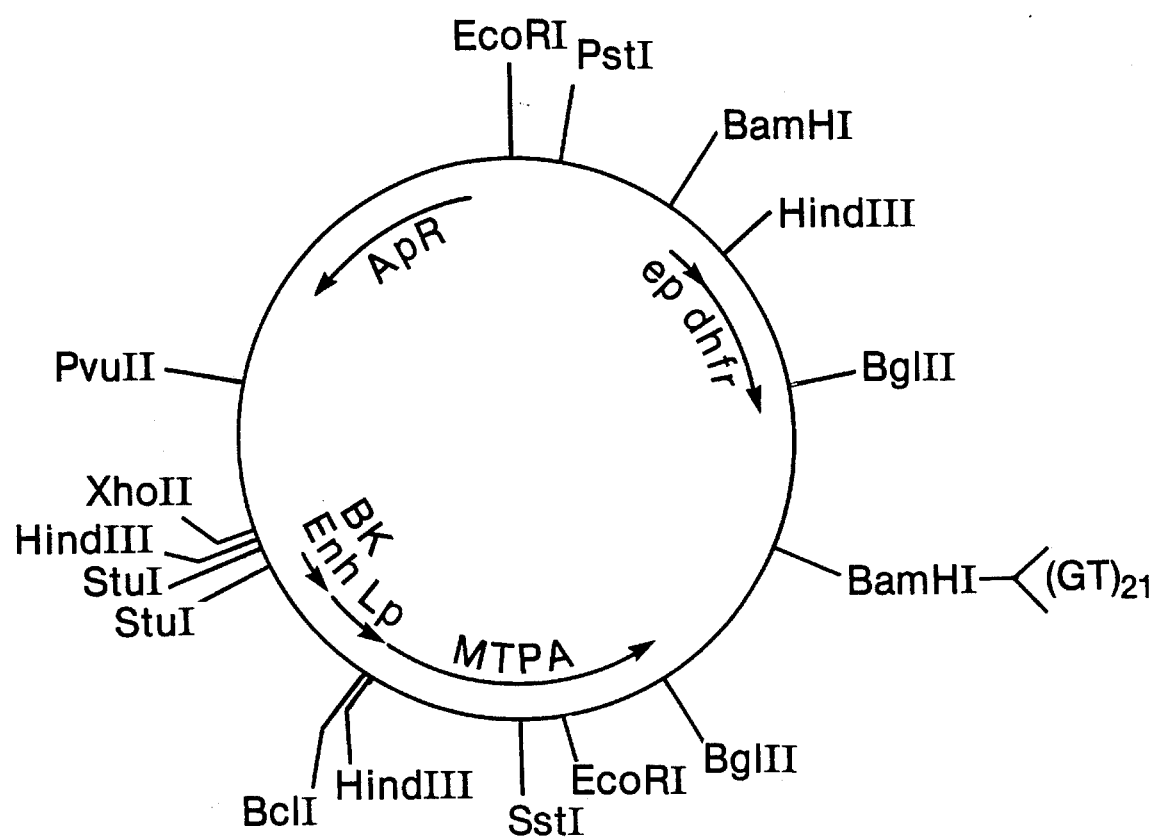
FIG. 18 is a restriction site and function map of plasmid pBLTdhrf1(GT).

Selectable markers may be introduced into BamHI digested plasmid pBLT or pBLT(GT). For example, with plasmid pBLT, in one construction, the hygromycin resistance gene-containing, ~2.5 kb BamHI restriction fragment of plasmid pSV2hyg was inserted to yield plasmids pBLThyg1 and pBLThyg2, and in another construction, the dhfr gene-containing ~1.9 kb BamHI restriction fragment of plasmid pBW32 was inserted to yield plasmids pBLTdhrf1 and pBLTdhrf2. The four plasmids, pBLThyg1, pBLThyg2, pBLTdhrf1, and pBLTdhrf2, differ only with respect to the type and/or orientation of the selectable marker. The construction protocol of plasmids pBLThyg1, pBLThyg2, pBLTdhrf1 and pBLTdhrf2 and their poly-GT containing derivatives, pBLThyg1(GT), pBLThyg2(GT), pBLTdhfr1(GT), and pBLTdhfr2(GT), is described in Example 16. A restriction site and function map of each of plasmids pBLThyg1(GT) and pBLTdhfr1(GT) is presented in FIGS. 17 and 18, respectively, of the accompanying drawings.

Figure 19:
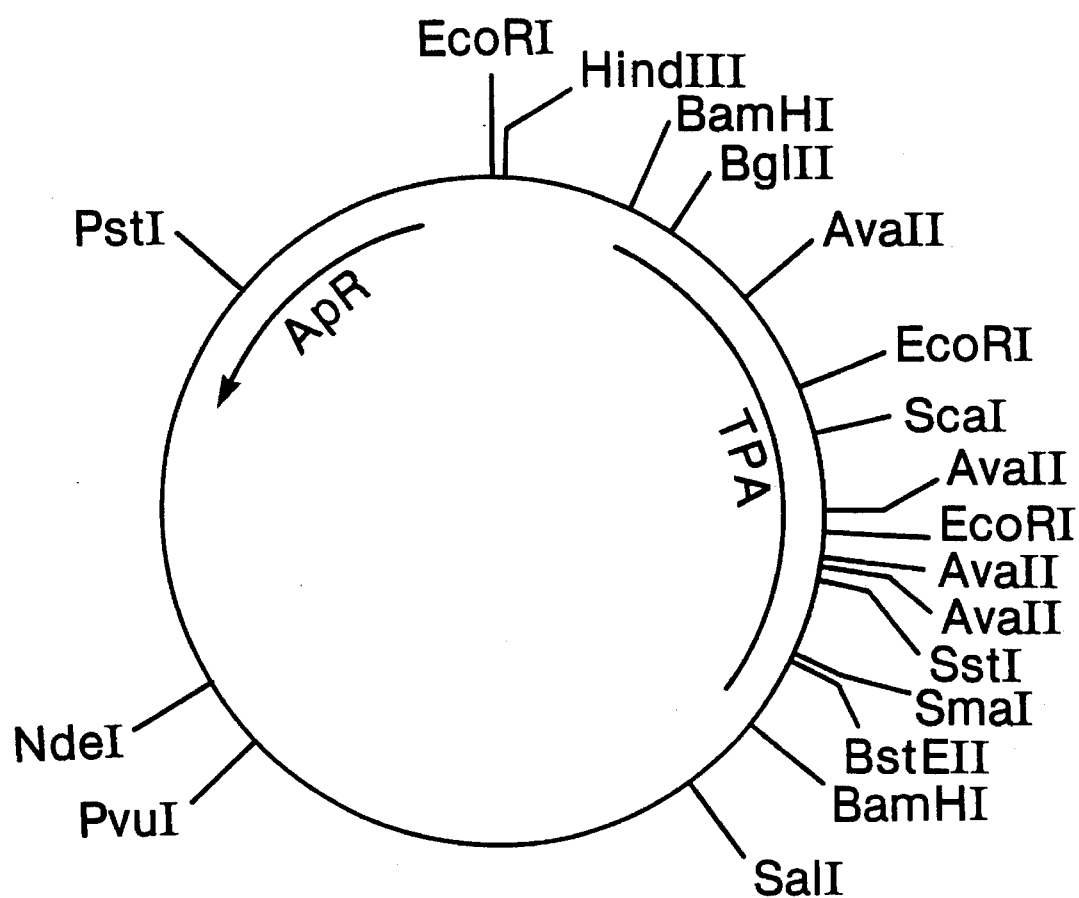
FIG. 19 is a restriction site and function map of plasmid pTPA603.

Other expression vectors described herein that drive expression of TPA or modified TPA were derived from plasmid pTPA103, an intermediate used in the construction of plasmid pBW32. The construction protocol for plasmid pTPA103 is described in Example 11, and a restriction site and function map of plasmid pTPA103 is presented in FIG. 19 of the accompanying drawings. To construct these derivatives, a BamHI restriction site was introduced immediately before the 5' end of the TPA coding region of plasmid pTPA103. Plasmid pTPA103 was digested with restriction enzyme HgaI to isolate the ~0.52 kb HgaI restriction fragment that comprises the 5' end of the TPA coding region. After Klenow treatment, the HgaI was ligated to BamHI linkers, digested with restriction enzyme BamHI, and inserted into BamHI-digested plasmid pBR322 to form plasmids pTPA601 and pTPA602.

Figure 20:
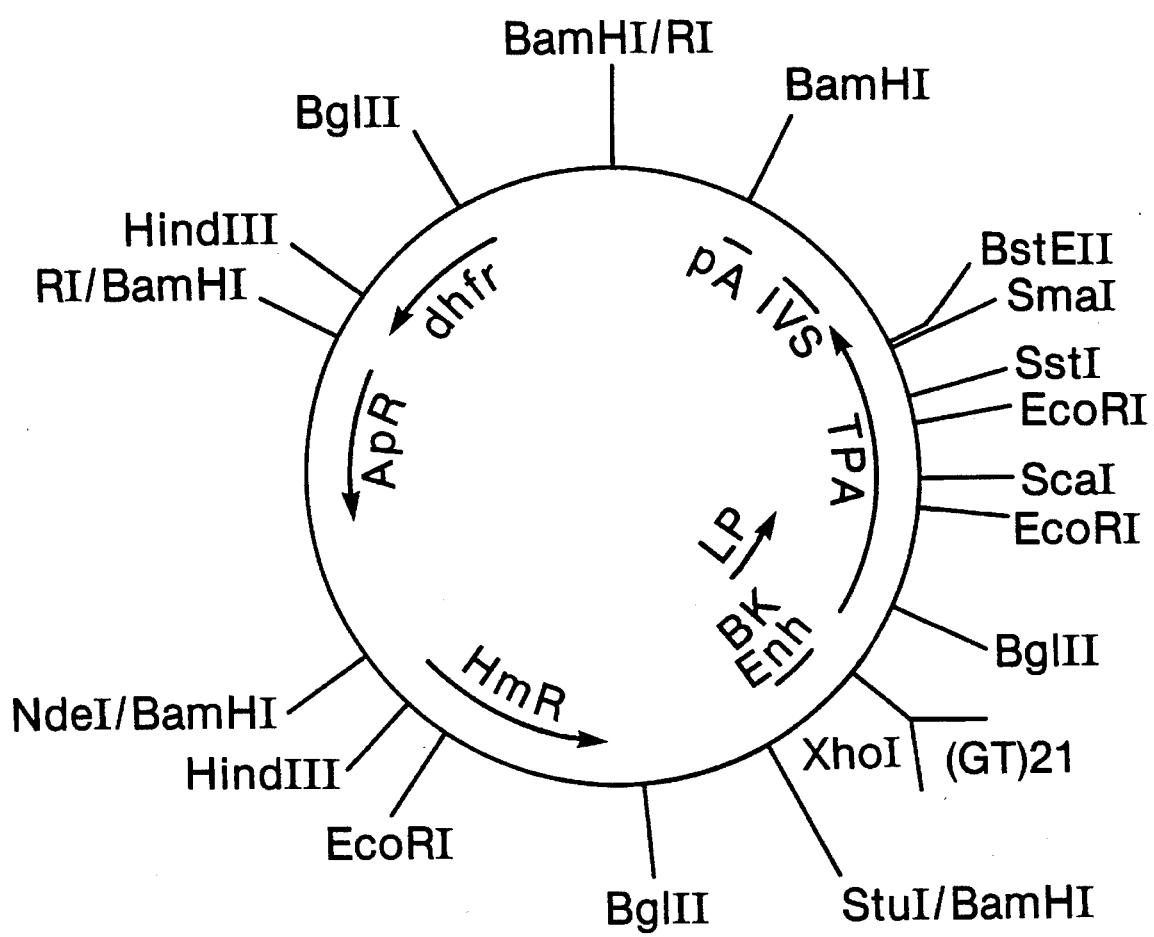
FIG. 20 is a restriction site and function map of plasmid phd(GT)TPA.
Figure 21:
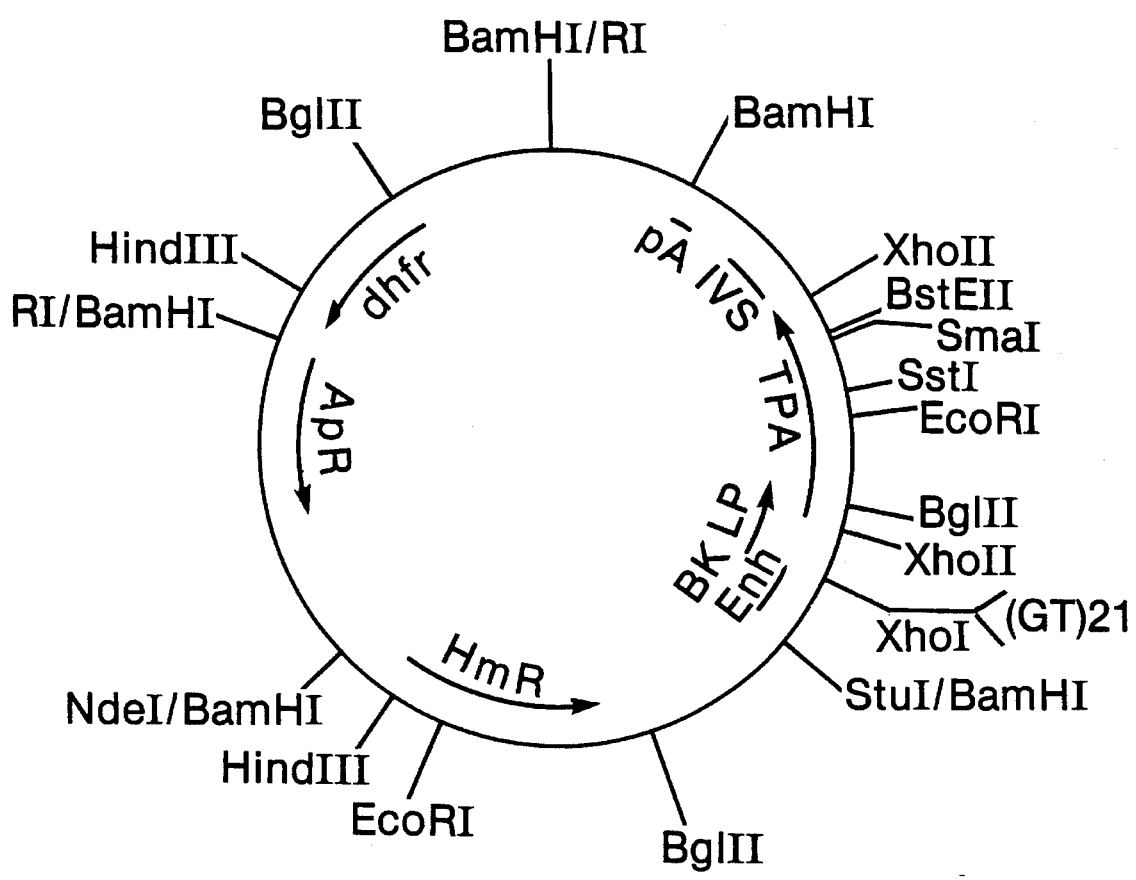
FIG. 21 is a restriction site and function map of plasmid phd(GT)MTPA.

Next, plasmid pTPA602 was digested with restriction enzymes BglII and SalI, and the resultant ~4.2 kb BglII-SalI restriction fragment was ligated to the ~2.05 kb SalI-BglII restriction fragment of plasmid pTPA103 to form plasmid pTPA603. Plasmid pTPA603 thus contains the complete coding sequence for TPA bounded by a BamHI restriction site on both ends. A restriction site and function map of plasmid pTPA603 is presented in FIG. 19 of the accompanying drawings. To construct a plasmid that is analogous to plasmid pTPA603 but that encodes a modified form of TPA, plasmid pTPA603 was digested with restriction enzymes BglII and SstI, and the resultant ~5.02 kb BglII-SstI fragment was ligated to the ~0.69 kb BglII-SstI restriction fragment of plasmid pBLT. The resultant plasmid, designated as pMTPA603, was then digested with restriction enzyme BamHI, and the resultant ~1.35 kb fragment was isolated. This fragment and the ~1.90 kb amHI restriction fragment of plasmid pTPA603 were individually ligated in separate ligations to BclI-digested plasmid phd (FIG. 14) to form the respective plasmids phclMTPA and phdTPA. The construction of plasmids phdTPA and phdMTPA, and their poly-GT containing derivatives, phdTPA(GT) and phd-MTPA(GT), beginning with the construction protocol for plasmid pTPA602, is described in Example 17. Restriction site and function maps of plasmids phd(GT)TPA and phd(GT)MTPA are presented in FIGS. 20 and 21, respectively, of the accompanying drawings.

The present invention comprises a method for using a poly-GT element with a BK enhancer in tandem with a eukaryotic promoter to drive transcription and expression of DNA sequences in eukaryotic host cells that express an immediate-early gene of a large DNA virus. Skilled artisans will recognize that virtually any eukaryotic promoter can be used. in tandem with the poly-GT element and the BK enhancer in the present method. For example, the SV40 early and late promoters, BK early and late promoters, early and late promoters of any of the polyoma viruses or papovaviruses, promoters of the herpes virus family, interferon e1 promoter, mouse metallothionein promoter, promoters of the retroviruses, β-globin promoter, promoters of the adenoviruses, promoters of poxviruses, sea urchin H2A promoter, conalbumin promoter, ovalbumin promoter, mouse β-globin promoter, and human β-globin promoter, can all serve as the eukaryotic promoter in the method of the present invention. Moreover, any sequence that can be used to initiate transcription, for example, a sequence containing a transcription start site, composed of a "TATA"-like sequence with or without an upstream "CCAAT" sequence, can serve as the promoter in the present invention. Such promoters can be utilized in the present method by conventionally inserting the promoters into expression vectors comprising a poly-GT element with the BK enhancer as exemplified herein using the adenovirus-2 late promoter, which is the preferred eukaryotic promoter for use in the present method. The BK enhancer used in the vectors described herein was isolated from the prototype strain of BK virus (ATCC VR-837). However, a number of BK virus variants have been isolated and described. Gardner et al., 1971, Lancet 1:1253, (see also Gardner, 1973, *Brit. Med. J.* 1:77–78) described the first isolation of a BK virus, and the Gardner strain is thus referred to as the prototype or wild-type BK virus. The Gardner strain of BK virus (FIG. 1) is available from the ATCC under the accession number ATCC VR-837. In fact, when ATCC VR-837 was obtained for use in constructing the vectors described herein, it was observed that BK variants were present in the population of viruses. Others have observed this phenomenon, i.e., Chuke et al., 1986, *J. Virology* 60(3):960. Neither the method of using a poly-GT element along with the BK enhancer in tandem with a eukaryotic promoter to drive expression of useful substances, such as nucleic acid and protein, in the presence of an immediate-early gene product of a large DNA virus nor any other method of the present invention is limited to the Gardner strain or particular BK variant as a source of the BK enhancer, although a variant enhancer isolated from the prototype strain (Example 18) is preferred. The following Table lists a representative number of BK variants that can be used in the methods described herein. In addition, a BK-like virus (simian agent 12) contains enhancer elements homologous to the BK enhancer and can be used in the methods as described herein. The enhancer elements of simian agent 12 are described in Cunningham et al., 1985, *J. Virol.* 54:483–492 and, for purposes of the present invention, are BK enhancer variants.

TABLE 1

BK Variants

| Strain designation | Description (relative to wild-type) | Reference |
|---|---|---|
| BKV(DUN) | BKV(DUN) contains an ~40 bp deletion at 0.7 m.u, just to the late coding side of the viral enhancer core. | Viral Oncology, 1980 (Raven Press, N.Y., ed. G. Klein), pp. 489–540. |
| BK(GS) and BK(MM) | These variants have numerous base differences that include rearrangements and duplications in the control region; some differences occur in the enhancer. | Pater et al., 1979, J. Virol. 32:220–225; Seif et al., 1979, Cell 18:963–977; Yang et al. 1979, Nuc. Acids Res. 7:651–668; and Pater, et al., 1979, Virology 131:426–436. |
| BK(JL) | Minor differences in restriction endonuclease patterns. | Pauw, et al., 1978, Arch. Virol. 57:35–42. |
| BK(RF) and BK(MG) | These variants are composed of two complementary defective molecules, both of which are required for infectivity and differ extensively in nucleotide sequence from prototype BK virus. | Pater et al., 1980, J. Virol. 36:480–487; Pater et al., 1981, J. Viro. 39:968–972; Pater et al., 1983, Virol. 131:426–436. |
| pm522 | Spontaneous mutation during propagation led to differences in host range and transforming potential, perhaps due to a deletion of two of the three enhancer repeats and the presence of two sets of shorter 37 bp repeats. | Watanabe et al., 1982, J. Virol. 42:978–985; Watanabe et al., 1984, J. Virol. 51:1–6. |
| tr530 tr531 tr532 | Spontaneous mutation during propagation of recombinant BK virus containing the pm522 enhancer region and having further duplications of short segments originating from the pm522 sequence. | Watanabe et al., 1984, J. Virol. 51:1–6. |
| BKV9 | Viable variant of BK virus isolated from a preparation of prototype (wt) BK virus contains an incomplete enhancer repeat and duplication of sequences to the late side of the enhancer. | Choke et al., 1986, J. Virol. 60:960–971. |
| BK virus-IR | BK virus variant isolated from a human tumor containing insertions and rearrangements in the enhancer region. This virus has an altered transformation phenotype. | Pagnani et al., 1986, J. Virol. 59:500–505. |

Skilled artisans will understand that a variety of eukaryotic host cells can be used in the present method, so long as the host cell expresses an immediate-early gene product of a large DNA virus. Because the immediate-early gene product can be introduced into host cells by many means, such as transformation with a plasmid or other vector, virtually any eukaryotic cell can be used in the present method. In particular, those skilled in the art will recognize that the E1A gene product which activates the GT enhancer system of the present invention may be provided in a variety of ways including: (1) introducing a single plasmid into the eukaryotic host cell which encodes the E1A gene along with the poly-GT element, the eukaryotic promoter and a structural gene to be expressed, for example, plasmid pLPCE1A(GT); (2) introducing two plasmids by cotransformation of the eukaryotic host cell, where one plasmid encodes E1A, for example, plasmid pSV2E1A, and one plasmid encodes the poly-GT element, the eukaryotic promoter and a structural gene to be expressed, for example, plasmid pBL(GT)cat; or (3) using an E1A expressing cell line such as 293 or AV12, and introducing a single plasmid encoding the poly-GT element, the eukaryotic promoter and the structural gene to be expressed. Human cells are preferred host cells in the method of the present invention. While human kidney cells are especially preferred as host cells, the adenovirus 5-transformed human embryonic kidney cell line 293, which expresses the E1A gene product, is most preferred and is available from the ATCC under the accession number ATCC CRL 1573.

The 293 cell line is preferred not only because 293 cells express the E1A gene product but also because of the ability of the 293 cells to γ-carboxylate and otherwise properly process complex gene products such as protein C. "γ-Carboxylation" refers to a reaction in which a carboxyl group is added to a glutamic acid residue at the γ-carbon, and a γ-carboxylated protein is a protein in which some amino acid residues have undergone γ-carboxylation. Kidney cells normally carboxylate and otherwise process certain proteins, but 293 cells are transformed with adenovirus, which generally results in a loss of specialized functions. Consequently, the present invention also comprises an improvement in the method for producing a protein that is naturally gamma carboxylated, properly folded, and processed wherein said protein is encoded in a recombinant DNA vector containing a poly-GT element and BK enhancer with the adenovirus late promoter. The 293N3S derivative of the 293 cell line is also suitable for use in the present invention and is able to grow in suspension culture as described in Graham, 1987, *J. Gen. Virol.* 68:937.

This method of producing a γ-carboxylated protein is not limited to adenovirus-transformed human embryonic kidney cells. Instead, the method of producing a γ-carboxylated protein is broadly applicable to all adenovirus-transformed host cells. Those skilled in the art also will recognize that the method can be practiced by first transforming a eukaryotic cell with an expression vector for a γ-carboxylated protein and then transforming the resulting transformant with adenovirus. Harold Ginsberg, in *The Adenoviruses* (1984, Plenum Press, New York), describes a number of adenoviruses and methods of obtaining adenovirus-transformed host cells. One especially preferred adenovirus-transformed host cell for purposes of expressing a γ-carboxylated protein encoded on a recombinant DNA expression vector is the Syrian hamster cell line AV12-664 (hereinafter AV12). The AV12 cell line was constructed by injecting adenovirus type 12 into the scruff of the neck of the Syrian hamster and isolating cells from the resulting tumor. The AV12 cell line is a preferred host for purposes of producing a γ-carboxylated protein. Examples of γ-carboxylated proteins include, but are not limited to, Factor VII, Factor IX, Factor V, protein C, protein S, protein Z, and prothrombin. The novel poly-GT—BK enhancer—eukaryotic promoter constructions described in Examples 18 and 19 were constructed using a method for improving expression using a poly-GT element and the BK enhancer with a eukaryotic promoter. Such method comprises placing a poly-GT element 5' or 3' relative to the eukaryotic promoter in the presence of the E1A gene product, and placing the BK enhancer within 0 to 300 nucleotides upstream of the 5' end of the CCAAT region or CCAAT region equivalent of the eukaryotic promoter used in tandem with the BK enhancer.

Other viral gene products, such as the VA gene product of adenovirus, increase the translation efficiency of mRNA molecules that contain the tripartite leader of adenovirus (Kaufman, 1985, *Proc. Natl. Acad. Sci. U.S.A.*, 82:689–693; Svensson and Akusjarul, 1985, EMBO, 4:957–964). The vectors of the present invention can be readily modified to encode the entire tripartite leader of adenovirus; the VA gene product may be used to increase translation of a given mRNA that only contains the first part of the adenovirus tripartite leader.

The sequence of the tripartite leader of adenovirus is depicted below:

```
*- - - - - - - - - - - - - - - - -First Part- - - - - - - - - - - - - - - - - - -*
5'-ACUCUCUUCCGCAUCGCUGUCUGCGAGGGCCAGCUGUUGGG

*- - - - - - - - - - - - - - - - - - - -Second Part- - - - - - - - - - - - - - - - -
CUCGCGGUUGAGGACAAACUCUUCGCGGUCUUUCCAGUACUCUU

- - - - - - - - - - - - - - - - - - - - - - - - - - - - - - * *- - - - - - - - - - -
GGAUCGGAAACCCGUCGGCCUCCGAACGUACUCCGCCACCGAGG

- - - - - - - - - - - - - - - - - - - - - - - - - -Third Part- - - - - - - - - - - -
GACCUGAGCGAGUCCGCAUCGACCGGAUCGGAAAACCUCUCGAG

- - - - - - - - - - - - - - - - - - - - - - - -*
AAAGGCGUCUAACCAGUCACAGUCGCA-3',
``` wherein A is riboadenyl, G is riboguanyl, C is ribocytidyl, and U is uridyl. As encoded in adenovirus DNA, the tripartite leader is interrupted by large introns. The presence of these introns or portions of the introns does not adversely affect expression levels. Plasmids p4–14 and p2–5 described herein contain the tripartite leader of adenovirus and are described more fully in Example 24, below. Plasmids p4–14(GT) and p2–5(GT) further contain a poly-GT element.

Many of the illustrative vectors of the invention, such as plasmids pBL(GT)cat and pLPC(GT), contain only the first part of the tripartite leader of adenovirus. As used herein, the "first part" of the tripartite leader of adenovirus, when transcribed into mRNA, comprises at least the sequence:

5'-ACUCUCUUCCGCAUCGCUGUCUGCGAGGGCCAG-3'

Thus, the present invention comprises an improvement in the method for producing a useful substance in a eukaryotic host cell that is transformed with a recombinant DNA vector that contains both a eukaryotic promoter and a DNA sequence that encodes the useful substance, the DNA sequence being positioned for expression from the pomoter, and wherein the cell containing the recombinant DNA vector is cultured under conditions suitable for expression of the useful substance, wherein the improvement comprises: (a) incorporating a poly-GT element into the vector; (b) incorporating DNA that encodes the first part of the tripartite leader of an adenovirus into the vector of step (a) such that, upon transcription, the mRNA produced encodes the useful product and, at the 5' end, contains said first part of the tripartite leader; (c) providing the cell containing the vector of step (b) with a first DNA sequence that codes for the expression of a VA gene product and a second DNA sequence that codes for the expression of an E1A gene product of the adenovirus; and (d) culturing the cell of step c) under conditions suitable for (i) expressing the VA gene product and for stimulating translation of the mRNA and (ii) expressing the E1A gene product and for stimulating the enhancer activity of the poly-GT element, subject to the limitation that the mRNA does not contain the entire tripartite leader of the adenovirus.

Plasmids coding for VA have been constructed from adenovirus DNA. A restriction fragment of ~1723 bp, defined by a SalI site (at nucleotide 9833) and a HindIII site (at nucleotide 11556), was isolated from adenovirus-2 DNA and cloned into HindIII-SalI-digested plasmid pBR322, thus replacing the ~622 bp SalI-HindIII fragment of pBR322, to construct plasmid pVA. A plasmid coding for neomycin resistance and VA has been constructed by isolating a ~1826 bp NruI fragment from plasmid pVA and inserting that fragment into Klenow-treated, BamHI-digested plasmid pSVNneo (available from BRL). The resultant plasmid, designated pVA-Neo, can be used to insert the VA gene into any cell line by selection of neomycin (G418) resistance after transformation.

The VA gene product of adenovirus, however, may exert its greatest positive effect on expression of recombinant genes containing either the first part of the tripartite leader of adenovirus, or the entire tripartite leader, in the first few days following transformation of the host cell with a VA-encoding vector. Subsequent expression of the VA gene product in the host cell after the first few days may not give optimal expression levels.

The T antigen of SV40, BK virus, or any other polyomavirus can also be used with the vectors described herein to increase promoter activity and/or increase copy number of the plasmid by stimulating replication. SV40 T antigen stimulates transcription from both the adenovirus and BK late promoters. SV40 T antigen does not appear to transactivate the poly-GT element. However, by including T-antigen-coding sequences on the expression vectors of the present invention or by cotransfection of the vectors with a plasmid(s) carrying T-antigen-coding sequences, amplification of copy number can be obtained prior to the application of selective pressure as outlined in Example 22. This will allow for high copy number integration of the expression vector. Thus, in the preferred embodiment of the present invention, the recombinant DNA expression vector comprises a poly-GT element, the BK enhancer isolated from the prototype strain positioned less than 300 nucleotides upstream of the adenovirus late promoter, which itself is positioned to drive expression of a gene that encodes at least the first part of the tripartite leader and a useful substance. This preferred vector is used to transform human embryonic kidney 293 cells which constitutively express the E1A gene product and that have been modified, either before or after transformation with the expression vector, to express the VA gene product of an adenovirus. For stable transformants, however, presence of the VA gene product may not be desired.

The following Examples more fully describe the methods, compounds, and recombinant organisms of the present invention. Those skilled in the art will recognize that the particular reagents, equipment, and procedures described in the Examples are merely illustrative and do not limit the present invention.

EXAMPLE 1

Preparation of Poly-GT Element

The single-stranded DNA fragments used in the construction of a poly-GT element were chemically synthesized either by using a Systec 1450A DNA Synthesizer (Systec, Inc., 3816 Chandler Drive, Minneapolis, Minn. 55401) or an ABS 380A DNA Synthesizer (Applied Biosystems, Inc., 850 Lincoln Centre Drive, Foster City, Calif. 94404). Many DNA synthesizing instruments are known in the art and can be used to make the fragments. In addition, the fragments can also be conventionally prepared in substantial accordance with the procedures of Itakura et al., 1977, *Science*, 198:1056 and Crea et al, 1978, *Proc. Nat. Acad. Sci.* U.S.A., 75:5765.

Five hundred nanograms of each single strand of the poly-GT element were annealed after synthesis of the single strands as follows. Sixteen μl of strand 1 and 11 μl of strand 2 were mixed together in an eppendorf tube, and 3 μl of 10× TM buffer (0.5M Tris-HCl pH= 7.6, 0.1M MgCl$_2$) were added. The tube was placed in a boiling water bath for 2 minutes and then allowed to cool slowly by incubation at room temperature and then at 4° C. This process annealed the single strands to form the double-stranded poly-GT element. After this incubation, the 30 μl sample was lyophilized and then suspended in 7 μl of glass-distilled H$_2$O (dH$_2$O). The poly-GT element constructed had the following structure:

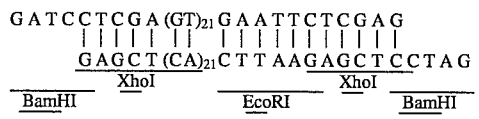

As shown, this poly-GT element was constructed to include a $(GT)_n$-$(CA)_n$ segment where n—21, where this segment is flanked by DNA sequences that are recognition sites for the following restriction enzymes: BamHI (GSGATCC), XhoI (CTCGAG) and EcoRI (GSAATTC). This poly-GT element can therefore be easily inserted into a BamHI site or an XhoI site in a variety of expression vectors to create a poly-GT containing derivative of the expression vector as described in a number of following Examples. Alternatively, the poly-GT element can be inserted by blunt end ligation into any restriction site of an expression vector.

EXAMPLE 2

Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about 105 plaque-forming units (pfu)/ml. The host of choice for the preparation of BK virus DNA is primary human embryonic kidney (PHEK)

cells, which can be obtained from Flow Laboratories, Inc., 7655 Old Springhouse Road, McLean, Va. 22101, under catalogue number 0-100 or from M.A. Bioproducts under catalogue number 70-151.

About five 75 mm polystyrene flasks comprising confluent monolayers of about 106 PHEK cells are used to prepare the virus. About 1 ml of BK virus at a titer of 105 pfu/ml is added to each flask, which is then incubated at 37° C. for one hour, and then, fresh culture medium (Dulbecco's Modified Eagle's Medium, Gibco, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000× g. The virus in 1 liter of supernatant fluid is precipitated and collected by the addition of 100 g of PEG-6000, incubation of the solution for 24 hours at 4° C., and centrifugation at 5000× g for 20 minutes. The pellet is dissolved in 0.1× SSC buffer (1× SSC=0.15M NaCl and 0.015M sodium citrate, pH=7) at 1/100th of the original volume. The virus suspension is layered onto a 15 ml solution of saturated KBr in a tube, which is centrifuged at 75,000× g for 3 hours. Two bands are evident in the KBr solution after centrifugation. The lower band, which contains the complete virion, is collected and desalted on a Sephadex®G-50 column (Sigma Chemical Co., P.O. Box 14508, St. Louis, Mo. 63178) using TE (10mM Tris-HCl, pH 7.8, and 1 mM EDTA) as an elution buffer. Sodium dodecyl sulfate (SDS) is added to the solution of purified virions obtained from the column to a concentration of 1%; pronase is added to a concentration of 100 µg/ml, and the solution is incubated at 37° C. for 2 hours. Cesium chloride is then added to the solution to a density of 1.56 g/ml, and ethidium bromide is added to the solution to a final concentration of 100 µg/ml. The solution is centrifuged in a Sorvall (DuPont Inst. Products, Biomedical Division, Newton, Conn. 06470) 865 rotor or similar vertical rotor at 260,000× g for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000× g for 10 minutes. The resulting pellet of BK virus DNA is suspended in TE buffer at a concentration of 1 mg/ml.

EXAMPLE 3

Construction of Plasmids pBKneo1 and pBKneQ2

*E. coli* K12 HB101/pdBPV-MMTneo cells are obtained in lyophilized form from the American Type Culture Collection under the accession number ATCC 37224. The lyophilized cells are plated on L-agar (L broth with 15 g agar per liter) plates containing 100 µg/ml ampicillin and incubated at 37° C. to obtain single colony isolates.

One liter of L broth (10 g tryptone, 10 g NaCl, and 5 g yeast extract per liter) containing 50 µg/ml ampicillin was inoculated with a colony of *E. coli* K12 HB101/pdBPV-MMTneo and incubated in an airshaker at 37° C. until the $O.D._{590}$ was ~1 absorbance unit, at which time 150 mg of chloramphenicol were added to the culture. The incubation was continued for about 16hours; the chloramphenicol addition inhibits protein synthesis, and thus inhibits further cell division, but allows plasmid replication to continue.

The culture was centrifuged in a GSA rotor (Sorvall) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repellered. The supernatant was discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution, 3 ml of 0.25M EDTA, pH=8.0, and 100 µl of 10 mg/ml RNAse A were added to the solution, which was then incubated on ice for 15 minutes. Three ml of lysing solution (prepared by mixing 3 ml of 10% Triton-X 100, 75 ml of 0.25M EDTA, pH=8.0, 15 ml of 1M Tris-HCl, pH=8.0, and 7 ml of $dH_2O$) were added to the lysozyme-treated cells, mixed, and the resulting solution incubated on ice for another 15 minutes. The lysed cells were frozen in a dry iceethanol bath and then thawed.

The cellular debris was removed from the solution by centrifugation at 25,000 rpm for 40 minutes in SW28.1 rotor (Beckman, Scientific Instrument Division, Campus Drive at Jamboree Blvd., Irvine, Calif. 92713) and by extraction with buffered phenol. About 30.44 g of CsCl and 1 ml of a 5 mg/ml ethidiumbromide solution were added to the cell extract, and then, the volume of the solution was adjusted to 40 ml with TES buffer. The solution was decanted into a VTi50 ultracentrifuge tube (Beckman), which was then sealed and centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol and 1 volume of 3M sodium acetate were then added to the solution, which was then incubated overnight at −20° C. The plasmid DNA was pelleted by centrifuging the solution in an SS34 rotor (Sorvall) for 15 minutes at 10,000 rpm.

The ~1 mg of plasmid pdBPV-MMTneo DNA obtained by this procedure was suspended in 1 ml of TE buffer and stored at −20° C. The foregoing plasmid isolation procedure is generally used when large amounts of very pure plasmid DNA are desired. The procedure can be modified to rapidly obtain a smaller, less pure amount of DNA, such as is needed when screening transformants for the presence of a given plasmid, by using only about 5 ml of cultured cells, lysing the cells in an appropriately scaled-down amount of lysis buffer, and replacing the centrifugation steps with phenol and chloroform extractions.

About 5 µg (5 µl) of the plasmid pdBPV-MMTneo DNA prepared above and 5 µg (5 µl) of the BK virus DNA prepared in Example 2 were each digested at 37° C. for 2 hours in a solution containing 2 H1 of 10× BamHI buffer (1.5M NaCl; 60M Tris-HCl, pH=7.9; 60 mMMgCl₂; and 1 mg/ml BSA), 1 µl (about 20 units; all enzyme units referred to herein, unless otherwise indicated, refer to the unit definitions of New England Biolabs, 32 Tozer Road, Beverly, Mass. 01915, although the actual source of enzymes may have been different) of restriction enzyme BamHI, and 7µl of $dH_2O$. The reaction was stopped by an extraction with an equal volume of phenol, followed by two extractions with chloroform. Each BamHI-digested DNA was then precipitated, collected by centrifugation, and resuspended in 5µl of dH₂O.

About 1 µl of 10× ligase buffer was added to a mixture of BamHI-digested plasmid pdBPV-MMTneo (1 µl) and BamHI-digested BK virus DNA (1 µl). After 1 µl (~1000 units) of T4 DNA ligase and 6 µl of dH₂O were added to the mixture of DNA, resulting reaction was incubated at 16° C. overnight. The ligated DNA constituted the desired plasmids pBKneo1 and pBKneo2, which differ only with respect to the orientation of the BK virus DNA. A restriction site and function map of plasmid pBKneo1 is presented in FIG. 2 of the accompanying drawings.

*E. coli* K12 HB101 cells are available in lyophilized form from the Northern Regional Research Laboratory under the accession number NRRL B-15626. *E. coli* K12 HB101 cells were cultured, made competent for transformation, and transformed with the ligated DNA prepared above as follows. A 50 ml culture of *E. coli* K12 HB101 in L broth was grown to an optical density at 650 nanometers (O.D.$_{650}$) of approximately 0.4 absorbance units. The culture was chilled on ice for ten minutes, and the cells were collected by centrifugation. The cell pellet was resuspended in 25 ml of cold 100 mM MgCl$_2$ and incubated on ice for 25 minutes. The cells were once again pelleted by centrifugation, and the pellet was resuspended in 2.5 ml of cold 100 mM CaCl$_2$ and incubated for 30 minutes on ice. After the incubation, the cells are competent for the uptake of transforming DNA.

Two hundred 1 of this cell suspension were mixed with the ligated DNA prepared above and incubated on ice for 30 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 1 hour. Aliquots of the cell mixture were plated on L-agar plates containing 100 µg/ml ampicillin. The plates were incubated at 37° C. overnight. *E. coli* K12 HB101/pBKneo1 and *E. coli* K12/pBKneo2 transformants were identified by their ampicillin-resistant phenotype and by restriction enzyme analysis of their plasmid DNA. Plasmid DNA was obtained from the *E. coli* K12 HB101/pBKneo1 and *E. coli* K12/pBKneo2 cells as described above.

EXAMPLE 4

Construction of plasmid pLPcat and pLP(GT)c

A. Construction of Plasmid pLPcat

The virion DNA of adenovirus 2 (Ad2) is a double-stranded linear molecule about 35.94 kb in size. The Ad2 late promoter can be isolated on an ~0.316 kb AccI-PVuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with Acc-I and PvuII to obtain the desired fragment.

About 50 µg of Ad2 DNA (available from BRL) are dissolved in 80µl of dH$_2$O and 10µl of 10× BalI buffer (100 mM Tris-HCl, pH=7.6; 120 mM MgCl$_2$; 100 mM DTT; and 1 mg/ml BSA). Ten µl (about 20 units) of restriction enzyme BalI are added to the solution of Ad2 DNA, and the resulting reaction is incubated at 37° C. for 4 hours.

The BalI-digested DNA is loaded onto a 1% agarose gel and electrophoresed until the restriction fragments are well separated. Visualization of the electrophoresed DNA is accomplished by staining the gel in a dilute solution (0.5 µg/ml) of ethidium bromide and exposing the stained gel to long-wave ultraviolet (UV) light. The DNA is isolated from the agarose gel as follows. A narrow section of the gel containing the desired fragment (visualized with UV light) is cut out from the gel and placed in an eppendorf tube. The tube containing the gel section is first placed at −70° C. or on dry ice to freeze the gel, then placed at room temperature to thaw, then frozen and thawed again. After these two freeze-thaw cycles, liquid in the tube is collected and the DNA fragment is removed from the liquid by 3 successive extractions with isoamyl alcohol, followed by ethanol precipitation. The purified fragment obtained is dissolved in 10 µl of TE buffer. About 6 µl of dH$_2$O and 2 µl of 10× AccI buffer (60 mM NaCl; 60 mM Tris-HCl, pH=7.5; 60 mM MgCl$_2$; 60 mM DTT; and 1 mg/ml BSA) are added to the solution of the ~2.4 kb BalI restriction fragment of Ad2. After the addition of 2µl (about 10 units) of restriction enzyme AccI to the solution of DNA, the reaction is incubated at 37° C. for 2 hours. After the AccI digestion, the DNA is collected by ethanol precipitation and resuspended in 16 µl of dH$_2$O and 2 µl of 10× pvBII buffer (600 mM NaCl; 60 mM Tris-HCl, pH=7.5; 60 mM MgCl$_2$; 60 mM DTT; and 1 mg/ml BSA). After the addition of about 2 µl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb Acc-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in 250 µl of extraction buffer (500 mM ammonium acetate; 10 mM magnesium acetate; 1 mM EDTA; and 0.1% SDS). The following morning, the mixture is centrifuged, and the pellet is discarded. The DNA in the supernatant is precipitated with ethanol; about 2 µg of tRNA are added to ensure complete precipitation of the desired fragment. About 0.2 µg of the ~0.32 kb AccI-PvuII restriction fragment are obtained and suspended in 7 µl of dH$_2$O.

About 0.25 µg (in 0.5 µl) of BclI linkers (5' CTGATCAG-3', available from New England Biolabs), which had been kinased in substantial accordance with the procedure described in Example 11A, below, was added to the solution of the 0.32 kb AccI-PvuII restriction fragment, and then, 1 µl (about 1000 units) of T4 DNA ligase and 1 µl of 10× ligase buffer (0.5M Tris-HCl, pH=7.8; 100 mM MgCl$_2$; 200 mM DTT; 10 mM ATP; and 0.5 mg/ml BSA) were added to the solution of DNA, and the resulting reaction was incubated at 16° C. overnight. The BclI linkers could ligate only to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

*E. coli* K12 HB101/pSV2cat cells are obtained in lyophilized form from the ATCC under the accession number ATCC 37155, and plasmid pSV2cat DNA was isolated from the cells in substantial accordance with the procedure of Example 3. A restriction site and function map of plasmid pSV2cat is presented in FIG. 3 of the accompanying drawings. About 1 mg of plasmid pSV2cat DNA is obtained and dissolved in 1 ml of TE buffer. About 3 μg (3 μl) of the plasmid pSV2cat DNA were added to 2 μl of 10× AccI buffer and 16 μl of dH$_2$O, and then, 3 μl (about 9 units) of restriction enzyme AccI were added to the solution of pSV2cat DNA, and the resulting reaction was incubated at 37° C. for 2 hours. The AccI digested plasmid pSV2cat DNA was then digested with restriction enzyme StuI by adding 3 μl of 10× StuI buffer (1.0M NaCl; 100 mM Tris-HCl, pH 8.0; 100 mM MgCl$_2$; 60 mM DTT; and 1 mg/ml BSA), 5 μl of dH$_2$O, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

About 4 μl of the AccI-StuI-digested plasmid pSV2cat DNA were mixed with about 7 μl of the ~0.32 kb Acc I-PvuII (with BclI linkers attached) restriction fragment of Ad2, and after the addition of 3 μl of 10× ligase buffer, 15 μl of dH$_2$O, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene.

The ligated DNA was used to transform *E. coli* K12 HB101 cells in substantial accordance with the procedure of Example 3. The transformed cells were plated on L-agar containing 50 μg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 3.

B. Construction of pLP(GT)cat

1. Construct with Plasmid pLPcat

About 1 μg of the poly-GT element as prepared in Example I in 30 μl dH$_2$O is added to 15 μl 10× Core buffer (50mM Tris-HCl, pH=8.0; 10 mM MgCl$_2$; and 50 mM NaCl$_2$) and 95 μl dH$_2$O. Ten 1 (about 100 units) of restriction enzyme XhoI are added to the solution of poly-GT element, and the resulting reaction is incubated at 37° C. for 3 hours. After the XhoI digest, the DNA is collected by ethanol precipitation and resuspended in 7μl of dH$_2$O.

About 5 g of plasmid pLPcat DNA in 10 μl of TE buffer is dissolved in 10 μl of 10× Core buffer and 75 μl dH$_2$O. Five HI (about 60 units) of XhoI are added to the solution of DNA, and the resulting reaction is incubated at 37° C. for 2 hours. The reaction is stopped by extracting the reaction mixture first with phenol: chloroform, then with chloroform: isoamyl alcohol. The XhoI-digested plasmid pLPcat DNA is precipitated with ethanol and resuspended in 100 μl of TE buffer. The XhoI-digested plasmid pLPcat DNA is treated with calf-intestinal alkaline phosphatase as follows. The XhoI-digested plasmid pLPcat DNA was diluted to 100 μl in TE buffer; about 0.06 units of calf-intestinal alkaline phosphatase (Collaborative Research, Inc., 128 Spring Street, Lexington, Mass. 02173) were added to the solution, and the resulting reaction was incubated at 37° C. for 30 minutes. The solution was adjusted to contain 1× SET (5 mM Tris-HCl, pH=7.8; 5 mM EDTA; and 15 mM NaCl), 0.3M sodium acetate, and 0.5% SDS and then incubated at 65° C. for 45 minutes. The phosphatase treatment prevents the pLPcat DNA from self ligating. The DNA was collected by ethanol precipitation and then resuspended in 10 μl of 10 mM Tris-HCl, pH 8.0 buffer.

About 1 μl of 10× ligase buffer (0.5M Tris-HCl, pH=7.8; 100 mM MgCl$_2$; 200 mM DTT; 10 mM ATP; and 0.5 mg/ml BSA) is added to a mixture of 1 μl (about 50 ng) of the XhoI-digested, phosphatased plasmid pLPcat DNA and 7 μl (about 100 ng) of the XhoI-digested poly-GT element. One μl (about 1000 units) of T4 DNA ligase is added to the solution of DNA, and the resulting reaction is incubated at 16° C. overnight. The ligated DNA constitutes the desired plasmid pLP(GT)cat. A restriction site and function map of plasmid pLP(GT)cat is presented in FIG. 4 of the accompanying drawings.

The ligated DNA is used to transform *E. coli* K12 HB101 cells in substantial accordance with the procedure of Example 3. The transformed cells are plated on an L-agar containing 50 μg/ml ampicillin; restriction enzyme analysis of plasmid DNA is used to identify the *E. coli* K12 HB101/pLP(GT)cat transformants. Plasmid pLP(GT)cat DNA is isolated from the transformants for use in subsequent constructions in substantial accordance with the plasmid isolation procedure described in Example 3.

2. Construct with Plasmid pBL(GT)cat

Alternatively, plasmid pLP(GT)cat has been prepared starting with plasmid pBL(GT)cat DNA (described in Example 5 below) and deleting a fragment containing the BK enhancer according to the following procedure. About 9.5 μg of plasmid pBL(GT)cat DNA prepared as in Example 5B in 10 μl of Tris buffer (10 mM Tris-HCl, pH 8.0) were added to 10 μl of 10× high salt buffer and 69 μl dH$_2$O. About 9 μl (about 18 units) of restriction enzyme MstII and 2 μl (about 20 units) of restriction enzyme BglII were added to the DNA solution, and the resulting reaction was incubated at 37° C. for 2 hours. The reaction was then stopped and the DNA extracted and precipitated as above. The DNA precipitate was dissolved in 45 μl of dH$_2$O.

To the 45 μl of MstII/BglII-digested plasmid pBL(GT)cat DNA were added 5 μl of 10× Klenow buffer and 1 μl (about 5 units as marketed by BRL) Klenow enzyme and incubated in substantial accordance with the procedure of Example 10. The Klenow-treated, MstII/BglII-digested plasmid pBL(GT)cat DNA was extracted once with phenol:chloroform, once with chloroform:isoamyl alcohol, then precipitated with ethanol, and finally resuspended in 10 μl of Tris buffer.

To about 1 μl (about 0.5 μg) of the Klenow-treated, MstII/BglII-digested plasmid pBL(GT)cat DNA was added 1 μl 10× ligase buffer, 7 μl dH$_2$O and 1 μl (about 100 units) of T4 DNA ligase. The resulting reaction was incubated at 16° C. overnight and the ligated DNA constituted an alternative construct of the desired plasmid pLP(GT)cat, which construct may also be designated as plasmid pBL(GT)cat BglII/MstII. The deletion of the ~480 bp BgII/MstII fragment from pBL(GT)cat removes the BK enhancer that was ligated into plasmid pLPcat in Example 5A to create plasmid pBLcat.

EXAMPLE 5

Construction of Plasmids pBLcat and pBL(GT)cat

A. Construction of Plasmid pBLcat

About 88 μg of plasmid pBKneo1 DNA in 50 μl of TE buffer were added to 7.5 μl of 10× AccI buffer, 30 μl of dH$_2$O and 15 μl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated in substantial accordance with the procedure described in Example 4A. About 5 μg of the fragment were resuspended in 5 μl of 10× PvuII buffer, 45 μl of dH₂O, and 5 μl (about 25 units) of restriction enzyme PvuII, and the resulting reaction was incubated at 37° C. for 2 hours. The PvuII-digested DNA was then isolated and prepared for ligation in substantial accordance with the procedure of Example 4A. About 2 μg of the desired ~1.28 kb AccI-PvuII fragment were obtained and dissolved in 5 μl of TE buffer.

About 1 μg of plasmid pLPcat DNA was dissolved in 5 μl of 10× AccI buffer and 40 μl of dH₂O. Five μl (about 25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10× StuI buffer, 40 μl of dH₂O, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

The 5 μl of ~4.81 kb AccI-StuI restriction fragment of plasmid pLPcat were added to 5 μl of ~1.28 kb AccI PvuII restriction fragment of BK virus. After the addition of 3 μl of 10× ligase buffer, 15 μl of dH₂O, and 2 μl (about 1000 units) of T4 DNA ligase to the mixture of DNA, the resulting ligation reaction was incubated at 16° C. overnight. The ligated DNA constituted the desired plasmid pBLcat.

The ligated DNA was used to transform *E. coli* K12 HB101 cells in substantial accordance with the procedure described in Example 3. *E. coli* K12 HB101/pBLcat transformants were identified by restriction enzyme analysis of their plasmid DNA. Plasmid pBLcat DNA was prepared for use in subsequent constructions in substantial accordance with the procedure of Example 3.

B. Construction of Plasmid pBL(GT)cat

About 1 μg of the poly-GT element prepared as in Example 1 in 30 μl dH₂O was digested with XhoI in substantial accordance with the procedure of Example 4B.1. About 23 μg of plasmid pBLcat DNA in 10 μl of TE buffer were digested with XhoI and phosphatased in substantial accordance with the procedure of Example 4B.1. The XhoI-digested, phosphatased plasmid pBLcat DNA and the XhoI-digested poly-GT element were ligated in substantial accordance with the procedure of Example 4B.1. The ligated DNA constituted the desired plasmid pBL(GT)cat. A restriction site and function map of plasmid pBL(GT)cat is presented in FIG. 5 of the accompanying drawings.

The ligated DNA was used to transform *E. coli* K12 HB101 cells in substantial accordance with the procedure of Example 3. The transformed cells were plated on L-agar containing 50 μg/ml ampicillin; restriction enzyme analysis of plasmid DNA was used to identify *E. coli* K12 HB101/pBL(GT)cat transformants. Plasmid pBL(GT)cat DNA was isolated from the transformants in substantial accordance with the plasmid isolation procedure described in Example 3.

EXAMPLE 6

Construction of Plasmids pSBLcat and pSBL(GT)cat

A. Construction of Plasmid pSBLcat

About 100 μg of plasmid pBLcat DNA were dissolved in 10 μl of 10× HindIII buffer (0.5M NaCl; 0.1M Tris HCl, pH 8.0; 0.1M MgCl₂; and 1 mg/ml BSA) and 80 μl of dH₂O. About 10 μl (about 100 units) of restriction enzyme HindIII were added to the solution of plasmid pBLcat DNA, and the resulting reaction was incubated at 37° C. for 2 hours. The HindIII-digested plasmid-pBLcat DNA was loaded onto a 1% agarose gel and electrophoresed until the ~0.87 kb HindIII restriction fragment that comprises the BK enhancer and Ad2 late promoter was well separated from the other digestion products; then, the ~0.87 kb fragment was isolated and prepared for ligation in substantial accordance with the procedure of Example 4A. About 10 μg of the desired fragment were obtained and dissolved in 50 μl of TE buffer.

About 1 μg of plasmid pSV2cat DNA in 1 μl of TE buffer was dissolved in 2 μl of 10× HindIII buffer and 16 μl of dH₂O. One μl (about 10 units) of restriction enzyme HindIII was added to the solution of DNA, and the resulting reaction was incubated at 37° for 2 hours. The reaction was stopped by extracting the reaction mixture first with phenol, then twice with chloroform. The HindIII-digested plasmid pSV2cat DNA was precipitated with ethanol and resuspended in 100 μl of TE buffer. The HindIII-digested plasmid pSV2cat DNA was treated with calf-intestinal alkaline phosphatase in substantial accordance with the procedure of Example 4B and the resuspended in 10 μl of TE buffer. About 5 μl of the ~0.87 kb HindIII restriction fragment of plasmid pBLcat were added to the 10 μl of HindIII-digested plasmid pSV2cat, and then, 3 μl of 10× ligase buffer, 2 μl (about 1000 units) of T4 DNA ligase, and 13 μl of dH₂O were added to the solution of DNA, and the resulting reaction was incubated at 16° C. for 2 hours. The ligated DNA constituted the desired plasmid pSBLcat. The ligated DNA was used to transform *E. coli* K12 HB101 in substantial accordance with the procedure of Example 3. The transformed cells were plated on L-agar containing ampicillin, and the plasmid DNA of the ampicillin-resistant transformants was examined by restriction enzyme analysis to identify the *E. coli* K12 HB101/pSBLcat transformants. The ~0.87 kb HindIII restriction fragment that encodes the BK enhancer and Ad2 late promoter could insert ihto HindIII-digested plasmid pSBLcat in one of two orientations, only one of which yields plasmid pSBLcat.

B. Construction of Plasmid pSBL(GT)cat

A poly-GT element is inserted into the unique XhoI site in plasmid pSBLcat, between the BK enhancer and the Ad2 late promoter, in substantial accordance with the procedure of Example 4B.1. The XhoI-digested poly-GT element and XhoI-digested plasmid pSBLcat DNA are ligated and the ligated DNA constitutes the desired plasmid pSBL(GT)cat. A restriction site and function map of plasmid pSBL(GT)cat is presented in FIG. 6 of the accompanying drawings.

EXAMPLE 7

Construction of Plasmid pL133

A. Construction of Intermediate Plasmid pSV2-HPC8

Plasmid pHC7 comprises a DNA sequence that encodes human protein C. One liter of L broth containing 15 μg/ml tetracycline was inoculated with a culture of *E. coli* K12

RR1/pHC7 (NRRL B-15926), and plasmid pHC7 DNA was isolated and purified in substantial accordance with the procedure of Example 3. About 1 mg of plasmid pHC7 DNA was obtained by this procedure, suspended in 1 ml of TE buffer, and stored at −20° C. A restriction site and function map of plasmid pHC7 is presented in FIG. 7 of the accompanying drawings.

Fifty μl of the plasmid pHC7 DNA were mixed with 5 μl (about 50 units) of restriction enzyme BanI, 10 μl of 10× BanI reaction buffer (1.5M NaCl; 60 mM Tris-HCl, pH=7.9; 60 mM $MgCl_2$; and 1 mg/ml BSA), 35 μl of $dH_2O$, and incubated until the digestion was complete. The BanI-digested plasmid pHC7 DNA was then electrophoresed on a 3.5% polyacrylamide gel (29:1, acrylamide: bisacrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM ammonium acetate, 10 mM magnesium acetate, 1 mM EDTA, 1% SDS, and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8. The DNA fragments used in the construction of the linker were synthesized in substantial accordance with the procedures described in Example 1.

Five hundred picomoles of each single strand of the synthesized linker were kinased in 20 μl of reaction buffer, which contained 15 units (about 0.5 μl) T4 polynucleotide kinase, 2 μl 10× ligase buffer, 10 μl of 500 μM ATP, and 7.5 μl of $dH_2O$. The kinase reaction was incubated at 37° C. for 30 minutes, and the reaction was terminated by incubation at 100° C. for 10 minutes. In order to ensure complete kination, the reaction was chilled on ice, 2 μl of 0.2M DDT, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing about 150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The annealed linker had the following structure:

The linker was stored at −20° C. until use.

About ~8 μg of ~1.25 kb BanI fragment were added to and mixed with the ~50 μl of linker (about 500 picomoles), 1 μl of T4 DNA ligase (about 500 units), 10 μl of 10× ligase buffer, and 29 μl of $dH_2O$, and the resulting ligation reaction was incubated at 4° C. overnight. The ligation reaction was stopped by a 10 minute incubation at 65° C. The DNA was pelleted by adding sodium acetate to a final concentration of 0.3M, adding 2 volumes of ethanol, chilling in a dry ice-ethanol bath, and then centrifuging the solution.

The DNA pellet was dissolved in 10 μl of 10× ApaI reaction buffer (60 mM NaCl; 60 mM Tris-HCl, pH=7.4; 60 mM $MgCl_2$; and 60 mM 2-mercaptoethanol), 5 μl (about 50 units) of restriction enzyme ApaI, and 85 μl of $dH_2O$, and the reaction was placed at 37° C. for two hours. The reaction was then stopped and the DNA pelleted as above. The DNA pellet was dissolved in 10 μl of 10× HindIII reaction buffer, 5 μl (about 50 units) of restriction enzyme HindIII, and 85 μl of $dH_2O$, and the reaction was placed at 37° C. for two hours. After the HindIII digestion, the reaction mixture was loaded onto a 3.5% polyacrylamide gel, and the desired ~1.23 kb HindIII-ApaI restriction fragment was isolated in substantial accordance with the procedure described in Example 4A. Approximately 5 μg of the desired fragment were obtained, suspended in 10 μl of TE buffer, and stored at −20° C.

Fifty μl of plasmid pHC7 DNA were mixed with 5 μl (about 50 units) of restriction enzyme PSI, 10 μl of 10× PstI reaction buffer (1.0M NaCl; 100 mM Tris-HCl, pH=7.5; 100 mM $MgCl_2$; and 1 mg/ml BSA), and 35 μl of $dH_2O$ and incubated at 37° C. for two hours. The PstI-digested plasmid pHC7 DNA was then electrophoresed on a 3.5% polyacrylamide gel, and the desired ~0.88 kb fragment was purified in substantial accordance with the procedure described above. Approximately 5 μg of the desired fragment were obtained, suspended in 10 μl of TE buffer, and stored at −20° C.

About 5 μg of the ~0.88 kb PstI fragment were added to and mixed with about 50 μl of the following linker, which was constructed on an automated DNA synthesizer as described in Example 1:

About 1 μl of T4 DNA ligase (about 10 units), 10 μl 10× ligase buffer, and 29 μl $dH_2O$ were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10× ApaI reaction buffer, 5 μl (about 50 units) of restriction enzyme ApI, and 85 μl of $dH_2O$, and the reaction was placed at 37° C. for two hours. The reaction was then stopped and the DNA pelleted once again. The DNA pellet was dissolved in 10 μl 10× BglII reaction buffer (1M NaCl; 100 mM Tris-HCl, pH=7.4; 100 mM $MgCl_2$; 100 mM 2-mercaptoethanol; and 1 mg/ml BSA), 5 μl (about 50 units) of restriction enzyme BglII, and 85 μl glass distilled $dH_2O$, and the reaction was placed at 37° C. for two hours. After the BglII digestion, the reaction mixture was loaded onto a 3.5% polyacrylamide gel, and the desired ~0.19 kb ApaI-BglII restriction fragment was isolated in substantial accordance with the procedure described above. Approximately 1 μg of the desired fragment was obtained, suspended in 10 μl of TE buffer, and stored at –20° C.

Approximately 10 μg of plasmid pSV2gpt DNA (ATCC 37145) were dissolved in 10 μl of 10× HindIII reaction buffer, 5 μl (about 50 units) of restriction enzyme HindIII, and 85 μl of dH$_2$O, and the reaction was placed at 37° C. for 2 hours. The reaction mixture was then made 0.25M in sodium acetate, and after the addition of two volumes of ethanol and incubation in a dry ice-ethanol bath, the DNA was pelleted by centrifugation. The DNA pellet was dissolved in 10 μl of 10× BglII buffer, 5 μl (about 50 units) of restriction enzyme BglII, and 85 μl of dH$_2$O, and the reaction was placed at 37° C. for two hours. After the BglII digestion, the reaction mixture was loaded onto a 1% agarose gel, and the fragments were separated by electrophoresis. The gel was stained with ethidium bromide and viewed under UV light, and the band containing the desired ~5.1 kb HindIII-BglII fragment was cut from the gel and placed in dialysis tubing, and electrophoresis was continued until the DNA was electrophoresed out of the agarose. The buffer containing the DNA from the dialysis tubing was extracted with phenol and chloroform and then, the DNA was ethanol precipitated. The pellet was resuspended in 10 μl of TE buffer and constituted about 5 μg of the desired ~5.1 kb HindIII-BglII restriction fragment of plasmid pSV2gpt.

Two μl of the ~1.23 kb HindIII-ApaI restriction fragment, 3 μl of the ~0.19 kb ApaI-BglII fragment, and 2 μl of the ~5.1 kb HindIII-BglII fragment were mixed together and then incubated with 10 μl of 10× ligase buffer, 1 μl of T4 DNA ligase (about 500 units), and 82 μl of dH$_2$O at 16° C. overnight. The ligated DNA constituted the desired plasmid pSV2-HPC8; a restriction site and function map of the plasmid is presented in FIG. 7 of the accompanying drawings.

*E. coli* K12 RR1 (NRRL B-15210) cells were made competent for transformation in substantial accordance with the procedure described in Example 3. The ligated DNA prepared above was used to transform the cells, and aliquots of the transformation mix were plated on L-agar plates containing 100 μg/ml ampicillin. The plates were then incubated at 37° C. *E. coli* K12 RR1/pSV2-HPC8 transformants were verified by restriction enzyme analysis of their plasmid DNA.

B. Final Construction of Plasmid pL133

Fifty μg of plasmid pSV2-HPC8 were dissolved in 10 μl of 10× HindIII reaction buffer, 5 μl (about 50 units) of restriction enzyme HindIII, and 85 μl of dH$_2$O, and the reaction was incubated at 37° C. for two hours. After the HindIII digestion, the DNA was precipitated, and the DNA pellet was dissolved in 10 μl 10× SalI reaction buffer (1.5M NaCl; 60 mM Tris-HCl, pH=7.9; 60 mM MgCl$_2$; 60 mM 2-mercaptoethanol; and 1 mg/ml BSA), 5 μl (about 50 units) of restriction enzyme SalI, and 85 μl of dH$_2$O. The resulting SalI reaction mixture was incubated for 2 hours at 37° C. The HindIII-SalI-digested plasmid pSV2-HPC8 was loaded onto a 3.5% polyacrylamide gel and electrophoresed until the desired ~0.29 kb HindIII-SalI restriction fragment was separated from the other reaction products. The desired fragment was isolated from the gel in substantial accordance with the procedure described above in part A; about 2 μg of the fragment were obtained and suspended in 10 μl of TE buffer.

Fifty g of plasmid pSV2-HPC8 were dissolved in 10 μl of 10× BglII reaction buffer, 5 μl (about 50 units) of restriction enzyme BglII, and 85 μl of dH$_2$O, and the reaction was incubated at 37° C. for two hours. After the BglII digestion, the DNA precipitated, and the DNA pellet was dissolved in 10 μl of 10× SalI reaction buffer, 5 μl (about 50 units) of restriction enzyme SalI, and 85 μl of dH$_2$O. The resulting SalI reaction mixture was incubated for 2 hours at 37° C. The Sal I-BglI-digested plasmid pSV2-HPC8 was loaded onto a 3.5% polyacrylamide gel and electrophoresed until the desired ~1.15 kb SalI-BglII restriction fragment was separated from the other reaction products. The ~1.15 kb Sal I-BglII restriction fragment was isolated from the gel in substantial accordance with the procedure described above in part A; about 8 μg of fragment were obtained and suspended in 10 μl of TE buffer.

Approximately 10 μg of plasmid pSV2-β-globin DNA (NRRL B-15928) were dissolved in 10 μl of 10× HindIII reaction buffer, 5 μl (about 50 units) of restriction enzyme HindIII, and 85 μl of dH$_2$O, and the reaction was placed at 37° C. for 2 hours. The reaction mixture was then made 0.25M in sodium acetate, and after the addition of two volumes of ethanol and incubation in a dry ice-ethanol bath, the DNA was pelleted by centrifugation. The HindIII-digested plasmid pSV2 -β-globin DNA was dissolved in 10 μl of 10× BglII buffer, 5 μl (about 50 units) of restriction enzyme BglII, and 85 μl of dH$_2$O, and the reaction was placed at 37° C. for two hours. After the BglII digestion, the reaction mixture was loaded onto a 1% agarose gel, and the fragments were separated by electrophoresis. The desired ~4.2 kb HindIII-BglII restriction fragment was isolated from the gel in substantial accordance with the procedure described in Example 4A; about 5 μg of the desired fragment were obtained and suspended in 10 μl of TE buffer.

Two μl of the ~0.29 kb HindIII-SalI fragment of plasmid pSV2-HPC8, 2 μl of the ~1.15 kb SalI-BglII fragment of plasmid pSV2-HPC8, and 2 μl of the ~4.2 kb HindIII-BglII fragment of plasmid pSV2-β-globin were mixed together and ligated in substantial accordance with the procedure of part A above. The ligated DNA constituted the desired plasmid pL133; a restriction site and function map of plasmid pL133 is presented in FIG. 7 of the accompanying drawings. The desired *E. coli* K12 RR1/pL133 transformants were constructed in substantial accordance with the teaching of part A above, with the exception that plasmid pL133, rather than plasmid pSV2-HPCS, was used as the transforming DNA.

EXAMPLE 8

Construction of Plasmids pLPC and pLPC(GT)

A. Construction of Plasmid pLPC

About 20 μg of plasmid pBLcat DNA as prepared in Example 5A were dissolved in 10 μl of 10× HindIII buffer and 80 μl of dH$_2$O. About 10 μl (about 100 units) of restriction enzyme HindIII were added to the solution of plasmid pBLcat DNA, and the resulting reaction was incubated at 37° C. for 2 hours. The HindIII-digested plasmid pBLcat DNA was loaded onto a 1% agarose gel and electrophoresed until the ~0.87 kb HindIII restriction fragment that comprises the BK enhancer and Ad2 late promoter was separated from the other digestion products; then, the ~0.87 kb fragment was isolated and prepared for ligation in substantial accordance with the procedure of Example 4A. About 2 μg of the desired fragment were obtained and dissolved in 5 μl of TE buffer.

About 1.5 μg of plasmid pL133 DNA as prepared in Example 7 was dissolved in 2 μl of 10× HindIII buffer and 16 μl of dH$_2$O. About 1 μl (about 10 units) of restriction enzyme HindIII was added to the solution of DNA, and the resulting reaction was incubated at 37° C. for 2 hours. The DNA was then diluted to 100 µl with TE buffer and treated with calf-intestinal alkaline phosphatase in substantial accordance with the procedure in Example 3. The HindIII-digested plasmid pL133 DNA was extracted twice with phenol and once with chloroform, precipitated with ethanol, and resuspended in 10 µl of TE buffer.

About 5 µl of the ~0.87 kb HindIII restriction fragment of plasmid pBLcat were added to the 1.5 µl of HindIII-digested plasmid pL133, and then, 1 µl of 10× ligase buffer, 1 µl (about 1000 units) of T4 DNA ligase, and 1.5 µl of dH$_2$O were added to the solution of DNA, and the resulting reaction was incubated at 16° C. overnight. The ligated DNA constituted the desired plasmid pLPC.

The ligated DNA was used to transform *E. coli* K12 HB101 in substantial accordance with the procedure of Example 3. The transformed cells were plated on L-agar containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only one of which yields plasmid pLPC.

B. Construction of Plasmid pLPC(GT)

Plasmid pLPC(GT) is prepared by the same procedures as described in part A except that the ~0.93 kb HindIII fragment of plasmid pBL(GT)cat is used in the construction instead of the ~0.87 kb HindIII fragment of plasmid pBLcat to yield the desired plasmid pLPC(GT). The ~0.93 kb HindIII restriction fragment that encodes the BK enhancer, the poly-GT element and the Ad2 late promoter can be inserted into HiDdIII-digested plasmid pL133 in one of two orientations, only one of which yields plasmid pLPC(GT). A restriction site and function map of plasmid pLPC(GT) is presented in FIG. 8 of the accompanying drawings. The only difference between plasmids pLPC and pLPC(GT) is the presence of a poly-GT element in plasmid pLPC(GT).

Alternatively, plasmid pLPC(GT) is prepared by inserting a poly-GT element into the unique XhoI site in plasmid pLPC, between the BK enhancer and the Ad2 late promoter, in substantial accordance with the procedure of Example 4B.1.

EXAMPLE 9

Construction of Plasmids pLPC4, pLPC5, pLPC4(GT) and pLPC5(GT)

A. Construction of Plasmids pLPC4 and pLPC5

About 1 µg (1 µl) of the BK virus DNA prepared as in Example 2 and 1 µg (1 µl) of plasmid pLPC prepared as in Example 8A were dissolved in 2 µl of 10× EcoRI buffer (1.0M Tris-HCl, pH 7.5; 0.5M NaCl; 50 mM MgCl$_2$; and 1 mg/ml BSA) and 14 µl of dH$_2$O. Two µl (about 10 units) of restriction enzyme EcoRI were added to the solution of DNA, and the resulting reaction was incubated at 37° C. for 2 hours. The EcoRI-digested mixture of BK virus and plasmid pLPC DNA was extracted once with buffered phenol and once with chloroform. Then, the DNA was collected by adjusting the NaCl concentration to 0.25M, adding two volumes of ethanol, incubating the solution in a dry ice-ethanol bath for 2 minutes, and centrifuging the solution to pellet the DNA. The supernatant was discarded, and the DNA pellet was rinsed with 70% ethanol, dried, and resuspended in 12 µl of TE buffer.

About 13 µl of dH$_2$O and 3 µl of 10× ligase buffer were added to the EcoRI-digested mixture of BK virus and plasmid pLPC DNA. Two µl (about 100 units) of T4 DNA ligase were added to the solution of DNA, and the resulting reaction was incubated at 16° C. for 2 hours. The ligated DNA constituted the desired plasmids pLPC4 and pLPC5, which differ only with respect to the orientation of the inserted BK virus DNA.

The ligated DNA constituted the desired plasmids pLPC4 and pLPC5 and was used to transform *E. coli* K12 HB101 competent cells in substantial accordance with the procedure of Example 3. The transformed cells were plated on L-agar containing 100 µg/ml ampicillin. The *E. coli* K12 HB101/pLPC4 and *E. coli* K12 HB101/pLPC5 transformants were identified by their ampicillin-resistant phenotype and by restriction enzyme analysis of their plasmid DNA.

B. Construction of Plasmids pLPC4(GT) and pLPC5(GT)

Plasmids pLPC4(GT) and pLPC5(GT) are prepared by the same procedures as described in part A above for plasmids pLPC4 and pLPC5, except that plasmid pLPC(GT) prepared as in Example 8B is used in the constructions instead of plasmid pLPC. Alternatively, plasmids pLPC4(GT) and pLPC5(GT) are prepared by inserting a poly-GT element into the unique XhoI site of plasmids pLPC4 and pLPC5, respectively, in substantial accordance with the procedure of Example 4B.1. A restriction site and function map of plasmid pLPC4(GT) is presented in FIG. 9 of the accompanying drawings.

EXAMPLE 10

Construction of Plasmids pLPChyg1, pLPChyg2, pLPChyg1(GT) and pLPChyg2(GT)

A. Construction of Plasmids pLPChyg1 and pLPChyg2

*E. coli* K12 RR1/pSV2hyg cells are obtained from the Northern Regional Research Laboratory under the accession number NRRL B-18039. Plasmid pSV2hyg DNA is obtained from the cells in substantial accordance with the procedure of Example 3. A restriction site and function map of plasmid pSV2hyg is presented in FIG. 10 of the accompanying drawings.

About 10 µg (in 10 µl of TE buffer) of plasmid pSV2hyg were added to 2 µl of 10× BamHI buffer and 6 µl of dH$_2$O. Two µl (about 20 units) of restriction enzyme BamHI were added to the solution of DNA, and the resulting reaction was incubated at 37° C. for 2 hours. The reaction was extracted first with phenol and then extracted twice with chloroform. The BamHI-digested plasmid pSV2hyg DNA was loaded onto a 1% agarose gel, and the ~2.5 kb hygromycin resistance gene-containing restriction fragment was isolated in substantial accordance with the procedure described in Example 4A.

About 5 µl of 10× Klenow buffer (0.2 mM in each of the four dNTPs; 0.5M Tris-HCl, pH=7.8; 50 mM MgCl$_2$; 0.1M 2-mercaptoethanol; and 100 µg/ml BSA) and 35 µl of dH$_2$O were added to the solution of BamHI-digested plasmid pSV2hyg DNA, and then, about 25 units of Klenow enzyme (about 5 µl, as marketed by BRL) were added to the mixture of DNA, and the resulting reaction was incubated at 16° C. for 30 minutes. The Klenow-treated, BamHI-digested plasmid pSV2hyg DNA was extracted once with phenol and once with chloroform and then precipitated with ethanol.

About 2 μg of the desired fragment were obtained and suspended in 5 μl of TE buffer.

About 10 μg (10 μl) of plasmid pLPC DNA were added to 2 μl of 10× StuI buffer and 6 μl of dH$_2$O. Two μl (about 10 units) of restriction enzyme StuI were added to the solution of DNA, and the resulting reaction was incubated at 37° C. for 2 hours. The StuI-digested plasmid pLPC DNA was precipitated with ethanol, collected by centrifugation, and resuspended in 2 μl of 10× NdeI buffer (1.5M NaCl; 0.1M Tris-HCl, pH=7.8; 70 mM MgCl$_2$; 60 mM 2-mercaptoethanol; and 1 mg/ml BSA) and 16 μl of dH$_2$O. Two 1 (about 10 units) of restriction enzyme NdeI were added to the solution of StuI-digested DNA, and the resulting reaction was incubated at 37° C. for 2 hours.

The NdeI-StuI-digested plasmid pLPC DNA was precipitated with ethanol, collected by centrifugation, and resuspended in 5 μl of 10× Klenow buffer and 40 μl of dH$_2$O. Five 1 (about 25 units) of Klenow enzyme were added to the solution of DNA, and the resulting reaction was incubated at 16° C. for 30 minutes. After the Klenow reaction, the reaction mixture was loaded onto a 1% agarose gel, and the ~5.82 kb NdeI-StuI restriction fragment was isolated from the gel. About 5 μg of the desired fragment were obtained and suspended in 5 μl of TE buffer.

About 2 μl of the ~2.5 kb Klenow-treated BamHI restriction fragment of plasmid pSV2hyg were mixed with about 1 μl of the ~5.82 kb Klenow-treated NdI-StuI restriction fragment of plasmid pLPC, and about 3 μl of 10× ligase buffer, 2 μl of T4 DNA ligase (about 1000 units), 1 μl of T4 RNA ligase (about 1 unit), and 14 μl of dH$_2$O were added to the solution of DNA. The resulting reaction was incubated at 16° C. overnight. The ligated DNA constituted the desired plasmids pLPChyg1 and pLPChyg2, which differ only with respect to the orientation of the ~2.5 kb Klenow-treated, BamHI restriction fragment of plasmid pSV2hyg. The ligated DNA was used to transform *E. coli* K12 HB101 in substantial accordance with the procedure of Example 3. The desired *E. coli* K12 HB101/pLPChyg1 and *E. coli* K12 HB101/pLPChyg2 transformants were plated on L-agar containing ampicillin and identified by restriction enzyme analysis of their plasmid DNA.

B. Construction of Plasmids pLPhyg1(GT) and pLPChyg2(GT)

A poly-GT element is inserted into the unique XhoI site in plasmid pLPChyg1 or pLPChyg2, between the BK enhancer and the Ad2 late promoter, in substantial accordance with the procedure of Example 4B.1. The XhoI-digested poly-GT element and XhoI-digested plasmid pLPChyg1 or pLPChyg2 DNA are ligated and the ligated DNA constitutes the desired plasmids pLPChyg1(GT) and pLPChyg2(GT), respectively. A restriction site and function map of plasmid pLPChyg1(GT) is presented in FIG. 11 of the accompanying drawings.

EXAMPLE 11

Construction of Plasmid pBW32

A. Construction of Intermediate Plasmid pTPA103

Plasmid pTPA102 comprises the coding sequence of human tissue plasminogen activator (TPA). Plasmid pTPA102 can be isolated from *E. coli* K12MM294/pTPA102, a strain available from the Northern Regional Research Laboratory under the accession number NRRL B-15834. A restriction site and function map of plasmid pTPA102 is presented in FIG. 12 of the accompanying drawings. Plasmid pTPA102 DNA is isolated from *E. coli* K12 MM294/pTPA102 in substantial accordance with the procedure of Example 3.

About 50 μg of plasmid pTPA102 (in about 50 μl of TE buffer) were added to 10 μl of 10× TthIIII buffer (0.5M NaCl; 80 mM Tris-HCl, pH=7.4; 80 mM MgCl$_2$; 80 mM 2-mercaptoethanol; and 1 mg/ml BSA) and.80 μl of dH$_2$O. Ten μl (about 50 units) of restriction enzyme TthIIII were added to the solution of DNA, and the resulting reaction was incubated at 65° C. for 2 hours. The reaction mixture was loaded onto a 1% agarose gel, and the ~4.4 kb TthIIII restriction fragment that comprises the TPA coding sequence was isolated from the gel. The other digestion products, 3.1 kb and 0.5 kb restriction fragments, were discarded. About 10 μg of the desired ~4.4 kb TthIIII restriction fragment were obtained and suspended in 10 μl of TE buffer.

About 5 μl of 10× Klenow buffer and 30 μl of dH$_2$O were added to the solution comprising the ~4.4 kb TthIIII restriction fragment, and after the further addition of 5 μl of Klenow enzyme (about 5 units), the reaction mixture was incubated at 16° C. for 30 minutes. After the Klenow reaction, the DNA was precipitated with ethanol and resuspended in 3 μl of 10× ligase buffer and 14 μl of dH$_2$O.

BamHI linkers (New England Biolabs), which had the following sequence:

were kinased and prepared for ligation by the following procedure. Four μl of linkers (about 2 μg) were dissolved in 20.15 μl of dH$_2$O and 5 μl of 10× kinase buffer (500 mM Tris-HCl, pH=7.6 and 100 mM MgCl$_2$), incubated at 90° C. for two minutes, and then cooled to room temperature. Five μl of γ-$^{32}$P-ATP (about 20 μCi), 2.5 μl of 1M DTT, and 5 μl of polynucleotide kinase (about 10 units) were added to the mixture, which was then incubated at 37° C. for 30 minutes. Then, approximately 3.35 μl of 10 mM ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb TthIIII restriction fragment, and after the addition of 2 μl of T4 RNA ligase (about 2 units), the ligation reaction was incubated overnight at 4° C. The ligated DNA was precipitated with ethanol and resuspended in 5 μl of 10× HindIII buffer and 40 μl of dH$_2$O. Five HI (about 50 units) of restriction enzyme HindIII were added to the solution of DNA, and the resulting reaction was incubated at 37° C. for 2 hours.

The HindIII-digested DNA was precipitated with ethanol and resuspended in 10 μl of 10× BamHI buffer and 90 μl of dH$_2$O. Ten μl (about 100 units) of restriction enzyme BamHI were added to the solution of DNA, and the resulting reaction was incubated at 37° C. for 2 hours. After the BamHI digestion, the reaction mixture was loaded onto a 1% agarose gel, and the ~2.0 kb BamHI HindIII restriction fragment was isolated from the gel in substantial accordance with the procedure of Example 4A. About 4 g of the desired fragment were obtained in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the *E. coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102, which can be isolated from *E. coli* K12MM294/pTPA102 (NRRL B-15834). Plasmid pKC7 and plasmid pTPA102 DNA can be obtained from the aforementioned cell lines in substantial accordance with the procedure of Example 3. This ~0.29 kb EcoRI-ClaI restriction fragment of plasmid pTPA102 comprises the transcription activating sequence and most of the translation activating sequence of the *E. coli* trp gene and has the sequence depicted below:

enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel; about 1 μg of the desired fragment was obtained, suspended in 5 μl of TE buffer, and added to the solution of EcoRI-ClaI-digested plasmid pKC7 DNA prepared as described above. Two μl (about 1000 units) of T4 DNA ligase were then added to the mixture of DNA, and the resulting ligation reaction was

```
              10          20          30          40          50
5'-AATTCACGCT  GTGGTGTTAT  GGTCGGTGGT  CGCTAGGGTG  CCGACGCGCA
   ||||||      ||||||||||  ||||||||||  ||||||||||  ||||||||||
3'-GTGCGA      CACCACAATA  CCAGCCACCA  GCGATCCCAC  GGCTGCGCGT 60          70          80          90          100
   TCTCGACTGC  ACGGTGCACC  AATGCTTCTG  GCGTCAGGCA  GCCAATCGGA
   ||||||||||  ||||||||||  ||||||||||  ||||||||||  ||||||||||
   AGAGCTGACG  TGCCACGTGG  TTACGAAGAC  CGCAGTCCGT  CGGTTAGCCT 110         120         130         140         150
   AGCTGTGGTA  TGGCTGTGCA  GGTCGTATAA  TCACCGCATA  ATTCGAGTCG
   ||||||||||  ||||||||||  ||||||||||  ||||||||||  ||||||||||
   TCGACACCAT  ACCGACACGT  CCAGCATATT  AGTGGCGTAT  TAAGCTCAGC 160         170         180         190         200
   CTCAAGGCGC  ACTCCCGTTC  CGGATAATGT  TTTTTGCTCC  GACATCATAA
   ||||||||||  ||||||||||  ||||||||||  ||||||||||  ||||||||||
   GAGTTCCGCG  TGAGGGCAAG  GCCTATTACA  AAAAACGAGG  CTGTAGTATT 210         220         230         240         250
   CGGTTCCGGC  AAATATTCTG  AAATGAGCTG  TTGACAATTA  ATCATCGAAC
   ||||||||||  ||||||||||  ||||||||||  ||||||||||  ||||||||||
   GCCAAGGCCG  TTTATAAGAC  TTTACTCGAC  AACTGTTAAT  TAGTAGCTTG 260         270         280         287
   TAGTTAACTA  GTACGCAAGT  TCTCGTAAAA  AGGGTAT-3'
   ||||||||||  ||||||||||  ||||||||||  |||||||
   ATCAATTGAT  CATGCGTTCA  AGAGCATTTT  TCCCATAGC-5'
```

Thus, to construct plasmid pRC, about 2 μg of plasmid pKC7 in 10 μl of TE buffer were added to 2 μl of 10× ClaI buffer (0.5M NaCl; 60 mM Tris-HCl, pH 7.9, 60 mM $MgCl_2$; and 1 mg/ml BSA) and 6 μl of $dH_2O$. Two μl (about 10 units) of restriction enzyme ClaI were added to the solution of plasmid pKC7 DNA, and the resulting reaction was incubated at 37° C. for 2 hours. The ClaI-digested plasmid pKC7 DNA was precipitated with ethanol and resuspended in 2 μl of 10× EcoRI buffer and 16 μl of $dH_2O$. Two μl (about 10 units) of restriction enzyme EcoRI were added to the pKC7 DNA, and the resulting reaction was incubated at 37° C. for 2 hours.

The EcoRI-ClaI-digested plasmid pKC7 DNA was extracted once with phenol and then twice with chloroform. The DNA was then precipitated with ethanol and resuspended in 3 μl of 10× ligase buffer and 20 μl of $dH_2O$. A restriction site and function map of plasmid solution of ClaI-digested plasmid pKC7 can be obtained from Maniatis et al., *Molecular Cloning* (Cold Spring Harbor Laboratory, 1982), page 8.

About 20 g of plasmid pTPA102 in about 20 μl of TE buffer were added to 10 μl of 10× ClaI buffer and 60 μl of $dH_2O$. Ten μl (about 50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10× EcoRI buffer and 80 μl of $dH_2O$. Ten 1 (about 50 units) of restriction incubated at 16° C. for 2 hours. The ligated DNA constituted the desired plasmid pRC DNA.

The ligated DNA was used to transform *E. coli* K12 HB101 competent cells in substantial accordance with the procedure of Example 3. The transformed cells were plated on L-agar containing 100 μg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 3.

About 2 g of plasmid pRC DNA in 2 μl of TE buffer were added to 2 μl of 10× HindIII buffer and 16 μl of $dH_2O$. Two 1 (about 10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10× BamHI buffer and 16 μl of $dH_2O$. Two 1 (about 10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10× ligase buffer and 20 μl of $dH_2O$. Approximtely 4 g (in about 5 μl of TE buffer) of ~2.0 kb HindIII-BamHI restriction fragment of plasmid pTPA102 were then added to the solution of Bam HI-HindIII-digested plasmid pRC DNA. Two μl (about 1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms E. coli at a lower frequency than closed circular DNA. To digest the ligated DNA, the DNA was first precipitated with ethanol and then resuspended in 2 μl of 10× NcoI buffer (1.5M NaCl; 60 mM Tris-HCl, pH =7.8; 60 mM MgCl$_2$; and 1 mg/ml BSA) and 16 μl of dH$_2$O. Two μl (about 10 units) of restriction enzyme NcoI were added to the solution of DNA, and the resulting reaction was incubated at 37° C. for 2 hours.

The ligated and then NcoI-digested DNA was used to transform E. coli K12 RV308 (NRRL B-15624). E. coli K12 RV308 cells were made competent and transformed in substantial accordance with the procedure of Example 3. The transformation mixture was plated on L-agar containing 100 μg/ml ampicillin. The ampicillin-resistant transformants were tested for sensitivity to kanamycin, because plasmid pRC confers kanamycin resistance, but plasmid pTPA103 does not. The ampicillin-resistant, kanamycin-sensitive transformants were then used to prepare plasmid DNA, and the plasmid DNA was examined by restriction enzyme analysis to identify the E. coli K12 RV308/pTPA103 transformants. A restriction site and function map of plasmid pTPA103 is presented in FIG. 12 of the accompanying drawings. Plasmid pTPA103 DNA was isolated from the E. coli K12 RV308/pTPA103 cells in substantial accordance with the procedure of Example 3.

B. Construction of Intermediate Plasmid pBW25

About 1 μg of plasmid pTPA103 DNA in 1 μl of TE buffer was added to 2 μl of 10× BglII buffer and 16 μl of dH$_2$O. One μl (about 5 units) of restriction enzyme BglII was added to the solution of plasmid pTPA103 DNA, and the resulting reaction was incubated at 37° C. for 2 hours. The BglII-digested plasmid pTPA103 DNA was precipitated with ethanol and resuspended in 5 μl of 10× Klenow buffer and 44 μl of dH$_2$O. One μl of Klenow enzyme (about 1 unit) was added to the solution of BglII-digested plasmid pTPA103 DNA, and the resulting reaction was incubated at 16° C. for 2 hours. The Klenow-treated, BglII-digested plasmid pTPA103 DNA was precipitated with ethanol and resuspended in 3 μl of 10× ligase buffer and 22 μl of dH$_2$O.

About 2 μl (0.2 μg) of unkinased NdeI linkers (New England Biolabs) of sequence:

were added to the solution of Klenow-treated, BglII-digested plasmid pTPA103 DNA, together with 2 μl (about 1000 units) of T4 DNA ligase and 1 μl (about 2 units) of T4 RNA ligase, and the resulting ligation reaction was incubated at 4° C. overnight. The ligated DNA constituted plasmid pTPA103derNdeI, which is substantially similar to pTPA103, except plasmid pTPA103derNdeI has an NdeI recognition sequence where plasmid pTPA103 has a BglII recognition sequence.

The ligated DNA was used to transform E. coli K12 RV308 competent cells in substantial accordance with the procedure described in Example 3. The transformed cells were plated on L-agar containing ampicillin, and the E. coli K12 RV308/pTPA103derNdeI transformants were identified by restriction enzyme analysis of their plasmid DNA. Plasmid pTPA103derNdeI DNA was isolated from the transformants for use in subsequent constructions in substantial accordance with the procedure of Example 3.

About 10 μg of plasmid pTPA103derNdeI DNA in 10 μl of TE buffer were added to 2 μl of 10× AvaII buffer (0.6 M NaCl; 60 mM Tris-HCl, pH=8.0; 0.1 M MgCl$_2$; 60 mM 2-mercaptoethanol; and 1 mg/ml BSA) and 6 μl of dH$_2$O. Two μl (about 10 units) of restriction enzyme AvaII were added to the DNA, and the resulting reaction was incubated at 37° C. for 2 hours. The AvaII-digested DNA was loaded onto a 1% agarose gel and electrophoresed until the ~1.4 kb restriction fragment was separated from the other digestion products. The ~1.4 kb AvaII restriction fragment of plasmid pTPA103derNdeI was isolated from the gel; about 2 μg of the desired fragment were obtained and suspended in 5 μl of TE buffer.

Five μl of 10× Klenow buffer, 35 μl of dH$_2$O, and 5 μl (about 5 units) of Klenow enzyme were added to the solution of ~1.4 kb AvaII restriction fragment, and the resulting reaction was incubated at 16° C. for thirty minutes. The Klenow-treated DNA was precipitated with ethanol and resuspended in 3 μl of 10× ligase buffer and 14 μl of dH$_2$O.

About 2 μg of HpaI linkers of sequence:

were kinased in substantial accordance with the procedure of part A above. About 10 μl of the kinased linkers were added to the solution of Klenow-treated, ~1.4 kb AvaII restriction fragment of plasmid pTPA103derNdeI together with 2 μl (about 1000 units) of T4 DNA ligase and 1 μl (about 1 unit) of T4 RNA ligase, and the resulting reaction was incubated at 16° C. overnight.

The ligated DNA was extracted once with phenol, extracted twice with chloroform, precipitated with ethanol, and resuspended in 2 μl of 10× EcoRI buffer and 16 μl of dH$_2$O. Two μl (about 10 units) of restriction enzyme EcoRI were added to the solution of DNA, and the resulting reaction was incubated at 37° C. for 2 hours. The EcoRI-digested DNA was extracted once with phenol, extracted twice with chloroform, precipitated with ethanol, and resuspended in 3 μl of 10× ligase buffer and 20 μl of dH$_2$O. The fragment, which is ~770 bp in size and encodes the trpPO and the amino-terminus of TPA, thus prepared had one EcoRI-compatible end and one blunt end and was ligated into EcoRI-SmaI-digested plasmid pUC19 to form plasmid pUC19TPAFE as follows.

About 2 μl of plasmid pUC19 (available from BRL) were dissolved in 2 μl of 10× SmaI buffer (0.2M KCl; 60 mM Tris-HCl, pH=8.0; 60 mM MgCl$_2$; 60 mM 2-mercaptoethanol; and 1 mg/ml BSA) and 16 μl of dH$_2$O. Two μl (about 10 units) of restriction enzyme SmaI were added to the solution of DNA, and the resulting reaction was incubated at 25° C. for 2 hours. The SmaI-digested plasmid pUC19 DNA was precipitated with ethanol, collected by centrifugation, and resuspended in 2 μl of 10× EcoRI buffer and 16 μl of dH$_2$O. Two μl (about 10 units) of restriction enzyme EcoRI were added to the solution of SmaI-digested plasmid pUC19 DNA, and the resulting reaction was incubated at 37° C. for 2 hours. The EcoRI-SmaI-digested plasmid pUC19 DNA was extracted once with phenol, extracted twice with chloroform, and resuspended in 5 μl of TE buffer.

The EcoRI-SmaI-digested plasmid pUC19 DNA was added to the solution containing the ~770 bp EcoRI-blunt end restriction fragment derived from plasmid pTPA103derNdeI. Two μl (about 1000 units) of T4 DNA ligase were added to the mixture of DNA, and the resulting reaction was incubated at 16° C. overnight. The ligated DNA constituted the desired plasmid pUC19TPAFE. A restriction site and function map of plasmid pUC19TPAFE is presented in FIG. 12 of the accompanying drawings.

The multiple-cloning site of plasmid pUC19, which comprises the EcoRI and SmaI recognition sequences utilized in the construction of plasmid pUC19TPAFE, is located within the coding sequence for the lacZ α fragment. Expression of the lacZ α fragment in cells that contain the lacZ ΔM15 mutation, a mutation in the lacZ gene that encodes β-galactosidase, allows those cells to express a functional β-galactosidase molecule and thus allows those cells to hydrolyze X-Gal (5-bromo-4-chloro-3-indolyl-β-D-galactopyranoside), a colorless compound, to its indigo-colored hydrolysis product in the presence of the inducer IPTG (isopropylthiogalactoside). Insertion of DNA into the multiple-cloning site of plasmid pUG19 interrupts the coding sequence for the IaqZ e fragment, and cells with the lacZ ΔM15 mutation that host such a plasmid are unable to hydrolyze X-Gal (such that the colonies are white, not indigo). The ligated DNA that constituted plasmid pUC19TPAFE was used to transform *E. coli* K12 RR1ΔM15 (NRRL B-15440) cells made competent for transformation in substantial accordance with the procedure of Example 3.

The transformed cells were plated on L-agar containing 100 μg/ml ampicillin; 40 μg/ml X-Gal; and 1 mM IPTG. Colonies that failed to exhibit the indigo color were subcultured and used to prepare plasmid DNA; the *E. coli* K12 RR1ΔM15/pUC19TPAFE transformants were identified by restriction enzyme analysis of their plasmid DNA. Plasmid pUC19TPAFE DNA was isolated from the *E. coli* K12 RRΔM15/pUC19TPAFE cells for use in subsequent constructions in substantial accordance with the procedure of Example 3.

About 7 μg of plasmid pUC19TPAFE in 20 μl of TE buffer were added to 10 μl of 10× HpaI buffer (0.2M KCl; 0.1M Tris-HCl, pH=7.4; and 0.1M $MgCl_2$) and 70 μl of $dH_2O$. Three μl (about 6 units) of restriction enzyme HpaI were added to the solution of plasmid pUC19TPAFE DNA, and the resulting reaction was incubated at 37° C. for 20 minutes; the short reaction period was designed to yield a partial HpaI digest. The reaction was adjusted to 150 μl of 1× BamHI buffer (150 mM NaCl; 10 mM Tris-HCl, pH=8.0; and 10 mM $MgCl_2$; raising the salt concentration inactivates HpaI). One μl (about 16 units) of restriction enzyme BamHI were added to the solution of HpaI (partial) digest of DNA, and the resulting reaction was incubated at 37° C. for 90 minutes.

The BamHI -HpaI (partial) digest of plasmid pUC19TPAFE DNA was concentrated by ethanol precipitation, loaded onto a 1.5% agarose gel, and the ~3.42 kb HpaI-BamHI restriction fragment that comprises the replicon, β-lactamase gene, and all of the TPA-encoding DNA of plasmid pUCATPAFE was isolated from the gel in substantial accordance with the procedure of Example 4A. About 1 μg of the desired fragment was obtained and suspended in 20 μl of TE buffer.

About 10 μg of plasmid pTPA103 in 10 μl of TE buffer were dissolved in 10 μl of 10× ScaI buffer (1.0M NaCl; 60 mM Tris-HCl, pH=7.4; 60 mM $MgCl_2$; 10 mM DTT; and 1 mg/ml BSA) and 80 μl of $dH_2O$. Three μl (about 18 units) of restriction enzyme ScaI were added to the solution of plasmid pTPA103 DNA, and the resulting reaction was incubated at 37° C. for 90 minutes. The reaction volume was adjusted to 150 μl of 1× BamHI buffer, and 1 μl (about 16 units) of restriction enzyme BamHI was added to the mixture, which was then incubated at 37° C. for 90 minutes. The DNA was precipitated with ethanol, collected by centrifugation, and resuspended in preparation for electrophoresis. The ScaI-BamHI-digested plasmid pTPA103 DNA was loaded onto a 1.5% agarose gel and electrophoresed until the ~1.0015 kb ScaI-BamHI restriction fragment was separated from the other digestion products. The ~1.0015 ScaI-BamHI restriction fragment that comprises the TPA carboxy-terminus-encoding DNA of plasmid pTPA103 was isolated from the gel as described above; about 0.5 μg of the desired fragment were obtained and dissolved in 20 μl of $dH_2O$.

About 2 μl of the ~3.42 kb BamHI-HpaI restriction fragment of plasmid pUC19TPAFE were added to 2 μl of the ~1.0015 kb ScaI-BamHI restriction fragment of plasmid pTPA103 together with 2 μl of 10× T4 DNA ligase buffer and 1 μl (about 1 Weiss unit; the ligase was obtained from Promega Biotec, 2800 S. Fish Hatchery Road, Madison, Wis. 53711) of T4 DNA ligase, and the resulting reaction was incubated at 16° C. overnight. The ligated DNA constituted the desired plasmid pBW25. A restriction site and function map of plasmid pBW25 is presented in FIG. 14 of the accompanying drawings.

The ligated DNA was used to transform *E. coli* K12 JM105 (available from BRL) that were made competent for transformation in substantial accordance with the procedure of Example 3, except that 50 mM $CaCl_2$ was used in the procedure. The transformed cells were plated on Brain Heart Infusion agar (BHI) (Difco Laboratories, Detroit, Mich.) containing 100 μg/ml ampicillin, and the *E. coli* K12 JM105/ pBW25 transformants were identified by restriction enzyme analysis of their plasmid DNA. Digestion of plasmid pBW25 with restriction enzyme EcoRI yields ~3.38 kb and ~1.008 kb restriction fragments. Plasmid pBW25 is prepared for use in subsequent constructions in substantial accordance with the procedure of Example 3.

C. Site-Specific Mutagenesis of the TPA Coding Region and Construction of Plasmid pBW28

About 5 μg of plasmid pBW25 in 10 μl of $dH_2O$ were added to 10 μl of 10× HindIII reaction buffer and 80 μl of $dH_2O$. One μl (about 20 units) of restriction enzyme HindIII was added to the solution of plasmid pBW25 DNA, and the resulting reaction was incubated at 37° C. for 90 minutes. Three μl (about 24 units) of restriction enzyme EcoRI and 10 μl of 1M Tris-HCl, pH=7.6, were added to the solution of HindIII-digested plasmid pBW25 DNA, and the resulting reaction was incubated at 37° C. for 90 minutes. The EcoRI-HindIII-digested plasmid pBW25 DNA was concentrated by ethanol precipitation, loaded onto a 1.5% agarose gel, and electrophoresed until the ~810 bp Ec.ORI-HindIII restriction fragment was separated from the other digestion products. About 0.5 μg of the ~810 bp EcoRI-HindIII restriction fragment was isolated from the gel in substantial accordance with the procedure of Example 4A, prepared for ligation, and resuspended in 20 μl of $dH_2O$.

About 4.5 μg of the replicarive form (RF) of M13mp8 DNA (available from New England Biolabs) in 35 μl of $dH_2O$ were added to 10 μl of 10× HindIII buffer and 55 μl of $dH_2O$. One μl (about 20 units) of restriction enzyme HindIII was added to the solution of M13mp8 DNA, and the resulting reaction was incubated at 37° C. for 1 hour. Three μl (about 24 units) of restriction enzyme EcoRI and 10 μl of 1M Tris-HCl, pH=7.6, were added to the solution of HindIII-digested M13mp8 DNA, and the resulting reaction was incubated at 37° C. for 1 hour. The HindIII-EcoRI-digested M13mp8 DNA was collected by ethanol precipitation, resuspended in preparation for agarose gel electrophoresis, and the large restriction fragment isolated by gel electrophoresis as described above. About 1 μg of the large EcoRI-HindIII restriction fragment of M13mp8 was obtained and suspended in 20 μl of dH$_2$O. About 2 μl of the large EcoRI-HindIII restriction fragment of M13mp8, 2 μl of 10× T4 DNA ligase buffer, 12 μl of dH$_2$O and 1 μl (about 1 Weiss unit) of T4 DNA ligase were added to 3 μl of the ~810 bp EcoRI-HindIII restriction fragment of plasmid pBW25, and the resulting ligation reaction was incubated at 16° C. overnight.

E. coli JM103 cells (available from BRL) were made competent and transfected with the ligation mix in substantial accordance with the procedure described in the BRL M13 Cloning/'Dideoxy' Sequencing Instruction Manual, except that the amount of DNA used per transfection was varied. Recombinant plaques were identified by insertional inactivation of the β-galactosidase α-fragment-encoding gene, which results in the loss of the ability to cleave X-Gal to its indigo-colored cleavage product. For screening purposes, each of six white plaques were picked into 2.5 ml of L broth, to which was added 0.4 ml of E. coli K12 JM103 in logarithmic growth phase, which had been cultured in minimal media stock to insure retention of the F episome that carries proAB. The 2.5 ml plaque-containing cell suspensions were incubated in an air-shaker at 37° C. for 8 hours. Cells from 1.5 ml aliquots were pelleted and RF DNA isolated in substantial accordance with the alkaline miniscreen procedure of Birnboim and Doly, 1979, *Nuc. Acids Res.* 7:1513. The remainder of each culture was stored at 4° C. for stock. The desired phage, designated MP8BW26, contained the ~810 bp EcoRI-HindIII restriction fragment of plasmid pBW25 ligated to the ~7.2 kb EcoRI-HindIII restriction fragment of M13mp8.

About fifty ml of log phase E. coli JM103 were infected with MP8BW26 and incubated in an air-shaker at 37° C. for 18 hours. The infected cells were pelleted by low speed centrifugation, and single-stranded MP8BW26 DNA was prepared from the culture supernatant by scaling up the procedure given in the Instruction Manual. Single-stranded MP8BW26 was mutagenized in substantial accordance with the teaching of Adelman et al., 1983, *DNA* 2(3):183–193, except that the Klenow reaction was done at room temperature for 30 minutes, then at 37° C. for 60 minutes, then a 10° C. for 18 hours. In addition, the S1 treatment was done at 20° C., the salt concentration of the buffer was one-half that recommended by the manufacturer, and the M13 sequencing primer (BRL) was used. The synthetic oligodeoxyribonucleotide primer used to delete the coding sequence for amino acid residues 87 through 261 of native TPA was

5'-GGGAAGTGCTGTGAAATATCCACCTGCGGCCTGAGA-3'.

The resulting mutagenesis mix was used to transfect E. coli K12 JM 103 in substantial accordance with the infection procedure described above. Desired mutants were identified by restriction enzyme analysis of RF DNA and by Maxam and Gilbert DNA sequencing. The desired mutant, which had the coding sequence for amino acid residues 87 through 261 of native TPA deleted, was designated MPSBW27.

To construct plasmid pBW28, a variety of DNA fragments are needed. The first of these fragments was obtained by adding about 20 μg of RF MPSBW27 DNA in 20 μl of dH$_2$O to 10 μl of 10× NdeI buffer and 60 μl of dH$_2$O. Ten μl (about 50 units) of restriction enzyme NdeI were added to the mixture of MPSBW27 DNA, and the resulting reaction was incubated at 37° C. for 2 hours. The NdeI-digested MPSBW27 DNA was precipitated with ethanol, collected by centrifugation, and resuspended in 10 μl of 10× EcoRI buffer and 90 μl of dH$_2$O. Ten μl (~50 units) of restriction enzyme EcoRI were added to the solution of NdeI-digested plasmid MP8BW27 DNA, and the resulting reaction was incubated at 37° C. for 2 hours. The EcoRI-NdeI-digested MP8BW27 DNA was electrophoresed on an agarose gel until the ~560 bp NdeI-EcoRI restriction fragment, which contains the portion of TPA coding sequence that spans the site of deletion, was separated from the other digestion products. The ~560 bp NdeI-EcoRI restriction fragment was isolated from the gel as described above; about 0.5 μg of the desired fragment was obtained and suspended in 20 μl of dH$_2$O.

The second fragment needed to construct plasmid pBW28 is synthesized one strand at a time on an automated DNA synthesizer in substantial accordance with the procedure of Example 1. The two complementary strands, which will hybridize to form a double-stranded DNA segment with XbaI and NdeI overlaps, are kinased and annealed in substantial accordance with the procedure of Example 7A. The linker has the following structure:

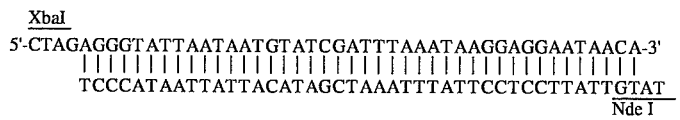

The third fragment needed to construct plasmid pBW28 was prepared by adding about 20 μg of plasmid pTPA103 in 20 μl of TE buffer to 10 μl of 10× BamHI buffer and 60 μl of dH$_2$O. Ten μl (about 50 units) of restriction enzyme BamHI were added to the solution of plasmid pTPA103 DNA, and the resulting reaction was incubated at 37° C. for 2 hours. The BamHI-digested plasmid pTPA103 DNA was precipitated with ethanol, collected by centrifugation, and resuspended in 10 μl of 10× EcoRI buffer and 80 μl of dH$_2$O. Ten μl (about 50 units) of restriction enzyme EcoRI were added to the solution of BamHI-digested plasmid pTPA103 DNA, and the resulting reaction was incubated at 37° C. for 2 hours. The Bam HI-EcoRI-digested plasmid pTPA103 DNA was loaded onto a 1.5% agarose gel and electrophoresed until the ~689 bp EcoRI-BmaHI restriction fragment, which comprises the coding sequence for the carboxyterminus of TPA, was separated from the other digestion products. About 0.5 μg of the ~689 bp fragment was isolated from the gel as described above, and then resuspended in 10 μl of dH$_2$O.

The final fragment necessary to construct plasmid pBW28 was isolated from plasmid pL110, which is a plasmid disclosed and claimed in U.S. patent application Ser. No. 769,221, filed Aug. 26, 1985, attorney docket number X-6638. A restriction site and function map of plasmid pL110 is presented in FIG. 12 of the accompanying drawings, and the construction of plasmid pL110 is disclosed below in part D of this Example.

About 25 μg of plasmid pL110 in 25 μl of TE buffer were added to 10 μl of 10× XbaI buffer (0.5M NaCl; 60 mM Tris-HCl, pH=7.9; 60 mM MgCl$_2$; and 1 mg/ml BSA) and 55 μl of dH$_2$O. Ten μl (about 50 units) of restriction enzyme XbaI were added to the solution of plasmid pL110 DNA, and the resulting reaction was incubated at 37° C. for 2 hours. The XbaI-digested plasmid pL110 DNA was precipitated with ethanol, collected by centrifugation, and resuspended in 10 μl of 10× BamHI buffer and 89 μl of dH$_2$O. One μl (about 5 units) of restriction enzyme BamHI was added to the solution of XbaI-digested plasmid pL110 DNA, and the resulting reaction was incubated at 37° C. for 30 minutes to obtain a partial BamHI digest. The XbaI-BamHI (partial) digest of plasmid pL110 DNA was loaded onto a 1% agarose gel and electrophoresed until the ~6.0 kb XbaI-BamHI fragment was clearly separated from the other digestion products. The ~6.0 kb restriction fragment was isolated from the gel as described above; about 0.5 μg of the ~6.0 kb XbaI-BamHI restriction fragment was obtained and suspended in about 40 μl of dH$_2$O. This ~6.0 kb XbaI-BamHI restriction fragment comprises all of plasmid pL110 except the EK-BGH-encoding DNA.

To construct plasmid pBW28, the following fragments are mixed together: (1) about 0.1 μg (8 μl) of the ~6.0 kb BamHI-XbaI restriction fragment of plasmid pL110; (2) about 0.05 μg (2 μl) of the ~560 bp NdeI-EcoRI restriction fragment of MP8BW27; (3) about 0.1 μg (2 μl) of the ~689 bp EcoRI-BamHI restriction fragment of plasmid pTPA103; and (4) about 0.02 μg (1 μl) of the ~45 bp XbaI-NdeI synthetic linker. Two μl of 10× T4 DNA ligase buffer and 1 μl (about 1 Weiss unit) of T4 DNA ligase are added to the mixture of DNA, and the resulting ligation reaction is incubated at 4° C. overnight. The ligated DNA constituted the desired plasmid pBW28. A restriction site and function map of plasmid pBW28 is presented in FIG. 12 of the accompanying drawings.

The ligated DNA was used to transform *E. coli* K12 MM294 (NRRL B-15625) made competent in substantial accordance with the procedure of Example 3, except that 50 mM CaCl$_2$ was used in the procedure. Due to the presence of the lambda pL promoter and the gene encoding the temperature-sensitive lambda pL repressor on plasmid pBW28, the transformation procedure and culturing of transformants were varied somewhat. The cells were not exposed to temperatures greater than 32° C. during transformation and subsequent culturing. Part D of this Example relates more fully the procedures for handling plasmids that encode the lambda pL promoter and its temperature-sensitive repressor. The desired *E. coli* K12 MM294/pBW28 transformants were identified by their tetracycline-resistant, ampicillin-sensitive phenotype and by restriction enzyme analysis of their plasmid DNA.

D. Construction of Plasmid pL110

Plasmid pL110 was constructed using plasmid pKC283 as starting material. *E. coli* K12 BE1201/pKC283 in lyophilized form is obtained from the NRRL under the accession number NRRL B-15830. The lyophilized samples are decanted into tubes containing 10 ml of L broth and incubated two hours at 32° C. at which time the cultures are made 50 μg/ml in ampicillin and then incubated at 32° C. overnight. The *E. coli* K12 BE1201/pKC283 cells were cultured at 32° C., because plasmid pKC283 comprises the pL promoter and because *E. coli* K12 BE1201 cells comprise a temperature-sensitive cI repressor gene integrated into the cellular DNA. When cells that comprise a wild-type lambda pL repressor gene or when cells that do not comprise a lambda pL promoter are utilized in this plasmid isolation procedure, as described in subsequent Examples herein, the temperature of incubation is 37° C.

A small portion of the overnight culture is placed on L-agar plates containing 50 μg/ml ampicillin in a manner so as to obtain a single colony isolate of *E. coli* K12 BE1201/pKC283. The single colony obtained was inoculated into 10 ml of L broth containing 50 μg/ml ampicillin and incubated overnight at 32° C. with vigorous shaking. The 10 ml overnight culture was inoculated into 500 ml of L broth and incubated at 32° C. with vigorous shaking until the culture reached stationary phase. Plasmid pKC283 DNA was then prepared from the cells in substantial accordance with the procedure of Example 3. About 1 mg of plasmid pKC283 was obtained and stored at 4° C. in TE buffer at a concentration of about 1 μg/μl. A restriction site and function map of plasmid pKC283 is presented in FIG. 12 of the accompanying drawings.

Ten μl (about 10 μg) of the plasmid pKC283 DNA were mixed with 20 μl of 10× medium-salt restriction buffer (500 mM NaCl; 100 mM Tris-HCl, pH=7.5; 100 mM MgCl$_2$; and 10 mM DTT), 20 μl of 1 mg/ml BSA, 5 μl of restriction enzyme pvuII (about 25 units), and 145 μl of dH$_2$O, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers (5'-CCTC-GAGG-3') were kinased in a mixture containing 10 μl of 5× Kinase Buffer (300 mM Tris-HCl, pH=7.8; 50 mM MgCl$_2$; and 25 mM DTT), 5 μl of 5 mM ATP, 24 μl of dH$_2$O, 0.5 μl of T4 polynucleotide kinase (about 2.5 units as defined by P-L Biochemicals), 5 μl of 1 mg/ml BSA, and 5 μl of 10 mM spermidine by incubating the mixture at 37° C. for 30 minutes. About 12.5 μl of the kinased XhoI linkers were added to the 5 μl of PvuII-digested plasmid pKC283 DNA, and then, 2.5 μl of 10× ligase buffer, 2.5 μl (about 2.5 units as defined by P-L Biochemicals) of T4 DNA ligase, 2.5 μl of 10 mM spermidine, and 12.5 μl of dH$_2$O were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10 mM MgCl$_2$; and 1 mM DTT). About 10 μl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 12 of the accompanying drawings.

*E. coli* K12MO (λ$^+$), available from the NRRL under the accession number NRRL B-15993, comprises the wild-type lambda pL cI repressor gene, so that transcription from the lambda pL promoter does not occur in *E. coli* K12MO(λ$^+$) cells. Single colonies of *E. coli* K12MO(λ$^+$) are isolated, and a 10 ml overnight culture of the cells is prepared; no ampicillin is used in the growth media. Fifty μl of the overnight culture were used to inoculate 5 ml of L broth, which also contained 10 mM MgSO$_4$ and 10 mM MgCl$_2$. The culture was incubated at 37° C. overnight with vigorous shaking. The following morning, the culture was diluted to 200 ml with L broth containing 10 mM MgSO$_4$ and 10 mM MgCl$_2$. The diluted culture was incubated at 37° C. with vigorous shaking until the O.D.$_{590}$ was about 0.5, which indicated a cell density of about 1×10$^8$ cells/ml. The culture was cooled for ten minutes in an ice-water bath, and the cells were then collected by centrifugation at 4000× g for 10 minutes at 4° C. The cell pellet was resuspended in 100 ml of cold 10 mM NaCl and then immediately repelleted by centrifugation. The cell pellet was resuspended in 100 ml of 30 mM CaCl₂ and incubated on ice for 20 minutes.

The cells were again collected by centrifugation and resuspended in 10 ml of 30 mM CaCl₂. A 0.5 ml aliquot of the cells was added to the ligated DNA prepared above; the DNA had been made 30 mM in CaCl₂. The cell·DNA mixture was incubated on ice for one hour, heat-shocked at 42° C. for 90 seconds, and then chilled on ice for about two minutes. The cell-DNA mixture was diluted into 10 ml of L broth in 125 ml flasks and incubated at 37° C. for one hour. Aliquots of 100 µl were plated on L·agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in substantial accordance with the procedure of Example 3, but the CsCl gradient step was omitted until the desired *E. coli* K12MO(l+)/pKC283PX transformants were identified. A restriction site and function map of plasmid pKC283PX is presented in FIG. 12 of the accompanying drawings.

Ten µg of plasmid pKC283PX DNA were dissolved in 20 µl of 10× high-salt buffer, 20 µl of 1 mg/ml BSA, 5 µl (about 50 units) of restriction enzyme BglII, 5 µl (about 50 units) of restriction enzyme XhoI, and 150 µl of dH₂O, and the resulting reaction was incubated at 37° C. for two hours. The reaction was stopped; the BglII-XhoI digested DNA was precipitated, and the DNA was resuspended in 5 µl of TE buffer.

A DNA linker with single-stranded DNA ends characteristic of BglII and XhoI restriction enzyme cleavage was synthesized using an automated DNA synthesizer as described in Example 1 and kinased as described in Example 7A. The DNA linker had the following structure:

The linker and BglII-XhoI-digested plasmid pKC283PX were ligated in substantial accordance with the ligation procedure described above. The ligated DNA constituted the desired plasmid pKC283-L. A restriction site and function map of plasmid pKC283-L is presented in FIG. 12 of the accompanying drawings. The plasmid pKC283-L DNA was used to transform *E. coli* K12MO(λ⁺), and the resulting *E. coli* K12MO(λ⁺)/pKC283-L transformants were identified by their ampicillin-resistant phenotype and by restriction enzyme analysis of their plasmid DNA.

About 10 µg of plasmid pKC283-L DNA were dissolved in 20 µl 10× high-salt buffer, 20 µl of 1 mg/ml BSA, 5 µl (about 50 units) of restriction enzyme XhoI, and 155 µl of dH₂O, and the resulting reaction was incubated at 37° C. for two hours. The XhoI-digested plasmid pKC283-L DNA was then precipitated and resuspended in 2 µl of 10× nick-translation buffer (0.5M Tris-HCl, pH= 7.2; 0.1M MgSO₄; and 1 mM DTT), 1 µl of a solution 2 mM in each of the deoxynucleotide triphosphates, 15 µl of dH₂O, 1 µl (about 6 units as defined by P-L Biochemicals) of Klenow enzyme, and 1 µl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the linker ligation procedures described above. After the ligation reaction, the DNA was digested with about 100 units of BamHI for about 2 hours at 37° C. in high-salt buffer. After the BamHI digestion, the DNA was prepared for ligation, and the ~5.9 kb BamHI restriction fragment was circularized by ligation and transformed into *E. coli* K12MO(λ⁺) in substantial accordance with the procedures described above. The *E. coli* K12MO(λ+)/pKC283-LB transformants were identified, and then, plasmid pKC283-LB DNA was prepared from the transformants in substantial accordance with the procedure of Example 3. A restriction site and function map of plasmid pKC283-LB is presented in FIG. 12 of the accompanying drawings.

About 10 µg of plasmid pKC283PX were digested with restriction enzyme SalI in high-salt buffer, treated with Klenow enzyme, and ligated to EcoRI linkers (5'-GAG-GAATTCCTC-3') in substantial accordance with the procedures described above. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform *E. coli* K12MO(λ⁺), and after the *E. coli* K12 MO(λ⁺)/pKC283PRS transformants were identified, plasmid pKC283PRS DNA was prepared from the transformants in substantial accordance with the procedure of Example 3. A restriction site and function map of plasmid pKC283PRS is presented in FIG. 12 of the accompanying drawings.

About 10 µg of plasmid pKC283PRS were digested in 200 µl of high-salt buffer with about 50 units each of restriction enzymes PstI and SphI. After incubating the reaction at 37° C. for about 2 hours, the reaction mixture was electrophoresed on a 0.6% low-melting-temperature agarose (FMC Corporation, Marine Colloids Division, Rockland, Maine 04841) gel.

The gel was stained in a dilute solution of ethidium bromide, and the band of DNA constituting the ~0.85 kb PstI-SphI restriction fragment, which was visualized with long-wave UV light, was cut from the gel in a small segment. The volume of the gel segment was determined by its weight and density, and an equal volume of 10 mM Tris-HCl, pH 7.6, was added to the tube containing the gel segment. The gel segment was then melted by incubation at 72° C. About 1 µg of the ~0.85 kb PstI-SphI restriction fragment of plasmid pKC283PRS was obtained in a volume of about 100 µl after 2 phenol extractions and ethanol precipitation. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB. The ligated DNA constituted the desired plasmid pL32. A restriction site and function map of plasmid pL32 is presented in FIG. 12 of the accompanying drawings. Plasmid pL32 was transformed into *E. coli* K12MO(λ⁺) cells; plasmid pL32 DNA was prepared from the *E. coli* K12MO(λ+)/pL32 transformants in substantial accordance with the procedure of Example 3. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together.

Plasmid pCC101 is disclosed in Example 3 of U.S. Pat. No. 4,745,069, issued May 17, 1988, incorporated herein by reference. A restriction site and function map of plasmid pCC101 is presented in FIG. 12 of the accompanying drawings. To isolate the EK-BGH-encoding DNA, about 10 μg of plasmid pCC101 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated from the gel and prepared for ligation.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid pCC101 to yield plasmid pL47. A restriction site and function map of plasmid pL47 is presented in FIG. 12 of the accompanying drawings. Plasmid pL47 was transformed into *E. coli* K12MO(λ⁺), and the *E. coli* K12MO(λ⁺)/pL47 transformants were identified. Plasmid pL47 DNA was prepared from the transformants in substantial accordance with the procedures of Example 3.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 12 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and then treated with Klenow enzyme in substantial accordance with the procedure described above. After the Klenow reaction, the EcoRI-digested, Klenow-treated plasmid pPR12 DNA was recircularized by ligation, and the ligated DNA, which constituted the desired plasmid pPR12ΔR1, was used to transform *E. coli* K12 RV308 in substantial accordance with the procedure of Example 3; transformants were selected based on tetracycline (10 μg/ml) resistance. After the *E. coli* K12 RV308/pPR12ΔR1 transformants were identified, plasmid pPR12ΔR1 DNA was prepared from the transformants in substantial accordance with the procedure of Example 3.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and then treated with Klenow enzyme. After the Klenow reaction, the AvaI-digested, Klenow-treated plasmid pPR12ΔR1 DNA was ligated to EcoRI linkers (5'-GAGGAATTCCTC-3'), precipitated, resuspended in about 200 μl of high-salt buffer containing about 50 units of restriction enzyme EcoRI, and incubated at 37° C. for about 2 hours. After the EcoRI digestion, the reaction mixture was loaded onto a 0.6% low-melting agarose gel, and the ~5.1 kb EcoRI restriction fragment was purified from the gel and recircularized by ligation to yield the desired plasmid pPR12AR1, all in substantial accordance with the procedures described above. The plasmid pPR12AR1 DNA was transformed into *E. coli* K12 RV308 in substantial accordance with the procedure of Example 3; selection of transformants was based on tetracycline resistance. Plasmid pPR12AR1 DNA was prepared from the transformants in substantial accordance with the procedure of Example 3. A restriction site and function map of plasmid pPR12AR1 is presented in FIG. 12 of the accompanying drawings.

About 10 μg of plasmid pPR12AR1 DNA were suspended in about 200 μl of high-salt buffer containing about 50 units each of restriction enzymes PstI and EcoRI, and the digestion reaction was incubated at 37° C. for about 2 hours. The reaction mixture was then loaded onto a 1% agarose gel, and the ~2.9 kb PstI-EcoRI restriction fragment of plasmid pPR12AR1 was isolated and prepared for ligation in substantial accordance with the procedure of Example 3.

About 10 μg of plasmid pL47 were digested with restriction enzymes PstI and BamHI in 200 μl of high-salt buffer at 37° C. for two hours. The PstI-BamHI-digested DNA was loaded onto a 1% agarose gel, and the ~2.7 kb PstI-BamHI restriction fragment that comprised the origin of replication and a portion of the ampicillin resistance-conferring gene was isolated and prepared for ligation in substantial accordance with the procedure of Example 3. In a separate reaction, about 10 μg of plasmid pL47 DNA were digested with restriction enzymes EcoRI and BamHI in 200 μl of high-salt buffer at 37° C. for two hours, and the ~1.003 kb EcoRI-BamHI restriction fragment that comprised the lambda pL transcription activating sequence, the *E. coli* lpp translation activating sequence, and the EK-BGH-encoding DNA was isolated and prepared for ligation.

The ~2.7 kb PstI-BamHI and ~1.003 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308. Tetracycline resistance was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 12 of the accompanying drawings.

E. Final Construction of Plasmid pBW32

Approximately 10 μg of plasmid pSV2-β-globin DNA (NRRL B-15928) were dissolved in 10 μl of 10× HindIII reaction buffer, 5 μl (about 50 units) of restriction enzyme HindIII, and 85 μl of dH₂O, and the reaction was placed at 37° C. for 2 hours. The reaction mixture was then made 0.15M in LiCl, and after the addition of 2.5 volumes of ethanol and incubation in a dry-ice-ethanol bath, the DNA was pelleted by centrifugation.

The DNA pellet was dissolved in 10 μl of 10× BglII buffer, 5 μl (~50 units) of restriction enzyme BglII, and 85 μl of dH₂O, and the reaction was placed at 37° C. for two hours. After the BglII digestion, the reaction mixture was loaded onto a 0.85% agarose gel, and the fragments were separated by electrophoresis. The gel was visualized using ethidium bromide and ultraviolet light, and the band containing the desired ~4.2 kb HindIII-BglII fragment was excised from the gel as previously described and purified in substantial accordance with the procedure of Example 4A. The pellet was resuspended in 10 μl of dH₂O and constituted ~5 μg of the desired ~4.2 kb HindIII-BglII restriction fragment of plasmid pSV2-β-globin. The ~2.0 kb HindIII-BamHI restriction fragment of plasmid pTPA103 that encodes TPA was isolated from plasmid pTPA103 in substantial accordance with the foregoing teaching.

About 5 μg of the ~2.0 kb HindIII-BamHI restriction fragment of plasmid pTPA103 were obtained, suspended in 10 μl of dH₂O, and stored at −20° C.

Two μl of the ~4.2 kb BglII-HindIII restriction fragment of plasmid pSV2-β-globin and 4 μl of the ~2.0 kb HindIII-BamHI fragment of plasmid pTPA103 were mixed together and then incubated with 2 µl of 10× ligase buffer, 11 µl of dH₂O, and 1 µl of T4 DNA ligase (about 500 units) at 4° C. overnight. The ligated DNA constituted the desired plasmid pTPA301; a restriction site and function map of the plasmid is presented in FIG. 12 of the accompanying drawings. The ligated DNA was used to transform *E. coli* K12 RR1 cells (NRRL B15210) made competent for transformation in substantial accordance with the procedure of Example 3. Plasmid DNA was obtained from the *E. coli* K12 RR1/pTPA301 transformants in substantial accordance with the procedure of Example 3.

Plasmid pSV2-dhfr comprises a dihydrofolate reductase (dhfr) gene useful for selection of transformed eukaryotic cells and amplification of DNA covalently linked to the dhfr gene. Ten µg of plasmid pSV2-dhfr (isolated from *E. coli* K12 HB101/pSV2-dhfr, ATCC 37146) were mixed with 10 µl of 10× PvuII buffer, 2 µl (about 20 units) of PvuII restriction enzyme, and 88 µl of dH₂O, and the resulting reaction was incubated at 37° C. for two hours. The reaction was terminated by phenol and chloroform extractions, and then, the PvuII-digested plasmid pSV2-dhfr DNA was precipitated and collected by centrifugation.

BamHI linkers (5'-CGGATCCCG-3') were kinased and prepared for ligation by the following procedure. To 1 µg of linker in 5 µl of dH₂O was added: 10 µl of 5× kinase buffer, 5 µl of 5 mM ATP, 5 µl of 5 mMATP, 5 µl of BSA (1 mg/ml), 5 µl of 10 mM spermidine, 19 µl of dH₂O, and 1 µl of T4 polynucleotide kinase (about 10 units). This reaction was then incubated at 37° C. for 60 minutes and stored at –20° C. Five µl (about 5 µg) of the PvuII-digested plasmid pSV2-dhfr and 12 µl (about 0.25 µg) of the kinased BamHI linkers were mixed and incubated with 11 µl of dH₂O, 2 µl 10× ligase buffer, and 1 µl (about 1000 units) of T4 DNA ligase at 16° C. overnight.

Ten µl of 10× BamHI reaction buffer, 10 µl (about 50 units) of BamHI restriction enzyme, and 48 µl of dH₂O were added to the ligation reaction mixture, which was then incubated at 37° C. for 3 hours. The reaction was loaded onto a 1% agarose gel, and the desired ~1.09 kb fragment, which comprises the dhfr gene, was isolated from the gel in substantial accordance with the procedure of Example 4A. All linker additions performed in these examples were routinely purified on an agarose gel to reduce the likelihood of multiple linker sequences in the final vector. Approximately 3 µg of fragment were obtained and suspended in 10 µl of TE buffer.

Next, approximately 15 µl (about 1 µg) of plasmid pTPA301 were digested with BamHI restriction enzyme as taught above. Because there is a unique BamHI site in plasmid pTPA301, this BamHI digestion generates linear plasmid pTPA301 DNA. The BamHI-digested plasmid pTPA301 was precipitated with ethanol and resuspended in 94 µl of dH₂O and phosphatased using 1 µl of calf-intestinal alkaline phosphatase, and 5 µl of 1M Tris-HCl, pH= 9.0, at 65° C. for 45 min. The DNA was extracted with phenol:chloroform, the next racted with chloroform:isoamyl alcohol, ethanol precipitated, and resuspended in 20 µl dH₂O. Ten µl (about 0.25 µg) of phosphatased plasmid pTPA301 were added to 5 µl of the ~1.09 kb BamHI dhfr-gene-containing restriction fragment (about 1.5 µg), 3 µl of 10× ligase buffer, 3 µl (about 1500 units) of T4 DNA ligase, and 9 µl dH₂O. This ligation reaction was incubated at 15° C. overnight; the ligated DNA constituted the desired plasmid pTPA303 DNA.

Plasmid pTPA303 was used to transform *E. coli* K12 RR1 (NRRL B-15210), and the resulting *E. coli* K12 RR1/pTPA303 transformants were identified by their ampicillin-resistant phenotype and by restriction enzyme analysis of their plasmid DNA. Plasmid pTPA303 was isolated from the transformants in substantial accordance with the procedure of Example 3.

To isolate the ~2.7 kb EcoRI-BglII restriction fragment that encodes the pBR322 replicon and β-lactamase gene from plasmid pTPA301, about 10 µg of plasmid pTPA301 are digested to completion in 400 µl total reaction volume with 20 units BglII restriction enzyme in 1× BglII buffer at 37° C. After the BglII digestion, the Tris-HCl concentration is adjusted to 110 mM, and 20 units of EcoRI restriction enzyme are added to the BglII-digested DNA at 37° C. After the gCqRI digestion, the EcoRI-BglII-digested DNA is loaded onto a 1% agarose gel and electrophoresed until the ~2.7 kb EcoRI-BglII restriction fragment is separated from the other digestion products, and then, the ~2.7 kb fragment is isolated and prepared for ligation.

To isolate a restriction fragment that comprises the dhfr gene, plasmid pTPA303 was double-digested with HindIII and EcoRI restriction enzymes, and the ~2340 bp EcoRI-HindIII restriction fragment that comprises the dhfr gene was isolated and recovered.

To isolate the ~2.0 kb HindIII-SstI restriction fragment of plasmid pTPA303 that comprises the coding region for the carboxy-terminus of TPA and the SV40 promoter, plasmid pTPA303 was double digested with HindIII and SstI restriction enzymes in 1× HindIII buffer. The ~1.07 kb fragment was isolated from the gel and prepared for ligation.

To isolate the ~680 bp XhoII (compatible for ligation with the BglII overlap)-SstI restriction fragment of plasmid pBW28 that comprises the coding region for the amino terminus of modified TPA, about 10 µg of plasmid pBW28 were digested with XhoII enzyme to completion in 1× XhoII buffer (0.1M Tris-HCl, pH= 8.0; 0.1M MgCl₂; 0.1% Triton X-100; and 1 mg/ml BSA). The XhoII-digested DNA was recovered by ethanol precipitation and subsequently digested to completion with SstI enzyme. The XhoII-SstI-digested DNA was loaded onto an acrylamide gel, and the desired fragment was isolated from the gel and prepared for ligation in substantial accordance with the procedure of Example 4A.

About 0.1Hg of each of the above fragments: (1) the ~2.7 kb EcoRI-BglII restriction fragment of plasmid pTPA301; (2) the ~2.34 kb EcoRI-HindIII restriction fragment of plasmid pTPA303; (3) the ~1.07 kb SstI-HindIII restriction fragment of plasmid pTPA303; and (4) the ~0.68 kb SstI-XhoII restriction fragment of plasmid pBW28 were ligated together to form plasmid pBW32. The ligation mix was used to transform *E. coli* K12MM294 as taught in Example 3, except that 50 mM CaCl₂ was used in the procedure. Transformants were identified by their ampicillin-resistant phenotype and by restriction analysis of their plasmid DNA. Plasmid pBW32 DNA was obtained from the *E. coli* K12MM294/pBW32 transformants in substantial accordance with the procedure of Example 3. A restriction site and function map of plasmid pBW32 is presented in FIG. 12 of the accompanying drawings.

EXAMPLE 12

Construction of Plasmids pLPChd1, pLPChd2, DLPChd1(GT), pLPChd2(GT), pLPCdhfr1, pLPCdhfr2, pLPCdhfr1(GT) and pLPCdhfr2(GT)

A. Construction of Plasmids pLPChd1 and pLPChd2

About 20 µg of plasmid pBW32 (Example 11) in 20 µl of TE buffer were added to 10 µl of 10× BamHI buffer and 60 µl of dH₂O. Ten µl (about 50 units) of restriction enzyme BamHI were added to the solution of plasmid pBW32 DNA, and the resulting reaction was incubated at 37° C. for two hours. The BamHI-digested plasmid pBW32 DNA was precipitated with ethanol, collected by centrifugation, and resuspended in 5 µl of 10× Klenow buffer, 45 µl of dH$_2$O, and 2 µl (about 100 units) of Klenow enzyme. The reaction was incubated at 16° C. for 30 minutes; then, the reaction mixture was loaded onto a 1% agarose gel and electrophoresed until the digestion products were clearly separated. The ~1.09 kb Klenow-treated, BamHI restriction fragment of plasmid pBW32 that comprises the dhfr gene was isolated from the gel and prepared for ligation in substantial accordance with the procedure of Example 4A. About 4 µg of the desired fragment were obtained and suspended in 5 µl of TE buffer.

About 200 µg of plasmid pLPChyg1 (Example 10) in 100 µl of TE buffer were added to 15 µl of 10× EcoRI buffer and 30 µl of dH$_2$O. About 5 µl (about 50 units) of restriction enzyme EcoRI were added to the solution of plasmid pLPChyg1 DNA, and the resulting reaction was incubated at 37° C. for about 10 minutes. The short reaction time was calculated to produce a partial EcoRI digestion. Plasmid pLPChyg1 has two EcoRI restriction sites, one of which is within the coding sequence of the hygromycin resistance-conferring (HmR) gene, and it was desired to insert the ~1.09 kb dhfr-gene-containing restriction fragment from plasmid pBW32 into the EcoRI site of plasmid pLPChyg1 that is not in the HmR gene. The EcoRI (partial) digest of plasmid pLPChyg1 DNA was loaded onto an agarose gel and electrophoresed until the singly-cut plasmid pLPChyg1 DNA was separated from uncut plasmid DNA and the other digestion products. The singly-cut DNA was isolated from the gel and prepared for ligation in substantial accordance with the procedure of Example 4A. About 2 µg of the singly-EcoRI-cut plasmid pLPChyg1 were obtained and suspended in 25 µl of TE buffer. To this sample, 5 µl (about 25 units) of Klenow enzyme, 5 µl of 10× Klenow buffer, and 40 µl of dH$_2$O were added, and the resulting reaction was incubated at 16° C. for 60 minutes. The Klenow-treated, EcoRI (partial) digest of plasmid pLPChyg1 DNA was then extracted twice with phenol and then once with chloroform, precipitated with ethanol, and resuspended in 25 µl of TE buffer.

About 5 µl of the ~1.09 kb Klenow-treated BamHI restriction fragment of plasmid pBW32 and about 5 µl of the singly-EcoRI-cut plasmid pLPChyg1 DNA were mixed together, and 1 µl of 10× ligase buffer, 5 µl of dH$_2$O, 1 µl (about 500 units) of T4 DNA ligase, and 1 µl (about 2 units) of T4 RNA ligase were added to the mixture of DNA, and the resulting reaction was incubated at 16° C. overnight. The ligated DNA constituted the desired plasmids pLPChd1 and pLPChd2, which differ only with respect to the orientation of the ~1.09 kb fragment that comprises the dhfr gene.

The ligated DNA was used to transform *E. coli* K12 HB101 cells made competent for transformation in substantial accordance with the procedure of Example 3. The transformed cells were plated onto L-agar containing 100 µg/ml ampicillin, and the ampicillin-resistant transformants were analyzed by restriction enzyme analysis of their plasmid DNA to identify the *E. coli* K12 HB101/pLPChd1 and *E. coli* K12 HB101/pLPChd2 transformants. Plasmid pLPChd1 and plasmid pLPchd2 DNA were isolated from the appropriate transformants in substantial accordance with the procedure of Example 3.

Plasmids pLPChd3 and pLPChd4 are similar in structure to plasmids pLPChd1 and pLPChd2. Plasmids pLPChd3 and pLPChd4 are constructed in substantial accordance with the procedure used to construct plasmids pLPChd1 and pLPChd2, except plasmid pLPChyg2 is used as starting material in the procedure rather than plasmid pLPChyg1.

B. Construction of Plasmids pLPChd1(GT), DLPChd2(GT), pLPChd3(GT), and pLPChd4(GT)

A poly-GT element is inserted into the unique XhoI site, between the BK enhancer and the Ad2 late promoter, in plasmid pLPChd1, pLPChd2, pLPChd3 or pLPChd4 in substantial accordance with the procedure of Example 4B.1. The XhoI-digested poly-GT element and XhoI-digested plasmid pLPChd1, pLPChd2, pLPChd3 or pLPChd4 DNA are ligated and the ligated DNA constitutes the desired plasmids pLPChd1(GT), pLPChd2(GT), pLPChd3(GT) and pLPChd4(GT), respectively. A restriction site and function map of plasmid pLPChd1(GT) is presented in FIG. 13 of the accompanying drawings.

C. Construction of Plasmids pLPCdhfr1 and DLPCdhfr2

About 100 µl of plasmid pBW32 in 100 µl of TE buffer were added to 15 µl of 10× BamHI buffer and 25 µl of dH$_2$O. Ten µl (about 25 units) of restriction enzyme BamHI were added to the solution of plasmid pBW32 DNA, and the resulting reaction was incubated at 37° C. for 2 hours. The BamHI-digested plasmid pBW32 DNA was treated with Klenow enzyme in substantial accordance with the procedure in Example 10A. The blunt-ended fragment was precipitated with ethanol, resuspended in 10 µl of TE buffer, loaded onto a 1% agarose gel, and electrophoresed until the ~1.09 kb BamHI restriction fragment that comprises the dhfr gene was separated from the other digestion products. The ~1.09 kb restriction fragment was then isolated from the gel and prepared for ligation in substantial accordance with the procedure of Example 4A; about 10 µg of the desired fragment were obtained and suspended in 50 µl of TE buffer.

About 5 µl of Nde-StuI-digested plasmid pLPC DNA, as prepared in Example 10, were added to 5 µl of the Klenow-treated, ~1.09 kb BamHI restriction fragment of plasmid pBW32, 1.5 µl of 10× ligase buffer, 1 µl (about 1000 units) of T4 DNA ligase, 1 µl (about 2 units) of T4 RNA ligase, and 1.5 µl of dH$_2$O. The resulting ligation reaction was incubated at 16° C. overnight; the ligated DNA constituted the desired plasmids pLPCdhfr1 and pLPCdhfr2, which differ only with respect to the orientation of the ~1.09 kb fragment that contains the dhfr gene. The ligated DNA was used to transform *E. coli* K12 HB101 in substantial accordance with the procedure of Example 3. The transformed cells were plated onto L-agar containing ampicillin, and the ampicillin-resistant *E. coli* K12 HB101/pLPCdhfr1 and *E. coli* K12 HB101/pLPCdhfr2 transformants were identified by restriction enzyme analysis of their plasmid DNA.

D. Construction of Plasmids pLPCdhfr1(GT) and pLPCdhfr2(GT)

A poly-GT element is inserted into the unique XhoI site in pLPCdhfr1 or pLPCdhfr2, between the BK enhancer and the Ad2 late promoter, in substantial accordance with the procedure of Example 4B.1. The XhoI-digested poly-GT element and XhoI-digested plasmid pLPCdhfr1 or pLPCdhfr2 DNA are ligated and the ligated DNA constitutes the desired plasmids pLPCdhfr1(GT) and pLPCdhfr2(GT), respectively.

EXAMPLE 13

Construction of Plasmids phd and phd(GT)

A. Construction of Plasmid phd

To construct plasmid phd, it was necessary to prepare the plasmid pLPChd1 DNA (Example 12), used as starting material in the construction of plasmid phd, from *E. coli* host cells that lack an adenine methylase, such as that encoded by the dam gene, the product of which methylates the adenine residue in the sequence 5'-GATC-3'. *E. coli* K12 GM48 (NRRL B-15725) lacks a functional dam methylase and so is a suitable host to use for the purpose of preparing plasmid pLPChd1 DNA for use as starting material in the construction of plasmid phd.

*E. coli* K12 GM48 cells were cultured and made competent for transformation, and plasmid pLPChd1 was used to transform the *E. coli* K12 GM48 cells in substantial accordance with the procedure of Example 3. The transformed cells were plated on L-agar containing ampicillin, and once the ampicillin-resistant, *E. coli* K12 GM48/pLPChd1 transformants had formed colonies, one such colony was used to prepare plasmid pLPChd1 DNA in substantial accordance with the procedure of Example 3. About 1 mg of plasmid pLPChd1 DNA was obtained and suspended in about 1 ml of TE buffer.

About 2 µg of plasmid pLPChd1 DNA in 2 µl of TE buffer were added to 2 µl of 10× BclI buffer (750 mM KCl; 60 mM Tris-HCl, pH=7.4; 100 mM $MgCl_2$; 10 mM DTT and 1 mg/ml BSA) and 14 µl of $dH_2O$. Two µl (about 10 units) of restriction enzyme BclI were added to the solution of plasmid pLPChd1 DNA, and the resulting reaction was incubated at 50° C. for two hours. The reaction was stopped by extracting the mixture once with phenol and twice with chloroform.

About 1 µl of the BclI-digested plasmid pLPChd1 DNA was added to 1 µl of 10× T4 DNA ligase buffer, 8 µl of $dH_2O$ and 1 µl (about 500 units) of T4 DNA ligase. The ligation reaction was incubated at 16° C. overnight, and the ligated DNA constituted the desired plasmid phd. Plasmid phd results from the deletion of the extra BclI linkers that attached during the construction of plasmid pLPcat and the two adjacent BclI restriction fragments of a total size of about 1.45 kb from plasmid pLPChd1. Plasmid phd facilitates the expression of any DNA sequence from the BK virus enhancer-adenovirus late promoter as described herein, because the DNA to be expressed can be readily inserted in the correct position for expression at the single BclI site on plasmid phd.

The ligated DNA was used to transform *E. coli* K12 GM48 in substantial accordance with the procedure of Example 3. The transformed cells were plated on L-agar containing ampicillin, and the ampicillin-resistant *E. coli* K12 GM48/phd transformants were identified by restriction enzyme analysis of their plasmid DNA.

Plasmids analogous to plasmid phd can be constructed in substantial accordance with the foregoing procedure for constructing plasmid phd using any of plasmids pLPChd2, pLPChd3, or pLPChd4 as starting material rather than plasmid pLPChd1. These analogous plasmids differ from plasmid phd only with respect to the orientation of the hygromycin resistance-conferring and/or dhfr genes.

B. Construction of Plasmid phd(GT) 1. Construction using Plasmid phd

A poly-GT element is inserted into the unique XhoI site in phd, between the BK enhancer and the Ad2 late promoter, in substantial accordance with the procedure of Example 4B.1. The XhoI-digested poly-GT element and XhoI-digested plasmid phd DNA are ligated and the ligated DNA constitutes the desired plasmid phd(GT). A restriction site and function map of plasmid phd(GT) is presented in FIG. 14 of the accompanying drawings. Plasmid phd(GT) facilitates the expression of any DNA sequence from the poly-GT-BK virus enhancer-adenovirus late promoter of the present invention, because the DNA to be expressed can be readily inserted in the correct position for expression at the single BclI site on plasmid phd(GT). In the presence of an immediate-early gene product of a large DNA virus, such as the E1A gene product, the plasmid phd(GT) provides an improved expression vector for any inserted DNA sequence.

The ligated DNA is used to transform *E. coli* K12 GM48 and *E. coli* K12 GM48/phd(GT) transformants are selected, all in substantial accordance with the procedures of part A above. 2. Construction Using Plasmid pLPChd1(GT), pLPChd2(GT), pLPChdB(GT) or pLPChd4(GT)

Alternatively, plasmid phd(GT) is prepared in substantial accordance with the procedure of part A of this Example, except that plasmid pLPChd1(GT), pLPChd2(GT), pLPChd3(GT) or pLPChd4(GT) (as described in Example 12B) is used as starting material, instead of plasmid pLPChd1, pLPChd2, pLPChd3 or pLPChd4.

EXAMPLE 14

Construction of Plasmids pLPCE1A and pLPCE1A(GT)

A. Construction of Plasmid pLPCE1A

To isolate the E1A gene of adenovirus 2 DNA, about 20 µg of adenovirus 2 DNA (from BRL) were dissolved in 10 µl of 10× BalI buffer (100 mM Tris-HCl, pH=7.6; 120 mMMgCl$_2$; 100 mM 2-mercaptoethanol; and 1 mg/ml BSA) and 80 µl of $dH_2O$. Ten µl (about 20 units) of restriction enzyme BalI were added to the solution of adenovirus 2 DNA, and the resulting reaction was incubated at 37° C. for two hours. The BalI-digested DNA was loaded onto a 1% agarose gel and electrophoresed until the ~1.8 kb restriction fragment that comprises the E1A gene was separated from the other digestion products. The ~1.08 kb fragment was isolated from the gel and prepared for ligation in substantial accordance with the procedure of Example 4A. About 3 µg of the desired fragment was obtained and suspended in 20 µl of TE buffer.

About 5 µg of plasmid pLPC DNA in 5 µl of TE buffer were added to 2 µl of 10× StuI buffer and 11 µl of $dH_2O$. Two µl (about 10 units) of restriction enzyme StuI were added to the solution of plasmid pLPC DNA, and the resulting reaction was incubated at 37° C. for 2 hours. The StuI-digested plasmid pLPC DNA was precipitated with ethanol and resuspended in 2 µl of 10× NdeI buffer and 16 µl of $dH_2O$. Two µl (about 10 units) of restriction enzyme NdeI were added to the solution of StuI-digested plasmid pLPC DNA, and the resulting reaction was incubated at 37° C. for 2 hours.

The NdeI-StuI-digested plasmid pLPC DNA was precipitated with ethanol and resuspended in 5 µl of 10× Klenow buffer and 42 µl of $H_2O$. Three µl (about 6 units) of Klenow enzyme were added to the solution of DNA, and the resulting reaction was incubated at 37° C. for 30 minutes. The reaction mixture was then loaded onto a 1% agarose gel and electrophoresed until the ~5.82 kb, Klenow-treated, NdeI-StuI restriction fragment was clearly separated from the other reaction products. The fragment was isolated from the gel and prepared for ligation in substantial accordance with the procedure of Example 4A. About 2 µg of the ~5.82 kb, Klenow-treated, NdeI-StuI restriction fragment of plasmid pLPC were obtained and suspended in 25 µl of TE buffer.

About 9 μl of the ~1.08 kb BalI restriction fragment of adenovirus 2 that encodes the E1A gene and 3 μl of the ~5.82 kb, Klenow-treated, NdeI-StuI restriction fragment of plasmid pLPC were added to 2 μl of 10× ligase buffer and 4 μl of dH$_2$O. One μl (about 500 units) of T4 DNA ligase and 1 μl (about 2 units) of T4 RNA ligase were added to the solution of DNA, and the resulting reaction was incubated at 16° C. overnight.

The ligated DNA constituted the desired plasmids pLPCE1A and pLPCE1A1, which differ with respect to the orientation of the E1A gene and possibly differ with respect to the expression-enhancing effect the BK enhancer has on the E1A gene on the plasmid. Because the E1A promoter is located closer to the BK enhancer on plasmid pLPCE1A than plasmid pLPCE1A1, E1A expression may be higher when plasmid pLPCE1A is used as opposed to plasmid pLPCE1A1.

The ligated DNA was used to transform *E. coli* K12 HB101 in substantial accordance with the procedure of Example 3. The transformed cells were plated on L-agar containing ampicillin, and the ampicillin-resistant transformants were screened by restriction enzyme analysis of their plasmid DNA to identify the *E. coli* K12 HB101/pLPCE1A and *E. coli* K12 HB101/pLPCE1A1 transformants. Plasmid DNA was obtained from the transformants for use in later experiments in substantial accordance with the procedure of Example 3.

B. Construction of Plasmids DLPCE1A(GT) and pLPCE1lA1(GT)

A poly-GT element is inserted into the unique XhoI site in plasmid pLPCE1A or pLPCE1A1, between the BK enhancer and the Ad2 late promoter, in substantial accordance with the procedure of Example 4B.1. The XhoI-digested poly-GT element and XhoI-digested plasmid pLPCE1A or pLPCE1A1 DNA are ligated, and the ligated DNA constitutes the desired plasmids pLPCE1A(GT) and pLPCE1AI(GT), respectively. A restriction site and function map of plasmid pLPCE1A(GT) is presented in FIG. 15 of the accompanying drawings.

EXAMPLE 15

ConstructioB of Plasmids pBLT and pBLT(GT)

A. Construction of Plasmid pBLT

About 1 μg of plasmid pBW32 DNA (FIG. 12, Example 11) in 1 μl of TE buffer was added to 2 μl of 10× BamHI buffer and 15 μl of dH$_2$O. About 2 μl (about 10 units) of restriction enzyme BamHI were added to the solution of plasmid pBW32 DNA, and the resulting reaction was incubated to 37° C. for 2 hours. The reaction was stopped by first extracting the reaction mixture with phenol and then extracting the reaction mixture twice with chloroform. About 1 μl of the BamHI-digested plasmid pBW32 DNA was added to 1 μl of 10× ligase buffer and 8 μl of dH$_2$O, and after 1 μl (about 500 units) of T4 DNA ligase was added to the solution of DNA, the resulting reaction was incubated at 16° C. overnight.

The ligated DNA constituted the desired plasmid pBW32del, which is about 5.6 kb in size and comprises a single HindIII restriction site. The ligated DNA was used to transform *E. coli* K12 HB101 in substantial accordance with the procedure of Example 3. The desired *E. coli* K12 HB101/pBW32del transformants were identified by their ampicillin-resistant phenotype and by restriction enzyme analysis of their plasmid DNA. Plasmid pBW32del DNA was obtained from the transformants for use in subsequent constructions in substantial accordance with the procedure of Example 3.

About 1 μg of plasmid pBW32del in 1 μl of TE buffer was added to 2 μl of 10× HinIII buffer and 15 μl of dH$_2$O. Two μl (about 10 units) of restriction enzyme HindIII were added to the solution of plasmid pBW32del DNA, and the resulting reaction was incubated at 37° C. for 2 hours. The sample was diluted to 100 μl with TE buffer and treated with calf-intestinal alkaline phosphatase in substantial accordance with the procedure described in Example 4B. The reaction was extracted twice with phenol then once with chloroform. The HindIII-digested plasmid pBW32del DNA was then precipitated with ethanol and resuspended in 10 μl of dH$_2$O.

Plasmid pBal8cat (Example 18) was digested with restriction enzyme HindIII, and the ~0.65kb HindIII restriction fragment that comprises the modified BK enhancer-adenovirus 2 late promoter cassette was isolated and prepared for ligation in substantial accordance with the procedure of Example 6A. About 0.1 μg of the ~0.65 kb HindIII restriction fragment of plasmid pBal8cat in 5 μl of TE buffer was added to 3 μl of the solution of HindIII-digested plasmid pBW32del. One μl (about 500 units) of T4 DNA ligase and 1 μl of 10× ligase buffer was added to the mixture of DNA, and the resulting reaction was incubated at 16° C. overnight.

The ligated DNA constituted the desired plasmid pBLT. The ligated DNA was used to transform *E. coli* K12 HB101 in substantial accordance with the procedure of Example 3. The transformed cells were plated on L-agar containing ampicillin, and the ampicillin-resistant *E. coli* K12 HB101/pBLT transformants were identified by restriction enzyme analysis of their plasmid DNA. Because the ~0.65 kb HindIII restriction fragment could insert into HindIII-digested plasmid pBW32del in either one of two orientations, only one of which yields plasmid pBLT, the orientation of the ~0.65 kb HindIII restriction fragment had to be determined to identify the *E. coli* K12 HB101/pBLT transformants. Plasmid pBLT DNA was prepared from the transformants for use in subsequent constructions in substantial accordance with the procedure of Example 3.

B. Construction of Plasmid pBLT(GT)

A poly-GT element is inserted into the unique BamHI site in plasmid pBLT, between the BK enhancer and the Ad2 late promoter, in substantial accordance with the procedure of Example 19. The poly-GT element and BamHI-digested plasmid pBLT DNA are ligated and the ligated DNA constitutes the desired plasmid pBLT(GT). A restriction site and function map of plasmid pBLT(GT) is presented in FIG. 16 of the accompanying drawings.

EXAMPLE 16

Construction of Plasmids pBLThyg1, pBLThyg2, pBLThyg1(GT), pBLThyg2(GT), pBLTdhfr1, pBLTdhfr2, pBLTdhfr1(GT), and pBLTdhfr2(GT)

A. Construction of Plasmids pBLThyg1 and pBLThyg2

About 4 μg of plasmid pBLT DNA (Example 15A) in 4 μl of TE buffer were added to 2 μl of 10× BamHI buffer and 12 μl of dH$_2$O. Two μl (about 10 units) of restriction enzyme BamHI were added to the solution of plasmid pBLT DNA, and the resulting reaction was incubated at 37° C. for 2 hours. The reaction was stopped by extracting the reaction mixture first with phenol and then with chloroform. The BamHI-digested plasmid pBLT DNA was then precipitated with ethanol and resuspended fn 2 µl of TE buffer.

About 10 µg of plasmid pSV2hyg in 10 µl of TE buffer were added to 10 µl of 10× BamHI buffer and 75 µl of dH$_2$O. Five µl (about 25 units) of restriction enzyme BamHI were added to the solution of plasmid pSV2hyg DNA, and the resulting reaction was incubated at 37° C. for 2 hours. The BamHI-digested plasmid pSV2hyg DNA was precipitated with ethanol, resuspended in 10 µl of TE buffer, loaded onto a 1% agarose gel, and electrophoresed until the ~2.5 kb BamHI restriction fragment that comprises the hygromycin resistance conferring gene was separated from the other digestion products. The ~2.5 kb restriction fragment was then isolated from the gel and prepared for ligation fn substantial accordance with the procedure of Example 4A; about 2 µg of the desired fragment were obtained and suspended in 10 µl of TE buffer.

About 2 µl of the BamHI-digested plasmid pBLT DNA and 1 µl of the ~2.5 kb BamHI restriction fragment of plasmid pSV2hyg were added to 1 µl of 10× ligase buffer, 5 µl of dH$_2$O, and 1 µl (about 500 units) of T4 DNA lfgase, and the resulting reaction was incubated at 16° C. overnight. The lfgated DNA constituted the desired plasmids pBLThyg1 and pBLThyg2. Plasmids pBLThyg1 and pBLThyg2 differ only with respect to the orientation of the ~2.5 kb BamHI restriction fragment that encodes the hygromycin resistance-conferring gene.

The ligated DNA was used to transform *E. coli* K12 HB101 in substantial accordance with the procedure of Example 3. The transformed cells were plated onto L-agar containing ampfcfllfn, and the ampicillin-resistant *E. coli* K12 HB101/pBLThyg1 and *E. coli* K12 HB101/pBLThyg2 transformants were identified by restriction enzyme analysis of their plasmid DNA.

B. Construction of Plasmids pBLThyg1(GT) and pBThyg2(GT)

A poly-GT element is inserted into the BamHI site in plasmid pBLThyg1 or pBLThyg2, between the tPA and hygromycin cistrons following partial digestion of the plasmids with BamHI. The partial digestion was carried out in substantial accordance with the general methodology for BamHI partial digestion as described in Example 11C on page 86. The poly-GT element and partially BamHI-digested linear plasmid pBLThyg1 or pBLThyg2 DNA are ligated and the ligated DNA constitutes the desired plasmids pBLThyg1(GT) and pBLThyg2(GT), respectively. A restriction site and function map of plasmid pBLThyg1(GT) is presented in FIG. 17 of the accompanying drawings.

C. Construction of Plasmids pBLTdhfr1 and pBLTdhfr2

About 100 µg of plasmid pBW32 (Example 11) in 100 µl of TE buffer were added to 15 µl of 10× BamHI buffer and 25 µl of dH$_2$O. Ten µl (about 50 units) of restriction enzyme BamHI were added to the solution of plasmid pBW32 DNA, and the resulting reaction was incubated at 37° C. for 2 hours. The BamHI-digested plasmid pBW32 DNA was precipitated with ethanol, resuspended in 10 µl of TE buffer, loaded onto a 1% agarose gel, and electrophoresed until the ~1.09 kb BamHI restriction fragment that comprises the dhfr gene was separated from the other digestion products. The ~1.09 kb restriction fragment was then isolated from the gel and prepared for ligation in substantial accordance with the procedure of Example 4A; about 10 µg of the desired fragment were obtained and suspended in 50 µl of TE buffer.

About 2 µl of the BamHI-digested plasmid pBLT DNA, obtained as in part A of this Example, and 1 µl of the ~1.09 kb BamHI restriction fragment of plasmid pBW32 were added to 1 µl of 10× ligase buffer, 5 µl of dH$_2$O, and 1 µl (about 500 units) of T4 DNA ligase, and the resulting reaction was incubated at 16° C. overnight. The ligated DNA constituted the desired plasmids pBLTdhfr1 and pBLTdhfr2. Plasmids pBLTdhfr1 and pBLTdhfr2 differ only with respect to the orientation of the ~1.09 kb BamHI restriction fragment that encodes the dhfr gene.

The ligated DNA was used to transform *E. coli* K12 HB101 in substantial accordance with the procedure of Example 3. The transformed cells were plated onto L-agar containing ampicillin, and the ampicillin-resistant *E. coli* K12 HB101/pBLTdhfr1 and *E. coli* K12 HB101/pBLTdhfr2 transformants were identified by restriction enzyme analysis of their plasmid DNA.

D. Construction of Plasmids pBLTdhfr1(GT) and pBLTdhfr2(GT)

A poly-GT element is inserted into the BamHI site in plasmid pBLTdhfr1 or pBLTdhfr2, in substantial accordance with the procedure of Example 16B. The poly-GT element and partially BamHI-digested linear plasmid pBLTdhfr1 or pBLTdhfr2 DNA are ligated and the ligated DNA constitutes the desired plasmids pBLTdhfr1(GT) and pBLTdhfr2(GT), respectively. A restriction site and function map of plasmid pBLTdhfr1(GT) is presented in FIG. 18 of the accompanying drawings.

EXAMPLE 17

Construction of Plasmids phdTPA, phd(GT)TPA, phdMTPA, and phd(Gl)MTPA

A. Construction of Intermediate Plasmid pTPA602

About 50 µg of plasmid pTPA103 (Example 11, FIG. 12) in 45 µl of dH$_2$O were added to 30 µl of 10× EcoRI buffer and 225 µl of dH$_2$O. Ten µl (about 80 units) of restriction enzyme EcoRI were added to the solution of plasmid pTPA103 DNA, and the resulting reaction was incubated at 37° C. for 90 minutes. The EcoRI-digested plasmid pTPA103 DNA was precipitated with ethanol, resuspended in 50 µl of IX loading buffer (10% glycerol and 0.02% bromophenol blue), loaded onto a 1% agarose gel, and electrophoresed until the ~1.01 kb EcoRI restriction fragment was separated from the other reaction products. The ~1.1 kb EcoRI restriction fragment that comprises the TPA amino-terminal-encoding DNA and was isolated from the gel by electrophoresing the fragment into a dialysis bag. The fragment was then precipitated with ethanol and resuspended in 160 µl of dH$_2$O.

About 40 µl of 10× HgaI buffer (0.5M NaCl; 60 mM Tris-HCl, pH=7.4; and 0.1M MgCl$_2$), 200 µl of dH$_2$O, and 20 µl (about 10 units) of restriction enzyme HgaI were added to the solution of ~1.01 kb EcoRI restriction fragment, and the resulting reaction was incubated at 37° C. for 4 hours. The HgaI-digested DNA was precipitated with ethanol and then electrophoresed on a 5% acrylamide gel, and the ~520 bp restriction fragment that encodes the amino terminus of TPA was isolated onto DE81 paper and recovered. About 5 µg of the ~520 bp HgaI fragment were obtained and suspended in 50 µl of dH$_2$O.

About 12.5 µl of 10× Klenow buffer (0.5M Tris-HCl, pH=7.4, and 0.1M MgCl$_2$), 2 µl of a solution that was 6.25 mM in each of the four deoxynucleotide triphosphates, 2 µl of 0.2M DTT, 1 µl of 7 µg/ml BSA, 57.5 µl of dH$_2$O, and 2 µl (about 10 units) of Klenow enzyme (Boehringer-Mannheim Biochemicals, 7941 Castleway Dr., P.O. Box 50816, Indianapolis, Ind. 46250) were added to the solution of the ~520 bp HgaI restriction fragment, and the resulting reaction was incubated at 20° C. for 30 minutes. The Klenow-treated DNA was incubated at 70° C. for 15 minutes and precipated with ethanol.

About 500 picomoles of BamHI linker (5'-CGGGATC-CCG-3', double-stranded and obtained from New England Biolabs) were phosphorylated using polynucleotide kinase in a total reaction volume of 25 µl. The reaction was carried out in substantial accordance with the procedure described in Example 7A. The kinased BamHI linkers were added to the solution of Klenow-treated, ~520 bp HgaI restriction fragment together with 15 µl of 10× ligase buffer, 7 µl (about 7 Weiss units) of T4 DNA ligase, and enough dH$_2$O to bring the total reaction volume to 150 µl. The resulting reaction was incubated at 16° C. overnight.

The ligation reaction was heat-inactivated, and the DNA was precipitated with ethanol and resuspended in 5 µl of 10× BamHI buffer and 45 µl of dH$_2$O. One µl (about 16 units) of restriction enzyme BamHI was added to the solution of DNA, and the resulting reaction was incubated at 37° C. for 90 minutes. Then, another 16 units of BamHI enzyme were added to the reaction mixture, and the reaction was incubated at 37° C. for another 90 minutes. The reaction mixture was then electrophoresed on a 5% polyacrylamide gel, and the ~530 bp HgaI restriction fragment, now with BamHI ends, was purified from the gel in substantial accordance with the procedure of Example 7A. About 2 µg of the desired fragment were obtained and suspended in 20 µl of dH$_2$O.

BamHI-digested, dephosphorylated plasmid pBR322 DNA can be obtained from New England Biolabs. About 0.1 µg of BamHI-digested, dephosphorylated plasmid pBR322 in 2 µl of dH$_2$O was added to 1 µl of the ~530 bp HgaI restriction fragment, with BamHI ends, of plasmid pTPA103, 14 µl of dH$_2$O, and 1 µl (about 1 Weiss unit) of T4 DNA ligase, and the resulting reaction was incubated at 16° C. overnight. The ligated DNA constituted the desired plamsid pTPA602 and an equivalent plasmid designated pTPA601, which differs from plasmid pTPA602 only with respect to the orientation of the inserted, ~530 bp restriction fragment.

The ligated DNA was used to transform E. coli K12 MM294 in substantial accordance with the procedure of Example 3, except that 50 mM CaCl$_2$ was used in the procedure. The transformed cells were plated on L-agar containing ampicillin, and the ampicillin-resistant E. coli K12MM294/pTPA602 and E. coli K12MM294/pTPA601 cells were identified by restriction enzyme analysis of their plasmid DNA. Presence of an ~530 bp BamHI restriction fragment indicated that the plasmid was either plasmid pTPA602 or pTPA601.

B. Construction of Intermediate Plasmid pTPA603

About 5 µg of plasmid pTPA602 was dissolved in 20 µl of 10× BglII buffer and 180 µl of dH$_2$O. Three µl (about 24 units) of restriction enzyme BglII were added to the solution of plasmid pTPA602 DNA, and the resulting reaction was incubated at 37° C. for 90 minutes. Then, about 13 µl of 10× BamHI buffer were added to the reaction mixture to bring the salt concentration of the reaction mixture up to that recommended for SalI digestion, and 2 µl (about 20 units) of restriction enzyme SalI were added to the reaction. The reaction was incubated at 37° C. for another 2 hours; then, the DNA was precipitated with ethanol, resuspended in 75 µl of loading buffer, loaded onto a 1% agarose gel, and electrophoresed until the ~4.2 kb BglII-SalI restriction fragment was separated from the other digestion products. The region of the gel containing the ~4.2 kb BglII-SalI restriction fragment was excised from the gel, frozen, and the frozen segment was wrapped in plastic and squeezed to remove the ~4.2 kb fragment. The DNA was precipitated and resuspended in 20 µl of H$_2$O; about 200 ng of the desired fragment were obtained.

About 12 µg of plasmid pTPA103 were dissolved in 15 µl of 10× BglII buffer and 135 µl of dH$_2$O. Two µl (about 16 units) of restriction enzyme BglII were added to the solution of plasmid pTPA103 DNA, and the resulting reaction was incubated at 37° C. for 90 minutes.

About 10 µl of 10× BamHI buffer were added to the solution of BglII-digested plasmid pTPA103 DNA to bring the salt concentration of the reaction mixture up to that required for SalI digestion. Then, about 2 µl (about 20 units) of restriction enzyme SalI were added to the solution of BglII-digested plasmid pTPA103 DNA, and the reaction was incubated at 37° C. for another 90 minutes. The BglII-SalI digested plasmid pTPA103 DNA was concentrated by ethanol precipitation and then loaded onto a 1% agarose gel, and the ~2.05 kb BglII-SalI restriction fragment that encodes all but the amino-terminus of TPA was isolated from the gel, precipitated with ethanol and resuspended in 20 µl of dH$_2$O. About 2 µg of the desired fragment were obtained.

About 5 µl of the ~4.2 kb BglII-SalI restriction fragment of plasmid pTPA602 and 2 µl of the ~2.05 kb BglII-SalI restriction fragment of plasmid pTPA103 were added to 2 µl of 10× ligase buffer, 10 µl of dH$_2$O, and 1 µl (about 1 Weiss unit) of T4 DNA ligase, and the resulting ligation reaction was incubated at 16° C. overnight. The ligated DNA constituted the desired plasmid pTPA603. A restriction site and function map of plasmid pTPA603 is presented in FIG. 19 of the accompanying drawings.

The ligated DNA was used to transform E. coli K12 MM294 in substantial accordance with the procedure of Example 3, except that 50 mM CaCl$_2$ was used in the procedure. The transformed cells were plated on L-agar containing ampicillin, and the ampicillin-resistant E. coli K12MM294/pTPA603 transformants were identified by restriction enzyme analysis of their plasmid DNA.

C. Construction of Plasmid pMTPA603

About 100 µg of plasmid pBLT (Example 15) in 100 µl of TE buffer were added to 10 µl of 10× SstI (SstI is equivalent to restriction enzyme SacI) buffer (60 mM Tris-HCl, pH=7.4; 60 mM MgCl$_2$; 60 mM 2-mercaptoethanol; and 1 mg/ml BSA) and 25 µl of dH$_2$O. Ten µl (about 50 units) of restriction enzyme SstI were added to the solution of plasmid pBLT DNA, and the resulting reaction was incubated at 37° C. for 2 hours. The SstI-digested plasmid pBLT DNA was precipitated with ethanol and resuspended in 10 µl of 10× Bgl1II buffer and 85 µl of dH$_2$O. Five µl (about 50 units) of restriction enzyme BglII were added to the solution of SstI-digested plasmid pBLT DNA, and the resulting reaction was incubated at 37° C. for 2 hours.

The BglII-SstI-digested plasmid pBLT DNA was precipitated with ethanol, resuspended in 10 µl of dH$_2$O, loaded onto a 1.5% agarose gel, electrophoresed, and the ~690 bp BglII-SstI restriction fragment of plasmid pBLT (which contains that portion of the modified TPA coding sequence wherein the deletion to get the modified TPA coding sequence has occurred) was isolated from the gel in substantial accordance with the procedure of Example 4A. About 5 µg of the desired ~690 bp BglII-SstI restriction fragment of plasmid pBLT was obtained and suspended in 100 µl of dH$_2$O.

About 5 µg of plasmid pTPA603 (part B of this Example, FIG. 19) in 5 µl of TE buffer were added to 10 µl of 10× SstI buffer and 95 μl of dH₂O. Five μl (about 50 units) of restriction enzyme SstI were added to the solution of plasmid pTPA603 DNA, and the resulting reaction was incubated at 37° C. for 2 hours. The SstI-digested plasmid pTPA603 DNA was precipitated with ethanol and resuspended in 10 μl of 10× BglII buffer and 85 μl of dH₂O. Five μl (about 50 units) of restriction enzyme BglII were added to the solution of SstI-digested plasmid pTPA603 DNA, and the resulting reaction was incubated at 37° C. for 2 hours. The Bgl II-SstI-digested plasmid pTPA603 DNA was diluted to 100 μl in TE buffer and treated with calf-intestinal alkaline phosphatase in substantial accordance with the procedure of Example 4B. The DNA was then precipitated with ethanol and resuspended in 10 μl of dH₂O.

About 5 μl of the BglII-SstI-digested plasmid pTPA603 and 2 μl of the ~690 bp BglII-SstI restriction fragment of plasmid pBLT were added to 2 μl of 10× ligase buffer, 10 μl of dH₂O, and 1 μl (about 1000 units) of T4 DNA ligase, and the resulting ligation reaction was incubated at 16° C. overnight. The ligated DNA constituted the desired plasmid pMTPA603. Plasmid pMTPA603 is thus analogous in structure to plasmid pTPA603 (FIG. 19), except that plasmid pMTPA603 encodes modified TPA, and plasmid pTPA603 encodes TPA.

The ligated DNA was used to transform *E. coli* K12 HB101 in substantial accordance with the procedure of Example 3. The transformed cells were plated on L-agar containing ampicillin, and the ampicillin-resistant *E. coli* K12 HB101/pMTPA603 transformants were identified by restriction enzyme analysis of their plasmid DNA.

D. Construction of Plasmid phdTPA

About 10 μg of plasmid pTPA603 (part B of this Example, FIG. 19) in 10 μl of TE buffer were added to 10 μl of 10× BamHI buffer and 85 μl of dH₂O. Five μl (about 50 units) of restriction enzyme BamHI were added to the solution of plasmid pTPA603 DNA, and the resulting reaction was incubated at 37° C. for 2 hours. The BamHI-digested plasmid pTPA603 DNA was precipitated with ethanol, resuspended in 10 μl of dH₂O, loaded onto a 1% agarose gel, and electrophoresed until the ~1.090 kb BamHI restriction fragment that encodes TPA was separated from the other digestion products. The ~1.090 kb BamHI restriction fragment was isolated from the gel and resuspended in 50 μl of TE buffer; about 4 μg of the desired fragment were obtained.

About 2 μg of plasmid phd (Example 13) in 2 μl of TE buffer were added to 2 μl of 10× BclI buffer and 14 μl of dH₂O. Two μl (about 10 units) of restriction enzyme BclI were added to the solution of plasmid phd DNA, and the resulting reaction was incubated at 50° C. for 2 hours. The reaction was stopped by extracting the reaction mixture first with phenol and then twice with chloroform. The BclI-digested plasmid phd DNA was then precipitated with ethanol and resuspended in 20 μl of TE buffer.

About 1 μl of the BclI-digested plasmid phd and 2 μl of the ~1.090 kb BamHI restriction fragment of plasmid pTPA603 were added to 1 μl of 10× ligase buffer, 5 μl of dH₂O, and 1 μl (about 500 units) of T4 DNA ligase. The resulting ligation reaction was incubated at 16° C. overnight. The ligated DNA constituted the desired plasmid phdTPA.

The ligated DNA was used to transform *E. coli* K12 HB101 (NRRL B-15626) in substantial accordance with the procedure of Example 3. The transformation mixture was plated on L-agar containing ampicillin, and the ampicillin-resistant *E. coli* K12 HB101/phdTPA cells were identified by restriction enzyme analysis. The ~1.90 kb BamHI restriction fragment could insert into BclI-digested plasmid phd in either one of two orientations, only one of which places the TPA coding sequence in the proper position to be expressed under the control of the BK enhancer-adenovirus late promoter cassette and thus results in the desired plasmid phdTPA.

E. Construction of Plasmid phd(GT)TPA

A poly-GT element is inserted into the unique XhoI site in plasmid phdTPA (part D of this Example), between the BK enhancer and the Ad2 late promoter, in substantial accordance with the procedure of Example 4B.1. The XhoI-digested poly-GT element and XhoI-digested plasmid phdTPA DNA are ligated and the ligated DNA constitutes the desired plasmid phd(GT)TPA. A restriction site and function map of plasmid phd(GT)TPA is presented in FIG. 20 of the accompanying drawings.

F. Construction of Plasmid phdMTPA

About 10 μg of plasmid pMTPA603 (part C of this Example) in 10 μl of TE buffer were added to 10 μl of 10× BamHI buffer and 85 μl of dH₂O. Five μl (about 50 units) of restriction enzyme BamHI were added to the solution of plasmid pMTPA603 DNA, and the resulting reaction was incubated at 37° C. for 2 hours. The BamHI-digested plasmid pMTPA603 DNA was precipitated with ethanol, resuspended in 10 μl of dH₂O, loaded onto a 1% agarose gel, and electrophoresed until the ~1.035 kb BamHI restriction fragment that encodes modified TPA was separated from the other digestion products. The ~1.035 kb BamHI restriction fragment was isolated from the gel and resuspended in 20 μl of TE buffer; about 4 μg of the desired fragment were obtained.

About 1 μl of the BclI-digested plasmid phd (part D of this Example) and 2 μl of the ~1.35 kb BamHI restriction fragment of plasmid pMTPA603 were added to 1 μl of 10× ligase buffer, 5 μl of dH₂O, and 1 μl (about 500 units) of T4 DNA ligase. The resulting ligation reaction was incubated at 16° C. overnight. The ligated DNA constituted the desired plasmid phdMTPA.

The ligated DNA was used to transform *E. coli* K12 HB101 in substantial accordance with the procedure of Example 3. The transformation mixture was plated on L-agar containing ampicillin, and the ampicillin-resistant *E. coli* K12 HB101/phdMTPA cells were identified by restriction enzyme analysis of their plasmid DNA. The ~1.35 kb BamHI restriction fragment could insert into BclI-digested plasmid phd in either one of two orientations, only one of which places the TPA coding sequence in the proper position to be expressed under the control of the BK enhancer-adenovirus late promoter and thus results in the desired plasmid phdMTPA.

G. Construction of Plasmid phd(GT)MTPA

A poly-GT element is inserted into the unique XhoI site in plasmid phdMPTA (part F of this Example), between the BK enhancer and the Ad2 late promoter, in substantial accordance with the procedure of Example 4B.1. The XhoI-digested poly-GT element and XhoI-digested plasmid phdMTPA DNA are ligated and the ligated DNA constitutes the desired plasmid phd(GT)MTPA. A restriction site and function map of plasmid phd(GT)MTPA is presented in FIG. 21 of the accompanying drawings.

EXAMPLE 18

Construction of an Improved Enhancer-Promoter Cassette

The transcription-enhancing effect of the BK enhancer can be significantly increased by placing the enhancer from 0 to 300 nucleotides upstream of the 5' end of the CCAAT region or CCAAT region equivalent of an adjacent eukaryotic promoter. Enhancement of transcription may be further increased by placing a poly-GT element upstream or downstream from the BK enhancer-Ad2 late promoter cassette in the presence of an immediate-early gene product of a large DNA virus, such as the E1A gene product, as described in Example 19. The sequence and functional elements of the present BK enhancer-Adenovirus 2 late promoter cassette, before modification to achieve greater enhancing activity, is depicted as follows:

```
                HindIII                                                              40
            5'-AAGCTTTTCT   CATTAAGGGA    AGATTTCCCC    AGGCAGCTCT
               ---------

80
                TTCAAGGCCT   AAAAGGTCCA    TGAGCTCCAT    GGATTCTTCC

120
                CTGTTAAGAA   CTTTATCCAT    TTTTGCAAAA    ATTGCAAAAG

StuI                                160
                AATAGGGATT   TCCCCAAATA    GTTTTGCTAG    GCCTCAGAAA
                                           -----------

200
                AAGCCTCCAC   ACCCTTACTA    CTTGAGAGAA    AGGGTGGAGG

240
                CAGAGGCGGC   CTCGGCCTCT    TATATATTAT    AAAAAAAAAG

280
                *-----------------------------------------  first repeat of the
                GCCACAGGGA   GGAGCTGCTT    ACCCATGGAA    TGCAGCCAAA 320
            BK enhancer---------------------------------  *  *-------------
                CCATGACCTC   AGGAAGGAAA    GTGCATGACT    CACAGGGGAA 360
            --- second repeat of the BK enhancer-----------------------------  *
                TGCAGCCAAA   CCATGACCTC    AGGAAGGAAA    GTGCATGACT 400
            *---------------------------------------------  third repeat
                CACAGGGAGG   AGCTGCTTAC    CCATGGAATG    CAGCCAAACC 440
            of the BK enhancer----------------------------- * | 43 bp insert,
                ATGACCTCAG   GAAGGAAAGT    GCATGACTGG    GCAGCCAGCC 480
            not found in BK(DUN)------------------- |
                AGTGGCAGTT   AATAGTGAAA    CCCCGCCGAC    AGACATGTTT

520
                TGCGAGCCTA   GGAATCTTGG    CCTTGTCCCC    AGTTAAACTG

StuI/PvuII                               560
                GACAAAGGCC   ATGGTTCTGC    GCCAGGCTGT    CCTCGAGCGG
                                                        ---------

SstI                                                               600
                TGTTCCGCGG   TCCTCCTCGT    ATAGAAACTC    GGACCACTCT
                ---------

640
                GAGACGAAGG   CTCGCGTCCA    GGCCAGCACG    AAGGAGGCTA

680
                AGTGGGAGGG   GTAGCGGTCG    TTGTCCACTA    GGGGGTCCAC

720
                TCGCTCCAGG   GTGTGAAGAC    ACATGTCGCC    CTCTTCGGCA

CAAT Region                             760
                TCAAGGAAGG   TGATTGGTTT    ATAGGTGTAG    GCCACGTGAC ----                        TATA Box                                800
                CGGGTGTTCC   TGAAGGGGGG    CTATAAAGG     GGGTGGGGGC
                                           ---------
```

-continued start site of transcription

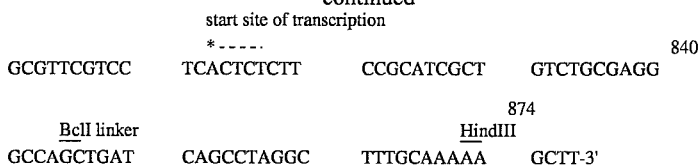

```
             874
  BclI linker              HindIII
GCCAGCTGAT   CAGCCTAGGC   TTTGCAAAAA   GCTT-3'
``` wherein A is deoxyadenyl; G is deoxyguanyl; C is deoxycytidyl; and T is thymidyl.

This depiction assumes that the BK enhancer is from the prototype strain of BK virus, available from the ATCC under the VR-837. However, ATCC VR-837 consists of a mixture of BK variants. Plasmid pBal8cat and the other BK enhancer-containing plasmids described herein comprise a BK enhancer variant isolated from the prototype strain, but not the BK prototype enhancer depicted. The sequence of the variant enhancer corresponding to positions 243 to 467 of the above depicted sequence of the prototype enhancer as found in plasmid pBal8cat and other plasmids herein is depicted as follows:

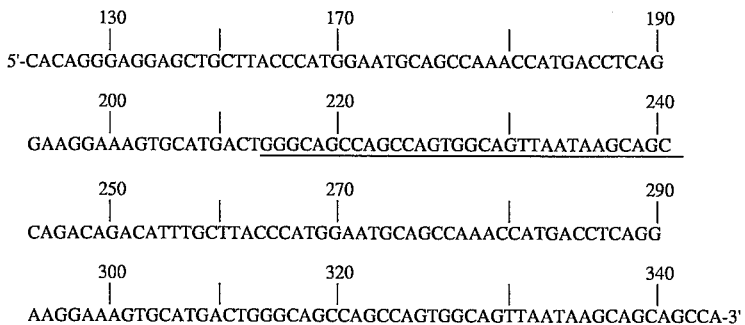

As stated above, however, any BK enhancer variant can be used in the methods and compounds of the present invention.

The prototype BK enhancer is defined by the three repeated sequences indicated in the sequence above and functions similarly, with respect to an adjacent sequence, in either orientation. To bring the enhancer, more specifically, the 3'end of the third repeat (which depends on the orientation) of the BK enhancer, closer to the 5'end of the CCAAT region of the adenovirus-2 late promoter, about 82 μg of SstII-digested plasmid pBLcat DNA (Example 5) in 170 μl of TE buffer were added to 20 μl of 5× Bal31 nuclease buffer (0.1M Tris-HCl, pH= 8.1; 0.5M NaCl; 0.06M $CaCl_2$; and 5 mM $Na_2EDTA$) and 9 μl of Bal31 nuclease, which was composed of 6 μl (about 6 units) of "fast" and 3 μl (about 3 units) of "slow" Bal31 enzyme (marketed by International Biotechnologies, Inc., P.O. Box 9558, 275 Winchester Ave., New Haven, Conn. 06506). The reaction was incubated at 30° C. for about 3 minutes; then, after about 10 μl of 1.0M EGTA were added to stop the reaction, the Bal31-digested DNA was collected by ethanol precipitation and centrifugation. The DNA pellet was resuspended in 1× Klenow buffer and treated with Klenow enzyme in substantial accordance with procedures previously described herein.

The Klenow-treated DNA was resuspended in 10 μl of TE buffer; about 1 μl of the DNA was then self-ligated in 10 μl of 1× ligase buffer using T4 DNA and RNA ligase as previously described. The ligated DNA was used to transform E. coli K12 HB101, and then the transformants were plated onto L-agar containing ampicillin. Restriction enzyme analysis was used to determine which transformants contained plasmids with an appropriately-sized BK enhancer-adenovirus 2 late promoter cassette. The foregoing procedure generates a number of plasmids in which the BK enhancer is placed within 0 to 300 nucleotides upstream of the CCAAT region of the adenovirus late promoter. One plasmid resulting from the above procedure was designated plasmid pBal8cat. Plasmid pBal8cat is available from the NRRL under the accession number NRRL B-18267. Plasmid pBal8cat contains a variant of the BK enhancer that contains two repeat sequences of about 100 bp each as shown above. This variant enhancer can be used in the method of the present invention by placing the 3'end of the second repeat within 0 to 300 nucleotides of the CCAAT region of the adenovirus late promoter.

Those skilled in the art will recognize that the foregoing procedure produced a number of distinct plasmids, of which plasmid pBal8cat is illustrative. These plasmids, as a group, represent placing the BK enhancer at a variety of distances less than 300 nucleotides from the CCAAT region of the Ad2 late promoter. This method for improving the activity of a BK enhancer, which can be achieved using the foregoing procedure or others known to those skilled in the art, can be used with any BK enhancer and any eukaryotic promoter.

EXAMPLE 19

Construction of an Improved
Poly-GT-Enhancer-Promoter Cassette

A poly-GT element may be inserted into the variety of distinct plasmids described in Example 18 above, of which plasmid pBal8cat is illustrative. These poly-GT containing plasmids, as a group, represent placing a poly-GT element in either orientation, and either 5'or 3' to the CAT gene, in expression vectors in which the BK enhancer has been placed at a variety of distances less than 300 nucleotides from the CCAAT region of the Ad2 late promoter and thus comprise an important aspect of the present invention. A poly-GT element was inserted into plasmid pBal8cat as follows. About 1 μg of pBal8cat DNA (Example 18) in 1 μl of TE buffer was dissolved in 2 μl of 10× Core buffer and 16 μl of $dH_2O$. One μl (about 10 units) of restriction enzyme BamHI was added to the solution of DNA, and the resulting reaction was incubated at 37° C. for 2 hours. Following this incubation, the mixture was heat-activated at 70° C. for 10 minutes.

Figure 22:
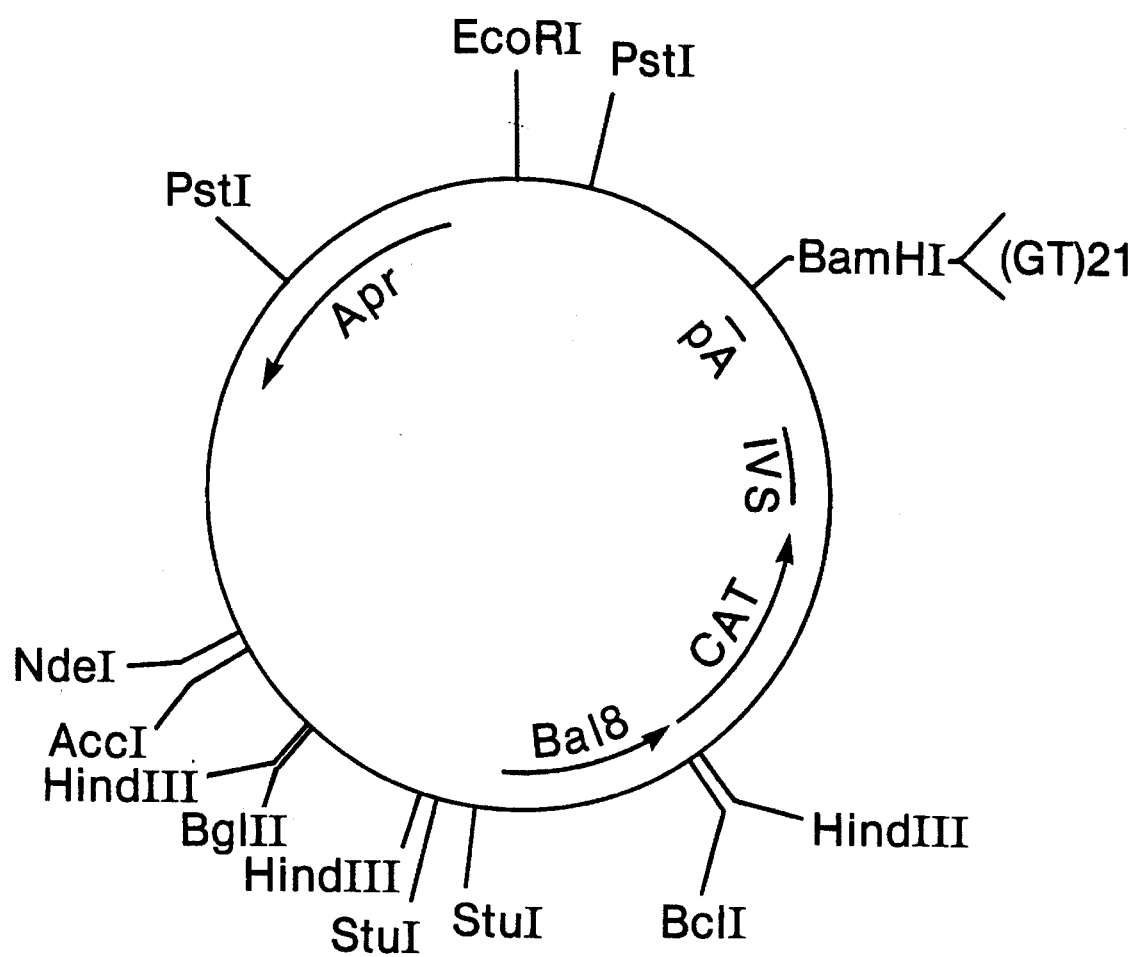
FIG. 22 is a restriction site and function map of plasmid pBalScat(GT6).

One µl of 10× ligase buffer was added to a mixture of 1 µl (about 50 ng) of the BamHI-digested pBal8cat DNA prepared above and 7 µl (about 500 ng) of the poly-GT synthetic fragment prepared as in Example 1. One µl (about 400 units) of T4 DNA ligase was added to the solution of DNA, and the resulting reaction was incubated at 16° C. overnight. The ligated DNA constituted the desired plasmids pBal8cat(GT6) (sense) and pBal8cat(GT9) (antisense) which differ only with respect to the orientation of the inserted poly-GT element relative to the CAT coding sequence. The enhancer activity of the poly-GT element in the presence of an immediate-early gene product of a large DNA virus, such as the E1A gene product, does not depend on the orientation of the poly-GT element in the plasmid expression vector into which it has been inserted. Thus, for example, plasmid pBal8cat(GT6) and plasmid pBal8cat(GT9) may be equally effective expression vectors for the CAT gene product in the presence of E1A. A restriction site and function map of plasmid pBal8cat(GT6) is presented in FIG. 22 of the accompanying drawings.

*E. coli* K12 HB101 cells (NRRL B-15626) were cultured, made competent for transformation, and transformed with the ligated DNA prepared above in substantial accordance with the procedure of Example 3. The transformed cells were plated on L-agar plates containing 100 µg/ml ampicillin. *E. coli* K12 HB101/pBal8cat(GT6) and *E. coli* K12 HB101/pBal8cat(GT9) transformants were identified by their ampicillin-resistant phenotype and by restriction enzyme analysis of their plasmid DNA. Plasmid pBal8cat(GT6) or pBal8cat(GT9) DNA was prepared in substantial accordance with the procedure of Example 3.

EXAMPLE 20

Construction of Plasmid pSV2E1A

*E. coli* K12 HB101/pSV2cat cells are obtained in lyophilized form from the ATCC under the accession number ATCC 37155, and plasmid pSV2cat DNA was isolated from the cells in substantial accordance with the procedure of Example 3. A restriction site and function map of plasmid pSV2cat is presented in FIG. 3 of the accompanying drawings. About 1 µg (1 µl) of the plasmid pSV2cat DNA were added to 2 µl of 10× core buffer and 14 µl dH$_2$O, and then 1.5 µl (about 15 units) of restriction enzyme StuI and 1.5 µl (about 15 units) of restriction enzyme EcoRI were added to the solution of pSV2cat DNA, and the resulting reaction was incubated at 37° C. for 2 hours. The reaction was terminated by heat inactivation at 70° C. for 10 minutes. After heat inactivation, 25 µl of dH$_2$O were added, then about 5 µl of 10× Klenow buffer and 2 µl (about 10 units) of Klenow enzyme were added to the mixture of DNA, and the resulting reaction was incubated at 16° C. for 1 hour. The Klenow-treated, StuI/EcoRI-digested plasmid pSV2cat DNA was then extracted twice with phenol:chloroform and then once with chloroform: isoamyl alcohol, precipitated with ethanol and resuspended in 20 µl of Tris buffer.

Figure 23:
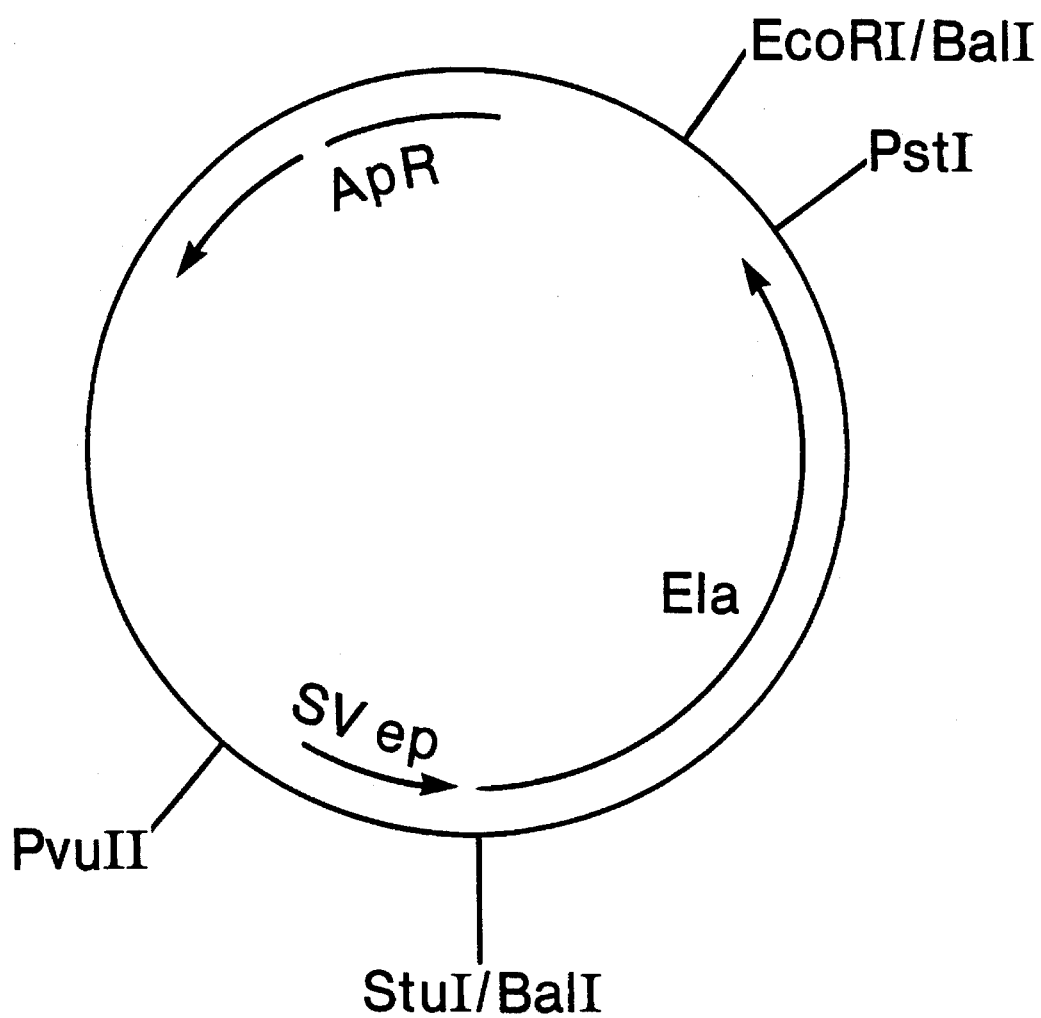
FIG. 23 is a restriction site and function map of plasmid pSV2E1A.

A fragment containing the E1A gene of adenovirus-2 DNA was isolated in substantial accordance with the procedure of Example 12A. The ~1.08 kb BalI fragment containing the E1A gene was isolated and about 9 µl (about 500 ng) of this fragment were added to 10 µl (about 100 ng) of the Klenow-treated, StuI/EcoRI-digested plasmid pSV2cat DNA described above, along with 1 µl dH$_2$O and 2.5 µl of 10× ligase buffer. Two and one-half µl (about 1250 units) of T4 DNA ligase were added to the solution of DNA, and the resulting reaction was incubated at 16° C. overnight. The ligated DNA constituted the desired plasmid pSV2E1A. A restriction site and function map of plasmid pSV2E1A is presented in FIG. 23 of the accompanying drawings.

Plasmid pSV2E1A is useful in the present invention as a source of the E1A gene in cotransformation experiments along with any other plasmid containing a poly-GT element, a eukaryotic promoter, and a recombinant gene to be expressed in the transformed host cells. Such plasmids include: pLP(GT)cat, pBL(GT)cat, pSBL(GT)cat, pLPC(GT), pLPC4(GT), pLPC5(GT), pLPChyg1(GT), pLPChyg2(GT), pLPCdhfr1(GT), pLPCdhfr2 (GT), pLPChd1 (GT), pLPChd2 (GT), pLPChd3 (GT), pLPChd4 ( GT ), pBLT (GT), pBLThyg1 (GT), pBLThyg2 (GT), pBLTdhfr1(GT), pBLTdhfr2(GT), phdTPA(GT), phdMTPA(GT), pBal8cat(GT6), pBal8cat(GT9) p4-14(GT), p2-5(GT) and pT6hd(GT). Alternatively, the E1A gene may be provided on a single plasmid along with the poly-GT element, eukaryotic promoter, and a recombinant gene to be expressed in transformed host cells, for example, plasmid pLPCE1A(GT) described in Example 14B.

EXAMPLE 21

Construction of plasmids pT6hd and pT6hd(GT)

A. Site-Specific Mutagenesis of the TPA Coding Region and Construction of Plasmid pT6hd Site specific mutagenesis of the TPA coding region and the construction of plasmid pT6hd is accomplished as follows. About 5 µg of plasmid pTPA103 (Example 17) in 10 µl of dH$_2$O are added to about 10 µl of 10× HindIII buffer and 80 µl of dH$_2$O. One µl (about 20 units) of restriction enzyme HindIII is added to the solution of plasmid pTPA103 DNA, and the resulting reaction is incubated at 37° C. for 90 minutes. One µl (about 20 units) of restriction enzyme SstI and 10 µl of 1M Tris HCl, pH=7.6, is added to the solution of HindIII-digested plasmid pTPA103 DNA, and the resulting reaction is incubated at 37° C. for 90 minutes. The HindIII-SstI-digested plasmid pTPA103 DNA is concentrated by ethanol precipitation, loaded onto a 1.5% agarose gel, and electrophoresed until the ~1.4 kb HindIII-SstI restriction fragment is separated from the other digestion products. About 0.5 µg of the ~1.4 bp HindIII-SstI restriction fragment is isolated from the gel in substantial accordance with the procedure of Example 4A, prepared for ligation, and resuspended in 20 µl of dH$_2$O.

About 4.5 µg of the replicarive form (RF) of M13mp18 DNA (available from New England Biolabs) in 35 µl of dH$_2$O is added to 10 µl of 10× HindIII buffer and 55 µl of dH$_2$O. One µl (about 20 units) of restriction enzyme HindIII is added to the solution of M13mp18 DNA, and the resulting reaction was incubated at 37° C. for 1 hour. One µl (about 20 units) of restriction enzyme SstI and 10 µl of 1M Tris-HCl, pH=7.6, is added to the solution of HindIII-digested M13mp18 DNA, and the resulting reaction is incubated at 37° C. for 1 hour. The HindIII-SstI-digested M13mp18 DNA is collected by ethanol precipitation, resuspended in preparation for agarose gel electrophoresis, and the large restriction fragment isolated by gel electrophoresis as described above. About 1 µg of the large HindIII-SstI restriction fragment of M13mp18 is obtained and suspended in 20 µl of dH$_2$O. About 2 µl of the large HindIII-SstI restriction fragment of M13mpl8, 2 µl of 10× T4 DNA ligase buffer, 12 μl of dH$_2$O and ~1 μl (about 1 Weiss unit) of T4 DNA ligase is added to 3 μl of the ~1.4 kb HindIII-SstI restriction fragment of plasmid pTPA103, and the resulting ligation reaction is incubated at 16° C. overnight.

*E. coli* JM103 cells (available from BRL) are made competent and transfected with the ligation mix in substantial accordance with the procedure described in the BRL M13 Cloning/'Dideoxy' Sequencing Instruction Manual, except that the amount of DNA used per transfection ts varied. Recombinant plaques are identified by insertional inactivation of the β-galactosidase α-fragment-encoding gene, which results in the loss of the ability to cleave X-Gal to its indigo-colored cleavage product. For screening purposes, several white plaques are picked into 2.5 ml of L broth, to which is added 0.4 ml of *E. coli* K12 JM103 logarithmic growth phase, that are cultured in minimal media stock to insure retention of the F episome that carries proAB. The 2.5 ml plaque-containing cell suspensions are incubated in an air-shaker at 37° C. for 8 hours. Cells from 1.5 ml aliquots are pelleted and RF DNA isolated in substantial accordance with the alkaline miniscreen procedure of Birnboim and Doly, 1979, *Nuc. Acids Res.* 7:1513. The remainder of each culture is stored at 4° C. for stock. The desired phage, designated MP18BW47, contains the ~1.4 kb HindIII-SstI restriction fragment of plasmid pBW25 ligated to the ~7.2 kb EcoRI-HindIII restriction fragment of M13mp18.

About fifty ml of log phase *E. coli* JM103 are infected with MP18BW47 and incubated in an air-shaker at 37° C. for 18 hours. The infected cells are pelleted by low speed centrifugation, and single-stranded MP18BW47 DNA is prepared from the culture supernatant by scaling up the procedure given in the Instruction Manual. Single-stranded MP18BW47 is mutagenized in substantial accordance with the teaching of Adelman et al., 1983, *DNA* 2(3): 183–193, except that the Klenow reaction is done at room temperature for 30 minutes, then at 37° C. for 60 minutes, then a 10° C. for 18 hours. In addition, the S1 treatment is done at 20° C., the salt concentration of the buffer is one-half that recommended by the manufacturer, and the M13 sequencing primer (BRL) is used. The synthetic oligodeoxyribonucleotide primer used to delete the coding sequence for amino acid residues 4 through 175 of native TPA is

5'-GGAGCCAGATCTTACCAAGGAAACAGTGACTGCTAC-3'.

The resulting mutagenesis mix is used to transfect *E. coli* K12 JM103 in substantial accordance with the infection procedure described above. Desired mutants are identified by restriction enzyme analysis of RF DNA and by Maxam and Gilbert DNA sequencing. The desired mutant, which has the coding sequence for amino acid residues 4 through 175 of native TPA deleted, is designated MP18BW52.

The restriction enzyme digestions, fragment isolations and ligations were all performed in substantial accordance with the procedures of Example 4. Plasmid pT6hd was constructed as follows. First, an ~1.9 kb BamHI fragment was obtained from plasmid pTPA603 (Example 17, FIG. 19). Next, plasmid pac373 (Miyamoto et al., 1985, *Mol. Cell. Biol.* 5:2860–2865) was digested with BamHI and ligated with the ~1.9 kb BamHI fragment from plasmid pTPA603 to create intermediate plasmid pL100. Plasmid pL100 DNA was then digested with restriction enzymes BglII and SstI and an ~1.02 kb BglII-SstI fragment was isolated.

MP18BW52 DNA, obtained as above, was digested with restriction enzymes BglII and SstI and an ~718 bp fragment was isolated. The ~718 bp BglII-SstI fragment of MP18BW52 was ligated with the ~1.02 kb BglII-SstI fragment of plasmid pL100 to create intermediate plasmid pL229. Plasmid pL229 DNA was then digested with restriction enzyme BamHI and an ~1.4 kb BamHI fragment was isolated. Plasmid phd (Example 13) was digested with BclI and ligated with the ~1.4 kb BamHI fragment of plasmid pL229 to create the desired plasmid pT6hd.

B. Construction of pT6hd(GT)

Figure 24:
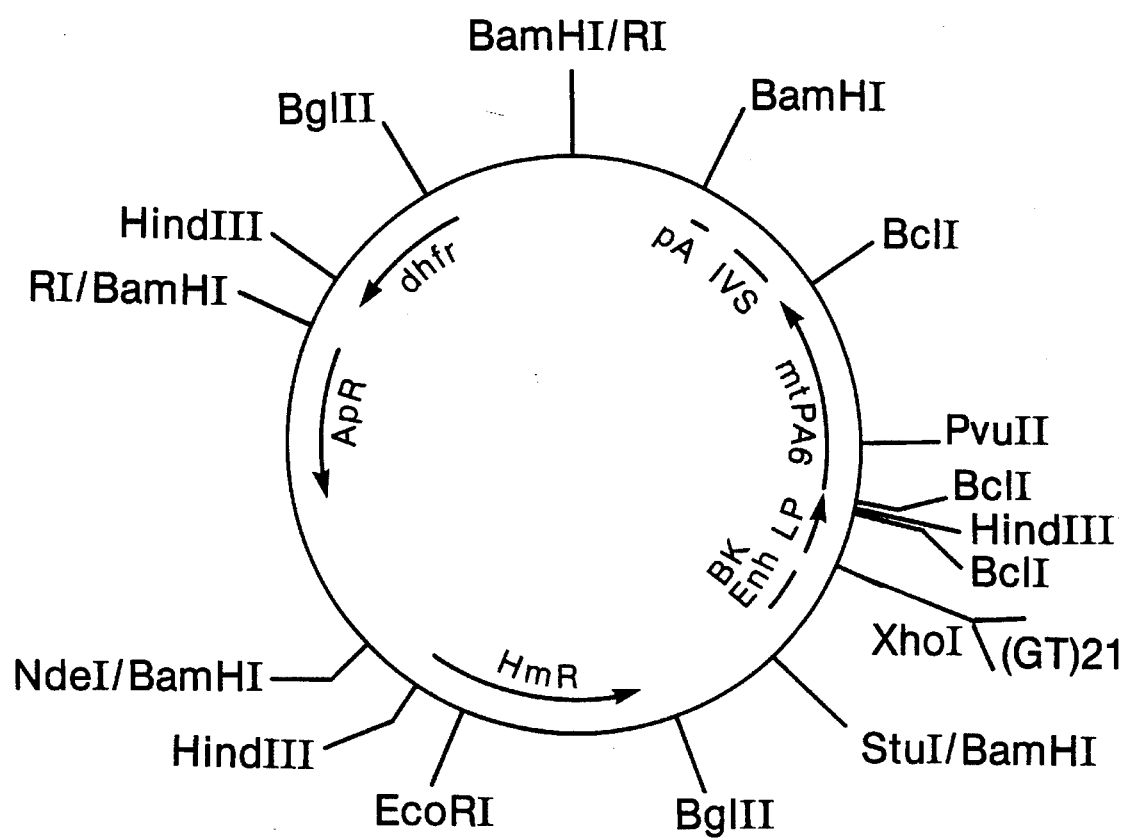
FIG. 24 is a restriction site and function map of plasmid pT6hd(GT).

A poly-GT element is inserted into the unique XhoI site in plasmid pT6hd, between the BK enhancer and the Ad2 late promoter, in substantial accordance with the procedure of Example 4B.1. The XhoI-digested poly-GT element and XhoI digested plasmid pT6hd are ligated and the ligated DNA constitutes the desired plasmid pT6hd(GT). A restriction site and function map of plasmid pT6hd(GT) is presented in FIG. 24 of the accompanying drawings.

Alternatively, plasmid pT6hd(GT) is constructed by ligating the ~1.4 kb BamHI fragment from plasmid pL229 (described in part A above) with BclI-digested plasmid phd(GT) (Example 13, FIG. 14) to create plasmid pT6hd(GT).

EXAMPLE 22

Construction of Eukaryotic Host Cell Transformats of Certain Expression Vectors

An important aspect of the expression vectors described herein concerns the use of a poly-GT element and a BK enhancer in such expression vectors to stimulate gene expression in the presence of the E1A gene product. Because 293 cells constitutively express the E1A gene product, 293 cells are the preferred host for the eukaryotic expression vectors of the present invention. The 293 cells are human embryonic kidney cells transformed with adenovirus type 5 (note that any particular type of adenovirus can be used to supply the E1A gene product in the method of the present invention) and are available from the ATCC under the accession number CRL 1573. Many of the expression vectors described herein function in a wide variety of host cells, even if the E1A gene product is not present. However, the E1A gene product (or similarly-acting immediate-early gene product of a large DNA virus) is required to activate the poly-GT element to enhance gene expression from the poly-GT-containing expression vectors of the present invention. The E1A gene product can be introduced into a non-E1A-producing cell line either by transformation with a vector that comprises the E1A gene, such as plasmids pSV2E1A, pLPCE1A and pLPCE1A1, or with sheered adenovirus DNA, or by infection with adenovirus.

The transformation procedure described below refers to 293 cells as the host cell line; however, the procedure is generally applicable to most eukaryotic cell lines. A variety of cell lines may be transformed with the vectors described herein. Because of the great number of expression vectors described herein, the transformation procedure is described generically.

The 293 cells are obtained from the ATCC under the accession number CRL 1573 in a 25 mm$^2$ flask containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (HBS) (Gibco), adding 0.25% trypsin for 1–2 minutes, rinsing with fresh medium, aspirating, and dispensing into new flasks at a subcultivation ratio of 1:5 or 1:10.

One day prior to transfection, cells are seeded at 0.7×10⁶ cells per dish. The medium is changed 4 hours prior to transfection. Sterile, ethanol-precipitated plasmid DNA dissolved in TE buffer is used to prepare a 2× DNA-CaCl₂ solution containing 40 µg/ml DNA and 250 mM CaCl₂. 2× HBS is prepared containing 280 mM NaCl, 50 mM HEPES, and 1.5 mM sodium phosphate, with the pH adjusted to 7.05–7.15. The 2× DNA-CaCl₂ solution is added dropwise to an equal volume of sterile 2× HBS. A one ml sterile plastic pipette with a cotton plug is inserted into the mixing tube that contains the 2× HBS, and bubbles are introduced by blowing while the DNA is being added. The calcium-phosphate-DNA precipitate is allowed to form without agitation for 30–45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the medium is replaced with DMEM with 10% fetal bovine serum and the cells allowed to incubated for an additional 72 hours before providing selective pressure. For transformants expressing recombinant human protein C, the growth medium contained 1 to 10 µg/ml vitamin K, a cofactor required for γ-carboxylation of the protein. For plasmids that do not comprise a selectable marker, that functions in eukaryotic cells, the transformation procedure utilizes a co-transformation technique with a mixture of plasmids: the expression vector described herein that lacks a selectable marker, and, an expression vector that comprises a selectable marker that functions in eukaryotic cells. This co-transformation technique allows for the identification of cells that comprise both of the transforming plasmids.

For cells transfected with plasmids containing the hygromycin resistance-conferring gene, hygromycin is added to the growth medium to a final concentration of about 200 to 400 µg/ml. The cells are then incubated at 37° C. for 2–4 weeks with medium changes at 3 to 4 day intervals. The resulting hygromycin-resistant colonies are transferred to individual culture flasks for characterization. The selection of neomycin-resistant colonies (G418 is also used in place of neomycin) is performed in substantial accordance with the selection procedure for hygromycin-resistant cells, except that G418 is added to a final concentration of 400 µg/ml rather than hygromycin. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr-positive phenotype.

The use of the dhfr gene as a selectable marker for introducing a gene or plasmid into a dhfr-deficient cell line and the subsequent use of methotrexate to amplify the copy number of the plasmid has been well established in the literature. Although the use of dhfr as a selectable and amplifiable marker in dhfr-producing cells has not been well studied, evidence in the literature would suggest that dhfr can be used as a selectable marker in dhfr-producing cells and for gene amplification. The use of the present invention is not limited by the selectable marker used. Moreover, amplifiable markers such as metallothionein genes, adenosine deaminase genes, or members of the multigene resistance family, exemplified by P-glycoprotein, can be utilized. In 293 cells, it is advantageous to transform with a vector that contains a selectable marker such as hygromycin B resistance-conferring gene and then amplify using methotrexate, which cannot be used for direct selection of murine dhfr-containing plasmids in 293 cells.

EXAMPLE 23

AV12 Eukaryotic Host Cell Transformants

Cell line AV12 (ATCC CRL 9595) can be transformed in substantial accordance with the procedure described for 293 cells in Example 22. However, unlike 293 cells, AV12 cells can be directly selected with methotrexate (200–500 nM) when transformed with a vector containing the murine dhfr gene. The advantages of producing a γ-carboxylated protein, for example, activated human protein C, in an adenovirus-transformed host cell are that such cells can produce protein C which is fully γ-carboxylated and fully active. The transformants are selected using hygromycin B or methotrexate; such transformants can produce about 2 to 4 µg/ml of human protein C. Protein C levels can be increased to about 50 µg/ml by amplification with methotrexate. The protein C is activated and its activity determined as described in Grinnell et al., 1987, Bio/Technology 5:1189.

The recombinant protein C activity produced in an adenovirus-transformed host cell such as AV12 is at least as active as that found in human blood. In non-adenovirus-transformed host cells, the anticoagulant activity of the recombinant protein C produced has not exceeded 60% of the activity of human blood-derived protein C.

EXAMPLE 24

Construction of Plasmids p4-14 p2-5, p4-14(GT) and p2-5(GT), Plasmids that Encode the Tripartite Leader of Adenovirus Plasmids p4-14(GT) and p2-5(GT) both utilize an improved poly-GT-BK-enhancer-adenovirus late promoter system and the tripartite leader (TPL) of adenovirus to drive high level expression of human protein C in eukaryotic host cells. Plasmids p4-14 and p2-5 are identical to plasmids p4-14(GT) and p2-5(GT), respectively, but lack a poly-GT element. The DNA encoding the adenovirus tripartite leader (TPL) was isolated from adenovirus; numbers in parentheses after restriction enzyme cut sites refer to map units of adenovirus.

Plasmid pUG13 (commercially available from BRL) was digested with restriction enzymes SphI and BamHI and then ligated with the TPL-encoding ~7.2 kb SphI (5135)-BclI (12,301) restriction fragment of adenovirus type 2 to yield plasmid pTPL4. Part of an intron was deleted from the TPL-encoding DNA by digesting plasmid pTPL4 with restriction enzymes SauI (7616) and BglII (8904), treating with Klenow enzyme, and religating to yield plasmid pΔTPL. Plasmid pΔTPL was then digested with restriction enzyme XhoI, and the ~2.62 kb XhoI fragment encoding the TPL (XhoI sites at 5799 and 9689 of adenovirus) was isolated and prepared for ligation.

Plasmid pBLcat was digested with restriction enzyme BclI. A linker having the following sequence was synthesized and annealed in substantial accordance with the procedure of Example 1:

and this linker was ligated to BclI-digested plasmid pBLcat, followed by digestion with XhoI. The XhoI-digested plasmid pBLcat DNA with the ligated linker was then ligated to yield plasmid pBALcat. This construction replaces the adenovirus late promoter on plasmid pBLcat with the linker sequence. Plasmid pBALcat was digested with restriction enzyme XhoI and ligated with the ~2.62 kb XhoI restriction fragment of plasmid pΔTPL to yield plasmid pBAL-TPL, in which the TPL-encoding fragment is correctly positioned to place the BK enhancer, adenovirus major late promoter, and TPL in alignment for expression of the CAT gene.

Plasmid p2-5 was then constructed by ligating these fragments: (1) the AatII-BclI restriction fragment of plasmid pLPChd1, which encodes the dhfr gene; (2) the protein C-encoding, BclI restriction fragment of plasmid pLPChd1; (3) the TPL-encoding PvuII-BclI restriction fragment of plasmid pBΔL-TPL; and (4) the BK-enhancer-Ad2MPL-encoding PvuII-AatII restriction fragment of plasmid pBal8cat. Plasmid p2-5 thus contains the dhfr gene as a selectable, amplifiable marker and the BK enhancer, Ad2MLP, and Ad2 TPL correctly positioned to drive expression of human protein C.

Plasmid p4-14 is analogous to plasmid p2-5 but was constructed via an intermediate plasmid designated pBal8TPL. Plasmid pBal8TPL was constructed by ligating fragments 1, 3, and 4, used in the construction of plasmid p2-5, as described in the preceding paragraph. Plasmid pBal8TPL was then digested with restriction enzyme XhoI, treated with Klenow enzyme to make the XhoI ends blunt-ended, and then ligated with the human protein C-encoding, Klenow-treated BclI restriction fragment of plasmid pLPChd1 to yield plasmid p4-14. Thus, plasmid p4-14 only differs from plasmid p2-5 in that the protein C-encoding DNA was inserted at the XhoI site in the fragment derived from plasmid pBΔL-TPL, whereas in plasmid p2-5, this DNA was inserted at the BclI site in the DNA derived from plasmid pBΔL-TPL.

Plasmid p4-14 and p2-5 drive high-level expression of human protein C. In AV12 cells, plasmids p4-14 and p2-5 can be directly selected using 200-500 nM methotrexate. AV12/p4-14 transformants, before amplification, express 5-6 times more human protein C than AV12/pLPCdhfr transformants. Amplification with methotrexate further increases the amount of human protein C produced by the cells. Plasmids p4-14 and p2-5 are thus illustrative of the higher expression levels achieved using the Bal8 promoter and the TPL of adenovirus.

Still higher levels of expression in the presence of E1A gene product may be achieved by inserting a poly-GT element into plasmid p4-14 or p2-5 as follows. A poly-GT element is inserted into the unique BclI site in plasmid p4-14 at the 3' end of the protein C coding sequence (BclI is compatible with BamHI) to yield plasmid p4-14(GT). A poly-GT element is inserted into the unique XhoI site in plasmid p2-5 at the junction between the TPL and the protein C coding sequence, to yield plasmid p2-5(GT).

EXAMPLE 26

Determination of Recombinant Gene Expression Levels in Eukaryotic Host Cell Transfectants of Certain Poly-GT Expression Vectors A variety of eukaryotic host cells have been transfected with the poly-GT-containing expression vectors of the present invention. In certain of these transfectants, expression levels of the structural gene encoded in these recombinant poly-GT-containing expression vectors have been determined and compared with expression levels from corresponding expression vectors that lack a poly-GT element. In several experiments, three different cell lines were transfected with plasmids pLPcat, pLP(GT)cat, pBLcat, pBL(GT)cat, pBal8cat and pBal8cat(GT6) in substantial accordance with the procedure of Example 21. The above listed plasmids each contain the gene-coding sequence for chloramphenicol acetyltransferase (CAT). Relative levels of CAT activity were determined by the method of Gorman et. al., 1982, Mol. Cell. Biol. 2:1044-1051. The level of CAT activity by each plasmid is presented in Table 2 below as the average of 1 to 5 separate experiments. Relative CAT activities varied by only 10 to 15% between experiments.

TABLE 2

Relative Levels of Chloramphenicol Acetyltransferase (CAT) Produced by Recombinant Plasmids in Various Human and Monkey Kidney Cell Lines
Relative Level* of CAT in Cell Line:

| Plasmid | 293 (ATCC CRL 1573) | MK2 (ATCC CCL7) | COS-1 (ATCC CRL 1650) |
|---|---|---|---|
| pLPcat | 1 | 1 | 1 |
| pLP(GT)cat | 4 | 1 | NT |
| pBLcat | 66 | 28 | 8 |
| pBL(GT)cat | 208 | 21 | 8 |
| pBal8cat | 479 | 20 | NT |
| pBal8cat(GT6) | 958 | NT | 11 |

*The values for the relative levels of CAT produced in each cell line were based on the level of CAT from plasmid pLPcat as unity in that cell line. NT = not tested. Only the 293 cell line produces E1A (MK2 and COS-1 are E1A negative). Only the COS-1 cell line produces T antigen (293 and MK2 are T antigen negative).

Plasmid pLP(GT)cat is illustrative of an expression vector that contains a poly-GT element, no enhancer, and the Ad2 late promoter, whereas plasmid pBL(GT)cat is illustrative of an expression vector that contains a poly-GT element, the BK enhancer and the Ad2 late promoter. Plasmid pBal8cat(GT6) is similar to plasmid pBL(GT)cat except that pBal8cat(GT6) contains a modified enhancer-promoter region with the poly-GT element 3' to the CAT gene. To determine the effect of the poly-GT element, the plasmid expression vectors listed in Table 2 were transfected into various cell lines and CAT activity determined, as described above. Table 2 shows that in the MK2 cell line, the poly-GT element had no stimulatory effect or enhancer-like activity with the Ad2 late promoter; the relative levels of CAT produced from plasmids pLPcat and pLP(GT) were approximately the same. However, in the presence of E1A, as shown by the results with plasmids pLPcat and pLP(GT)cat in the 293 (E1A+) cell line, a 4 fold increase in CAT activity was observed with plasmid pLP(GT)cat which contains a poly-GT element, as compared with plasmid pLPcat. This illustrates the trans-activation of the poly-GT element by E1A.

When plasmids pBL(GT)cat and pBLcat were used to transfect 293 cells, the poly-GT element was again trans-activated by E1A. An approximately 4 fold increase in CAT activity was observed with plasmid pBL(GT)cat as compared with plasmid pBLcat. Plasmid pBL(GT)cat shows greater than 200 times the activity of plasmid pLPcat, due to the combined enhancer activity of the poly-GT element and the BK enhancer in the presence of E1A. Using the MK2 cell line and the T antigen-producing COS-1 cell line, levels of expression from plasmids pBL(GT)cat and pBLcat were approximately the same, again demonstrating the poly-GT element requires E1A for trans-activation and further demonstrating that the poly-GT element is not trans-activated by T antigen.

Highest levels of expression were achieved with plasmid pBa18cat(GT6), which showed nearly a 1000 fold increase in relative levels of CAT over those with plasmid pLPcat. Plasmid pBa18cat(GT6) is illustrative of the improved expression vectors of this invention, which contain an E1A activated poly-GT element and a modifed BK enhancer-promoter region.

We claim:

1. In a method for producing a useful substance in a human host cell wherein said cell is comprises a DNA sequence that codes for the expression of an immediate-early gene product of a human adenovirus, and said cell is transformed with a recombinant DNA vector that comprises a human adenovirus late promoter and a DNA sequence that encodes a useful substance, said DNA sequence that encodes a useful substance being positioned for expression from said promoter, and wherein said cell containing said vector is cultured under conditions suitable for expression of said useful substance, the improvement comprising introducing into said cell with a poly-GT element positioned on said vector to stimulate said promoter, so that culturing said cell under conditions suitable for expressing said immediate-early gene product stimulates the activity of said promoter due to the presence of said poly-GT element.

2. The method of claim 1 wherein the immediate-early gene product of a human adenovirus is selected from the group consisting of adenovirus E1A protein and adenovirus E1B protein.

3. The method of claim 2 wherein the immediateearly gene product of a human adenovirus is adenovirus E1A protein.

4. The method of claim 1 wherein the DNA that codes for the expression of said human adenovirus immediate-early gene product is contained in a recombinant DNA vector.

5. The method of claim 4 wherein said vector further comprises said human adenovirus late promoter, poly-GT element, and DNA sequence that encodes a useful substance.

6. The method of claim 5 wherein said immediate-early gene product of a human adenovirus is selected from the group consisting of adenovirus E1A protein and adenovirus E1B protein.

7. The method of claim 6, wherein said immediate-early gene product of a human adenovirus is the adenovirus E1A protein.

8. The method of claim 7, wherein said useful substance is human protein C.

9. The vector of the method of claim 8 that is selected from the group consisting of plasmids pLPCE1A(GT) and pLPCE1A1(GT).

10. In a method for producing a useful substance in a human host cell wherein said cell expresses an immediate-early gene product of a human adenovirus, and said cell is transformed with a recombinant DNA vector that comprises a human adenovirus late promoter and a DNA sequence that encodes a useful substance, said DNA sequence that encodes a useful substance being positioned for expression from said promoter, and wherein said cell containing said vector is cultured under conditions suitable for expression of said useful substance, the improvement comprising introducing into said cell with a poly-GT element positioned on said vector to stimulate said promoter, so that culturing said cell under conditions suitable for expressing said immediate-early gene product stimulates the activity of said promoter due to the presence of said poly-GT element.

11. The method of claim 10 wherein the immediate-early gene product of a a human adenovirus is selected from the group consisting of adenovirus E1A protein and adenovirus E1B protein.

12. The method of claim 11 wherein the immediate-early gene product of a human adenovirus is adenovirus E1A protein.

13. The method of claim 10 wherein the human host cell is a 293 cell.

14. The method of claim 10 wherein said recombinant DNA vector is a plasmid.

15. The method of claim 14 wherein the plasmid is selected from the group consisting of plasmids pLP(GT)cat, pBL(GT)cat, pSBL(GT)cat, pLPC(GT), pLPC4(GT), pLPC5 (GT), pLPChyg1(GT), pLPChyg2(GT), pLPCdhfr1(GT), pLPCdhfr2(GT), pLPChd1(GT), pLPChd2(GT), pLPChd3(GT), pLPChd4(GT), pBLT(GT), pBLThyg1(GT), pBLThyg2(GT), pBLTdhfr1(GT), pBLTdhfr2(GT), phdTPA(GT), phdMTPA(GT), pBa18cat(GT6), pBa18cat(GT9) p4–14(GT), p2–5(GT) and pT6hd(GT).

16. A method of producing a protein in a eukaryotic host cell that comprises:
(a) transforming said host cell with a recombinant DNA vector that comprises:
(1) a poly GT element;
(2) an SV40 enhancer;
(3) a BK enhancer;
(4) a human adenovirus late promoter; and
(5) a DNA sequence that encodes said protein and that is positioned for expression from said promoter; and
(b) culturing said host cell transformed in step (a) under conditions that allow for gene expression.

17. The method of claim 16, wherein said vector is selected from the group consisting of plasmids pSBL(GT)cat, pLPC(GT), pLPChyg1(GT), pLPCdhfr1(GT), and pLPChd1(GT).

18. The method of claim 16, wherein said protein is human protein C.

19. A plasmid that comprises a poly-GT element positioned to stimulate transcription from the human adenovirus-2 late promoter in the presence of an immediate-early gene product of a human adenovirus.

20. The plasmid of claim 19 that further comprises the BK enhancer positioned to stimulate transcription from said adenovirus-2 late promoter.

21. The plasmid of claim 20 that is plasmid phd(GT).

22. The plasmid of claim 19 that comprises a poly-GT element positioned to stimulate transcription, from the human adenovirus-2 late promoter in the presence of an immediate-early gene product of a human adenovirus, of a DNA sequence that encodes a protein.

23. The plasmid of claim 22, wherein said protein is chloramphenicol acetyltransferase.

24. The plasmid of claim 23 that is pLP(GT)cat.

25. The plasmid of claim 23 that further comprises the BK enhancer positioned to stimulate transcription from the human adenovirus-2 late promoter.

26. The plasmid of claim 25 selected from the group consisting of plasmids pBL(GT)cat, pBa18cat(GT6), and pBa18cat(GT9).

27. The plasmid of claim 22 wherein said protein is human protein C.

28. The plasmid of claim 27 that further comprises the BK enhancer positioned to stimulate transcription from the human adenovirus-2 late promoter.

29. The plasmid of claim 28 selected from the group consisting of plasmids pLPC(GT), pLPC4(GT), pLPC5(GT), pLPChyg1(GT), pLPChyg2(GT), pLPCdhfr1(GT), pLPCdhfr2(GT), pLPChd1(GT), pLPChd2(GT), pLPChd3(GT), and pLPChd4(GT).

30. The plasmid of claim 28 that further comprises the E1A gene of human adenovirus.

31. The plasmid of claim 30 selected from the group consisting of plasmids pLPCE1A(GT) and pLPCE1A1(GT).

32. The plasmid of claim 22 that further comprises the SV40 enhancer and the BK enhancer positioned to stimulate transcription from the human adenovirus-2 late promoter.

33. The plasmid of claim 32 that is plasmid pSBL(GT)cat.

34. The plasmid of claim 22 that further comprises the BK enhancer positioned to stimulate transcription from the human adenovirus-2 late promoter.

35. The plasmid of claim 34 selected from the group consisting of plasmids pBLT(GT), pBLThyg1(GT), pBLThyg2(GT), pBLTdhfr1(GT), and pBLTdhfr2(GT).

36. The plasmid of claim 34 wherein said protein is tissue plasminogen activator.

37. The plasmid of claim 36 that is phdTPA(GT).

38. The plasmid of claim 34 wherein said protein is a modified tissue plasminogen activator.

39. The plasmid of claim 38 that is selected from the group consisting of phdMTPA(GT) and pT6hd(GT).

40. The plasmid of claim 34 wherein said protein is an interferon.

41. The plasmid of claim 40 wherein said protein is selected from the group consisting of an α-interferon, β-interferon and γ-interferon.

42. The plasmid of claim 34 that further comprises DNA that encodes the tripartite leader of adenovirus between the human adenovirus-2 late promoter and the DNA sequence that encodes a protein.

43. The plasmid of claim 42 selected from the group consisting of plasmids p4–14(GT), and p2–5(GT).

44. A human host cell transformed with a plasmid of claim 22.

45. The 293 host cell of claim 16 that is a 293 host cell transformed with plasmid pLPC(GT).

46. The 293 host cell of claim 16 that is a 293 host cell transformed with plasmid pLPC4(GT).

47. The 293 host cell of claim 16 that is a 293 host cell transformed with plasmid pLPChyg1(GT).

48. The 293 host cell of claim 16 that is a 293 host cell transformed with plasmid pLPCdhfr1 (GT).

49. The 293 host cell of claim 16 that is a 293 host cell transformed with plasmid pLPChd1(GT).

50. The 293 host cell of claim 16 that is a 293 host cell transformed with plasmid p4–14(GT).

51. The 293 host cell of claim 16 that is a 293 host cell transformed with plasmid pT6hd(GT).

* * * * *

UNITED STATES PATENT AND TRADEMARK OFFICE
CERTIFICATE OF CORRECTION

PATENT NO. : 5,506,118

DATED : April 9, 1996

INVENTOR(S) : David T. Berg and Brian W. Grinnell

It is certified that error appears in the above-indentified patent and that said Letters Patent is hereby corrected as shown below:

In Claim 1, column 77, line 21, delete the word "is".

In Claim 6, column 77, line 52, please add the following text after the word protein, --and wherein said vector is a plasmid--.

In Claim 16, column 78, line 28, please delete the word "eukaryotic" and add the word --293--.

Signed and Sealed this

Twenty-first Day of January, 1997

Attest:

BRUCE LEHMAN

Attesting Officer

Commissioner of Patents and Trademarks